US010201617B2

(12) United States Patent
Sun

(10) Patent No.: US 10,201,617 B2
(45) Date of Patent: Feb. 12, 2019

(54) 3-SUBSTITUTED PIPERIDINE-2, 6-DIONES AND NON-COVALENT COMPLEXES WITH ALBUMIN

(71) Applicant: Zhuhai Beihai Biotech Co., Ltd., Zhuhai (CN)

(72) Inventor: Qun Sun, Princeton, NJ (US)

(73) Assignee: Zhuhai Beihai Biotech Co., Ltd., Zhuhai (CN)

( * ) Notice: Subject to any disclaimer, the term of this patent is extended or adjusted under 35 U.S.C. 154(b) by 0 days.

(21) Appl. No.: 15/520,770

(22) PCT Filed: Oct. 22, 2015

(86) PCT No.: PCT/US2015/056900
§ 371 (c)(1),
(2) Date: Apr. 20, 2017

(87) PCT Pub. No.: WO2016/065139
PCT Pub. Date: Apr. 28, 2016

(65) Prior Publication Data
US 2017/0319708 A1 Nov. 9, 2017

Related U.S. Application Data

(60) Provisional application No. 62/068,573, filed on Oct. 24, 2014.

(51) Int. Cl.
*C07D 401/04* (2006.01)
*A61K 47/64* (2017.01)
*A61K 9/00* (2006.01)
*A61K 9/08* (2006.01)
*A61K 9/19* (2006.01)
*A61K 31/454* (2006.01)

(52) U.S. Cl.
CPC .......... *A61K 47/643* (2017.08); *A61K 9/0019* (2013.01); *A61K 9/08* (2013.01); *A61K 9/19* (2013.01); *A61K 31/454* (2013.01); *C07D 401/04* (2013.01)

(58) Field of Classification Search
None
See application file for complete search history.

(56) References Cited

U.S. PATENT DOCUMENTS

| | | | |
|---|---|---|---|
| 5,604,213 A | 2/1997 | Barrie et al. | |
| 5,635,517 A | 6/1997 | Muller et al. | |
| 7,445,764 B1 | 11/2008 | Kratz | |
| 7,452,900 B2 | 11/2008 | Marzi | |
| 7,498,340 B2 | 3/2009 | Marzi | |
| 7,576,104 B2 | 8/2009 | Robarge et al. | |
| 7,772,254 B2 | 8/2010 | Sun | |
| 7,820,788 B2 | 10/2010 | Desai et al. | |
| 7,923,536 B2 | 4/2011 | Desai et al. | |
| 8,076,374 B2 | 12/2011 | Hunt | |
| 8,114,621 B2 * | 2/2012 | Salamone | C07D 401/04 435/7.1 |
| 8,138,229 B2 | 3/2012 | Desai et al. | |
| 8,338,588 B2 | 12/2012 | Hunt | |
| 8,748,610 B2 | 6/2014 | Sun | |
| 8,853,260 B2 | 10/2014 | Desai et al. | |
| 8,911,775 B2 | 12/2014 | Lee et al. | |
| 8,927,725 B2 | 1/2015 | Greig et al. | |
| 9,029,548 B2 * | 5/2015 | Milne | A61K 47/48038 546/201 |
| 9,150,585 B2 | 10/2015 | Sun | |
| 2009/0253651 A1 | 10/2009 | Norbedo | |
| 2011/0021567 A1 | 1/2011 | Devarakonda et al. | |
| 2012/0177743 A1 | 7/2012 | Desai et al. | |
| 2012/0283292 A1 | 11/2012 | Milne et al. | |
| 2014/0024807 A1 | 1/2014 | Salamone et al. | |
| 2014/0135356 A1 | 5/2014 | Sun | |
| 2015/0290332 A1 | 10/2015 | Kim et al. | |
| 2015/0291562 A1 | 10/2015 | Crew et al. | |
| 2015/0366984 A1 | 12/2015 | Sun | |
| 2016/0145314 A1 | 5/2016 | Li et al. | |
| 2017/0216443 A1 | 8/2017 | Sun | |

FOREIGN PATENT DOCUMENTS

| | | |
|---|---|---|
| CN | 1863790 | 11/2006 |
| EP | 2007386 | 8/2012 |
| WO | WO2003066595 | 8/2003 |
| WO | WO2005030753 | 4/2005 |
| WO | WO2008133973 | 11/2008 |
| WO | WO2009023539 | 2/2009 |
| WO | WO2009074678 | 6/2009 |
| WO | WO2009126920 | 10/2009 |
| WO | WO2010092342 | 8/2010 |

(Continued)

OTHER PUBLICATIONS

US 8,977,694, 01/2015, McDonagh et al. (withdrawn)
"Multiple Myeloma: Treatment Options," Cancer.Net [online] Sep. 2014 [retrieved on Sep. 23, 2014]. Retrieved from the Internet: <URL: http://www.cancer.net/cancer-types/multiple-myeloma/treatment-options>, 7 pages.
"Myelodysplastic Syndromes Treatment (PDQ®)," Cancer.gov [online] Jun. 11, 2014 [retrieved on Sep. 24, 2014]. Retrieved from the Internet: <URL: http://www.cancer.gov/cancertopics/pdq/treatment/myelodysplastic/page1/AllPages/Print>, 17 pages.
"Pomalyst® (pomalidomide) capsules, for oral use," [prescribing information], Feb. 2013, 13 pages.
"Revlimid [lenalidomide] capsules, for oral use," [prescribing information], Jun. 2013, 33 pages.

(Continued)

*Primary Examiner* — Heidi Reese
(74) *Attorney, Agent, or Firm* — Fish & Richardson P.C.; Vasily A. Ignatenko

(57) ABSTRACT

The present disclosure provides derivatives of 3-substituted piperidine-2, 6-diones, non-covalently bound complexes with serum albumin, pharmaceutical compositions of the same, and methods of use thereof. The non-covalently bound complexes are significantly more water-soluble than the parent compounds, and are useful for the treatment of a cancer, such as multiple myeloma.

14 Claims, 2 Drawing Sheets

(56) References Cited

FOREIGN PATENT DOCUMENTS

| WO | WO2011085000 | 7/2011 |
|---|---|---|
| WO | WO2014121033 | 8/2014 |

OTHER PUBLICATIONS

"Revlimid® (lenalidomide) capsules Data sheet," 22 pages, Apr. 2013.
"Zytiga® (abiraterone acetate) Tablets," [prescribing information], Dec. 2012, 9 pages.
Accession No. 158:253017 CA, 1 page, 2012.
Accession No. 158:662530 CA, 1 page, 2012.
Akhtar et al., "Cytochrome b(5) modulation of 17 {alpha} hydroxylase and 17-20 lyase (CYP17) activities in steroidogenesis," *J Endocrinol.*, 187(2):267-274, Nov. 2005.
Birder et al., "Altered urinary bladder auction in mice lacking the vanilloid receptor TRPV1," *Nat. Neurosci.*, 5(9):856-860, Sep. 2002.
Bley, "Recent developments in transient receptor potential vanilloid receptor 1 agonist-based therapies," Exp. Opin Investig Drugs., 13(11):1445-1456, Nov. 2004.
Bosse et al., "Phase I comparability of recombinant human albumin and human serum albumin," *J Clin Pharmacol.*, 45(1):57-67, Jan. 2005.
Briggs et al., "An adverse reaction to the administianon of disoprofol (Diprivan)," *Anaesthesia*, 37(11):1099-1101, Nov. 1982.
Bruno et al., "Population pharmacokinetics/pharmacodynamics of docetaxel in phase II studies in patients with cancer," *J Clin Oncol.*, 16(1):187-196, Jan. 1998.
Carter and Ho, "Structure of serum albumin," *Adv Protein Chem.*, 45:153-203, 1994.
Caterina et al., "Impaired nociception and pain sensation in mice lacking the capsaicin receptor." *Science*, 288(5464):306-313, Apr. 2000.
Caterina et al., "The capsaicin receptor: a heat-activated ion channel in the pain pathway," *Nature*, 389(6653):816-824, Oct. 23, 1997.
Chen et al., "Human sebum albumin from recombinant DNA technology: challenges and strategies." *Biochim Biophys Acta.*, 1830(12):5515-1525, Epub May 3, 2013.
Chen et al., "Removal of fatty acids from serum albumin by charcoal treatment," *J Biol Chem.*, 242(2):173-181, Jan. 25, 1967.
Chen et al., "Results of molecular docking as descriptors to predict human serum albumin binding affinity," *J Mol Graph Model.*, 33:35-43, Epub Nov. 23, 2011.
ClinicalTrials.gov Identifier: NCT00783367, "Combination Therapy Using Lenalidomide (Revlimid)—Low Dose Dexamethasone and Rituximab for Treatment of Rituximab-Resistant, Non-Aggressive B-Cell Lymphomas," ClinicalTrials.gov [online] xx [retrieved on Sep. 24, 2014]. Retrieved from the Internet: <URL: https://clinicaltrials.gov/ct2/show/NCT00783367?term=lenalidomide&rank=4>, 5 pages.
ClinicalTrials.gov Identifier: NCT01183663, "Lenalidomide in Combination With Bevacizumab, Sorafenib, Temsirolimus, or 5-Fluorouracil, Leucovorin, Oxaliplatin (FOLFOX)," ClinicalTrials.gov [online] Aug. 11, 2014 [retrieved on Sep. 24, 2014]. Retrieved from the Internet: <URL: https://clinicaltrials.gov/ct2/show/NCT01183663?term=lenalidomide&rank=9>, 5 pages.
ClinicalTrials.gov Identifier: NCT01358734, "A Study Being Conducted at Multiple Locations to Compare the Safety and Effectiveness of Three Different Treatment Regimens; 1) Lenalidomide, 2) Lenalidomide + Azacitidine, or 3) Azacitidine Alone in Newly Diaziosed Acute Myeloid Leukemia in Elderly Subjects ≥ 65 Years of Age," ClinicalTrials.gov [online] Jun. 30, 2014 [retrieved on Sep. 24, 2014]. Retrieved from the Internet: <URL: https://clinicaltrials.gov/ct2/showNCT01358734?term=lenalidomide&rank=15>, 4 pages.
ClinicalTrials.gov Identifier: NCT01460940, "A Phase II Trial of Panobinostat and Lenalidomide in Patients With Relapsed or Refractory Hodgkin's Lymphoma," ClinicalTrials.gov [online] Jul. 15, 2013 [retrieved on Sep. 24, 2014]. Retrieved from the Internet: <URL: https://clinicaltrials.gov/ct2/show/NCT01460940?term=lenalidomide&rank=13>, 5 pages.
ClinicalTrials.gov Identifier: NCT01704781, "Vacc-4x + Lenalidomide vs. Vacc-4x +Placebo in HIV-1-infected Subjects on Antiretroviral Therapy (ART) (IMID)," ClinicalTrials.gov [online] Jul. 30, 2014[retrieved on Sep. 24, 2014]. Retrieved from the Internet: <URL: https://clinicaltrials.gov/ct2/show/NCT01704781?term=lenalidomide&rank=1, 4 pages.
Cohn and Strong, "Preparation and properties of serum and plasma proteins: a system for the separation into fractions of the protein and lipoprotein components of biological tissues and fluids," *J Am Chem Soc.*, 68:459-475, Mar. 1946.
Curry et al., "Crystal structure of human serum albumin complexed with fatty acid reveals an asymmetric distribution of binding sites," *Nat Struct Biol.*, 5(9):827-835, Sep. 1998.
Davis et al., "Vanilloid receptor-1 is essential for inflammatory thermal hyperalgesia," Nature, 405(6783): 183-187, May 11, 2000.
Di Marzo et al., "Endovanilloid signaling in pain," *Curr. Opin. Neurobiol.*, 12(4):372-379, Aug. 2002.
EMEA, "Scientific Discussion," 42 pages, 2007.
Fehske et al., "The location of drug binding sites in human serum albumin," *Biochem Pharmacol.*, 30(7):687-692, Apr. 1, 1981.
Ferrajoli et al., "Combination therapy with lenalidomide and rituximab in patients with relapsed chronic lymphocytic leukemia (CCL)," Blood, (ASH Annual Meeting Abstracts) 114: Abstract 206, 2 pages, 2009.
Finlayson, "Albumin Products," *Seminars in Thrombosis and Hemostasis*, 6(2):85-120, 1980.
Ge et al., "Protein-polymer hybrid nanoparticles for drug delivery," *Small.*, 8(23):3573-3578, Epub Aug. 9, 2012.
He et al., "Atomic structure and chemistry of human serum albumin," *Nature*, 358(6383):209-215, Jul. 16, 1992.
Hideshima et al., "A review of lenalidomide in combination with dexamethasone for the treatment of multiple myeloma," *Ther Clin Risk Manag.*, 4(1):129-136, Feb. 2008.
International Preliminary Report on Patentability for PCT /US2014/014079, dated Aug. 13, 2015, 7 pages.
International Search Report and Written Opinion for PCT/US2014/14079 dated May 13, 2014, 8 pages.
International Preliminary Report on Patentability of the International Application No. PCT/US2015/38077, dated Jan. 5, 2017, 7 pages.
International Search Report and Written Opinion of the International Application No. PCT/US2015/38077, dated Sep. 24, 2015, 15 pages.
International Preliminary Report on Patentability for PCT/US2015/056900, dated May 4, 2017, 7 pages.
International Search Report and Written Opinion for PCT/US2015/056900, dated Dec. 29, 2015, 13 pages.
Janssen, "Zytiga® abiraterone acetate product information." Mar. 1, 2012, 12 pages.
Kasim et al., "Molecular properties of WHO essential drugs and provisional biopharmaceutical classification," *Mol Pharm.*, 1(1):85-96, Jan. 12, 2004.
Kotla et al., "Mechanism of action of lenalidomide in hematological malignancies," *J Hematol Oncol.*, 2:36, Aug. 12, 2009.
Kragh-Hansen, "Structure and ligand binding properties of human serum albumin," *Dan Med Bull.*, 37(1):57-84, Feb. 1990.
Klutz, "Albumin as a drug carrier: design of prodrugs, drug conjugates acid nanoparticles," *J Control Release.*, 132(3):171-183. Epub May 17, 2008.
Kularatne et al., "Synthesis and biological analysis of prostate-specific membrane antigen-targeted anticancer prodrugs," *J Med Chem.*, 53(21):7767-7777, Nov. 11, 2010.
Li et al., "Preparation, characterization and targeting of micronized 10-hydroxycamptothecin-loaded folate-conjugated human serum albumin nanoparticles to cancer cells," *Int J Nanomedicine.*, 6:397-405, Epub Feb. 20, 2011.
Lin et al., "Stability of human serum albumin during bioprocessing: denaturation and aggregation during processing of albumin paste," *Pharm Res.*, 17(4):391-396, Apr. 2000.

(56) References Cited

OTHER PUBLICATIONS

Lipinski, "Drug-like properties and the causes of poor solubility and poor permeability," *J Pharmacol Toxicol Methods*, 44(1):235-249, Jul.-Aug. 2000.

Lopez-Gomez, "Management of colorectal cancer patients after resection of liver metastases: can we offer a tailored treatment?" *Clin Transl Oncol.*, 14(9):641-658, Epub Aug. 22, 2012.

Mezey et al., "Distribution of mRNA for vanilloid receptor subtype 1 (VR1), and VR1-like immunoreactivity, in the central nervous system of the rat and human," *Proc Natl Acad Sci U S A.*, 97(7):3655-3660, Mar. 28, 2000.

Piccart et al., "Docetaxel: an active new drug for treatment of advanced epithelial ovarian cancer," *J Natl Cancer Inst.*, 87(9):676-681, May 3, 1995.

Pomonis et al., "N-(4-Tertiarybutylphenyl)-4-(3-cholorphyridin-2-yl)tetrahydropyrazine-1(-2H)-carbox-amide (BCTC), a novel, orally effective vanilloid receptor 1 antagonist with analgesic properties: II. in vivo characterization in rat models of inflammatory and neuropathic pain," J Pharmacol Exp Ther., 306(1):387-393, Epub. Apr. 29, 2003.

Prijovich et al., "Stability of the new prodrug 9-aminocamptothecin glucuronide (9ACG) in the presence of human serum albumin," Biochem Pharmacol., 66(7):1181-1187, Oct. 1, 2003.

Rajkumar et al., "Combination therapy with lenalidomide plus dexamethasone (Rev/Dex) for newly diagnosed myeloma," *Blood*, 106(13):4050-4053, Epub Aug. 23, 2005.

Ratain, "Flushing oral oncology drugs down the toilet," *J Clin Oncol.*, 29(30):3958-3959, Epub Sep. 19, 2011.

Ryan et al., "Structural basis of binding of fluorescent, site-specific dansylated amino acids to human serum albumin," *Journal of Structural Biology.*, 174:84-91, 2011.

Samor et al., "The role of polyamine architecture on the pharmacological activity of open lactone camptothecin-polyamine conjugates," *Bioconjug Chem.*, 19(11):2270-2279. Nov. 19, 2008.

Sartor et al., "Novel therapeutic strategies for metastatic prostate cancer in the post-docetaxel setting," *Oncologist.*, 16(11):1487-1497, Epub Nov. 2, 2011.

Schmid et al., "Development of albumin-binding camptothecin prodrugs using a Peptide positional scanning library," *Bioconjug Chem.*, 18(6):1786-1799, Epub Oct. 5, 2007.

Semeraro et al., "Trial Watch: Lenalidomide-based immunochemotherapy," 2(11):e26494. Epub Oct. 21, 2013.

Silverman and Holladay, *The Organic Chemistry of Drug Design and Drug Action*, Elsevier, pp. 29-32, 2004.

Sugio et al., "Crystal structure of human serum albumin at 2.5 A resolution," *Protein Eng.*, 12(6):439-446, Jun. 1999.

Todd et al., "Fast and flawed or scientifically sound: the argument for administering oral oncology drugs during fasting," *J Clin Oncol.*, 30(8):888-889, Epub Feb. 13, 2012.

Trudeau et al., "Docetaxel in patients with metastatic breast cancer: a phase II study of the National Cancer Institute of Canada—Clinical Trials Group," *J Clin Oncol.*, 14(2):422-428, Feb. 1996.

Trynda-Lemiesz, "Effect of cis-, trans-diamminedichloroplatinum(II) and DBP on human serum albumin," *J Inorg Biochem.*, 77(3-4):141-146, Nov.-Dec. 1999.

Tullis, "Albumin. 1. Background and use," *JAMA.*, 237(4):355-360, Jan. 24, 1977.

Vannucchi, "Management of myelofibrosis," Hematology Am Soc Hematol Educ Progam., 2011:222-230, 2011.

Vorum, "Reversible ligand binding to human serum albumin. Theoretical and clinical aspects," *Dan Med Bull.*, 46(5):379-399, Nov. 1999.

Walker et al., "The VR1 antagonist capsazepine reverses mechanical hyperalgesia in models of inflammatory and neuropathic pain," *J. Pharm. Exp. Ther.*, 304(1): 56-62, Jan. 2003.

Yu et al., "Spectroscopic investigation of the interaction between camptothecin and bovine serum albumin," Fenxi Shiyanshi, 31(1): 42-46, 2012 [English abstract].

Zhang, "Methoxy poly(ethylene glycol) conjugated denatured bovine serum albumin micelles for effective delivery of camptothecin," Polym Chem, 3(8):1958-1961, Aug. 2012.

Zsila, "Evaluation of drug-human serum albumin binding interactions with support vector machine aided online automated docking," *Bioinformatics*, 27(13):1806-1813, Epub May 18, 2011.

Zu et al., "Preparation of 10-hydroxycamptothecin-loaded glycyrrhizic acid-conjugated bovine serum albumin nanoparticles for hepatocellular carcinoma-targeted drug delivery," *Int J Nanomedicine.*, 8:1207-1222, Epub Mar. 27, 2013.

International Preliminary Report on Patentability for PCT/US2015/056900, dated May 4, 2017, 6 pages.

Marbury et al, Chemical Abstract 162:265369, Abstract of Journal of Clinical Pharmacology, 53(7), pp. 732-741 (Year: 2013).

\* cited by examiner

3-SUBSTITUTED PIPERIDINE-2, 6-DIONES AND NON-COVALENT COMPLEXES WITH ALBUMIN

CROSS REFERENCE TO RELATED APPLICATIONS

This application claims the benefit of U.S. Provisional Ser. No. 62/068,573 filed Oct. 24, 2014. This disclosure of the prior application is considered part of (and is incorporated by reference in) the disclosure of this application.

TECHNICAL FIELD

This disclosure relates to 3-substituted piperidine-2, 6-diones, non-covalent complexes of the compounds with albumin, for example, human serum albumin, methods of preparation and pharmaceutical uses thereof.

BACKGROUND

About 30% of drugs that appear on the World Health Organization (WHO) Essential Drug List were reported to be poorly water-soluble, based on the Biopharmaceutics Classification System (BCS). See, for example, Kasim, N. A., et al., Molecular properties of WHO essential drugs and provisional biopharmaceutical classification, *Molecular Pharmaceutics* 2004, 1(1): p. 85-96. Over 40% of newly developed pharmaceutically active substances have solubility issues (Lipinski, C. A., Drug-like properties and the causes of poor solubility and poor permeability, *Journal of Pharmacological and Toxicological Methods* 2000, 44(1): p. 235-249). The poor dissolution and/or permeability of these drugs often result in low and highly variable bioavailability. An obstacle in commercializing these compounds can be the difficulty of enhancing the extent of dissolution and dissolution rate of the active pharmaceutical ingredient.

Lenalidomide (Revlimid®) is approved in the United States as an oral treatment for multiple myeloma in combination with dexamethasone in patients who have received at least one prior therapy, transfusion-dependent anemia due to certain myelodysplastic syndromes, and relapsed mantle cell lymphoma. Though lenalidomide is soluble in organic solvents and in acidic solutions, its solubility is significantly reduced at pH closer to 7, ranging from 0.4 to 0.5 mg/mL (Revlimid® Full Prescribing Information, June 2013, Celgene Corporation, Section 11).

Pomalidomide (Pomalyst®) is approved in the United States as an oral treatment for multiple myeloma progressing in patients who have received at least two prior therapies. The solubility of pomalidomide is low, about 0.01 mg/mL, regardless of pH (Pomalyst® Full Prescribing Information, February 2013, Celgene Corporation, Section 11).

Additionally, pomalidomide is a substrate of the CYP1A2 and CYP3A liver enzymes, which can lead to adverse drug-drug interactions with other therapies that may be taken that inhibit and/or induce one or both enzymes (Pomalyst® Full Prescribing Information, February 2013, Celgene Corporation, Section 7).

While their insolubility allows for their preparation in capsule form for oral dosing, lenalidomide and pomalidomide are precluded from intravenous (IV) administration used in other treatments for, e.g., multiple myeloma, such as bisphosphonate therapy. The development of soluble lenalidomide and pomalidomide derivatives would allow for IV dosing, which can alleviate some of the aforementioned problems.

Accordingly, there is a clear and continuing need to create more soluble forms of lenalidomide and pomalidomide.

SUMMARY

Provided herein is a non-covalently bound complex of a lenalidomide or a pomalidomide derivative and human serum albumin in a molar ratio in the range of from about 1:1 to about 10:1, wherein the non-covalently bound complex has a solubility in aqueous solution of 5 mg/mL or more, and the lenolidomide or pomalidomide derivative comprises a compound of Formula (I):

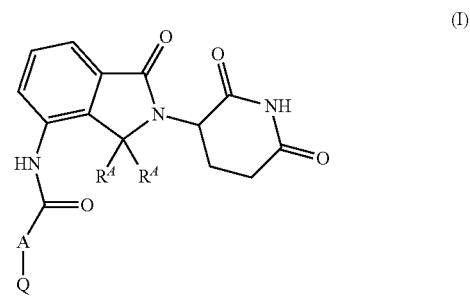

wherein A is a covalent bond, O or $NR^1$;

$R^1$ is, independently in each instance, H or lower alkyl optionally substituted with 1-3 substituents independently selected from the group consisting of: halo, nitro, amine, amide, hydroxyl, O-lower alkyl and carboxy;

each $R^A$ is H, or both $R^A$ taken together is oxo; and

Q is a group that selectively binds to human serum albumin.

Also provided herein is a compound of Formula (II):

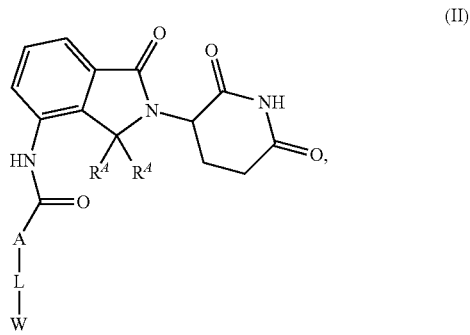

or a pharmaceutically acceptable salt thereof, wherein

A is a covalent bond, O or $NR^1$;

each $R^A$ is H, or both $R^A$ taken together is oxo;

L is alkyl, alkyl-O-alkyl, alkenyl, alkynyl, carbocyclyl, carbocyclylalkyl, aryl, alkaryl,

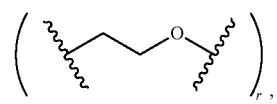

or a linker comprising a —S—S— bond, each of which is optionally substituted with 1-3 substituents independently selected from the group consisting of halo, —NO₂, amine, amide, hydroxyl, O-lower alkyl and —COOH, provided that there be no covalent bonds between oxygen atoms;

W is

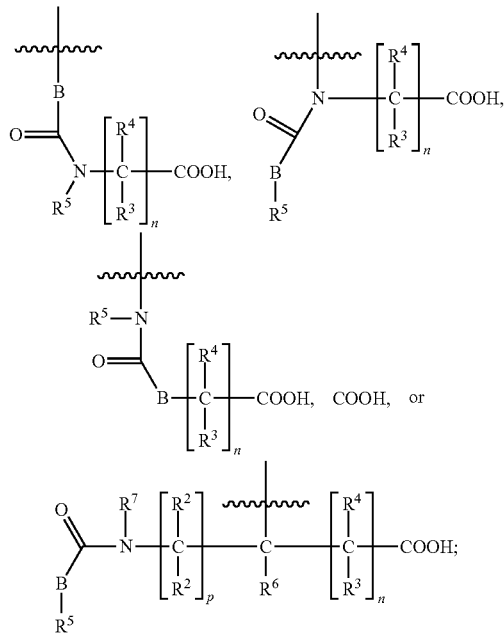

R¹ is H, lower alkyl, or alkaryl, wherein the alkyl or alkaryl is optionally substituted with 1-3 substituents independently selected from the group consisting of: halo, $NO_2$, amine, amide, hydroxyl, O-lower alkyl and —COOH;

$R^2$ is independently in each instance H, OH, $NO_2$, $NH_2$, SH or a branched or unbranched $C_{1-8}$ alkyl, $C_{2-8}$ alkenyl or $C_{2-8}$ alkynyl, wherein the $C_{1-8}$ alkyl, $C_{2-8}$ alkenyl or $C_{2-8}$ alkynyl is optionally substituted with 1-2 substituents independently selected from the group consisting of halo, OH, $NO_2$, $NH_2$, SH and =O, and wherein the $C_{1-8}$ alkyl, $C_{2-8}$ alkenyl or $C_{2-8}$ alkynyl optionally has 1-2 heteroatoms independently selected from O, S and NH wherein each heteroatom replaces a $CH_2$, with the proviso that no O, S or N atom in the $C_{1-8}$ alkyl, $C_{2-8}$ alkenyl or $C_{2-8}$ alkynyl is covalently bonded to another O, S or N atom;

$R^3$ is independently in each instance H, alkyl, alkenyl, alkynyl, alkyl-O-alkyl, alkyl-O-aryl, phenyl, or alkaryl, wherein the alkyl, alkenyl, alkynyl, alkyl-O-alkyl, alkyl-O-aryl, phenyl, or alkaryl is optionally substituted with 1-3 substituents independently selected from the group consisting of: halo, —NO₂, —CF₃, amido, sulfonamide, aryl, —OH, alkyl, —O-lower alkyl, —O-alkaryl, and —O-aryl;

$R^4$ is independently in each instance H, OH, $NO_2$, $NH_2$, SH or a branched or unbranched $C_{1-10}$ alkyl, $C_{2-10}$ alkenyl or $C_{2-10}$ alkynyl, wherein the $C_{1-10}$ alkyl, $C_{2-10}$ alkenyl or $C_{2-10}$ alkynyl is optionally substituted with 1-2 substituents independently selected from the group consisting of halo, OH, $NO_2$, $NH_2$, SH and =O, and wherein the $C_{1-10}$ alkyl, $C_{2-10}$ alkenyl or $C_{2-10}$ alkynyl optionally has 1-2 heteroatoms independently selected from O, S and NH wherein each heteroatom replaces a $CH_2$, with the proviso that no O, S or N atom in the $C_{1-10}$ alkyl, $C_{2-10}$ alkenyl or $C_{2-10}$ alkynyl is covalently bonded to another O, S or N atom;

$R^5$ is H, alkyl, alkenyl, alkynyl, alkyl-O-alkyl, alkyl-O-aryl, phenyl, or alkaryl, wherein the alkyl, alkenyl, alkynyl, alkyl-O-alkyl, alkyl-O-aryl, phenyl, or alkaryl is optionally substituted with 1-3 substituents independently selected from the group consisting of: halo, —NO₂, —CF₃, amido, sulfonamide, aryl, —OH, alkyl, —O-lower alkyl, —O-alkaryl, and —O-aryl;

$R^6$ and $R^7$ is each independently H or lower alkyl, optionally substituted with 1-3 substituents independently selected from the group consisting of halo, nitro, amine, amide, hydroxyl, O-lower alkyl and carboxy;

B is a covalent bond, O or $NR_1$;

p is 1, 2, 3, 4, 5, or 6;

n is 1, 2, 3, 4, 5, or 6; and r is 1, 2, 3, 4, 5, 6, 7, 8, 9, or 10.

Also provided herein is a non-covalently bound complex of a compound as described herein, or pharmaceutically acceptable salt thereof, and human serum albumin in a molar ratio in the range of from about 1:1 to about 10:1, wherein the non-covalently bound complex has solubility in aqueous solution of 5 mg/mL or more.

Provided herein is a pharmaceutical composition comprising a non-covalently bound complex as described herein, and a pharmaceutically acceptable carrier.

Also provided herein is a method of treating a cancer, the method comprising the step of administering to a subject in need thereof a therapeutically effective amount of a pharmaceutical composition as described herein.

Also provided herein is a method of treating a disease or condition that is beneficially treated by administering a tumor necrosis factor inhibitor, the method comprising the step of administering to a subject in need thereof a therapeutically effective amount of a pharmaceutical composition as described herein.

Unless otherwise defined, all technical and scientific terms used herein have the same meaning as commonly understood by one of ordinary skill in the art to which this disclosure belongs. Methods and materials are described herein for use in the present disclosure. Other suitable methods and materials known in the art can also be used. The materials, methods, and examples are illustrative only and not intended to be limiting.

All publications, patent applications, patents, and other references mentioned herein are incorporated by reference in their entirety. In case of conflict, the present specification, including definitions, will control.

Other features and advantages of the disclosure will be apparent from the following detailed description, and from the claims.

DETAILED DESCRIPTION

Definitions

Figure 1:
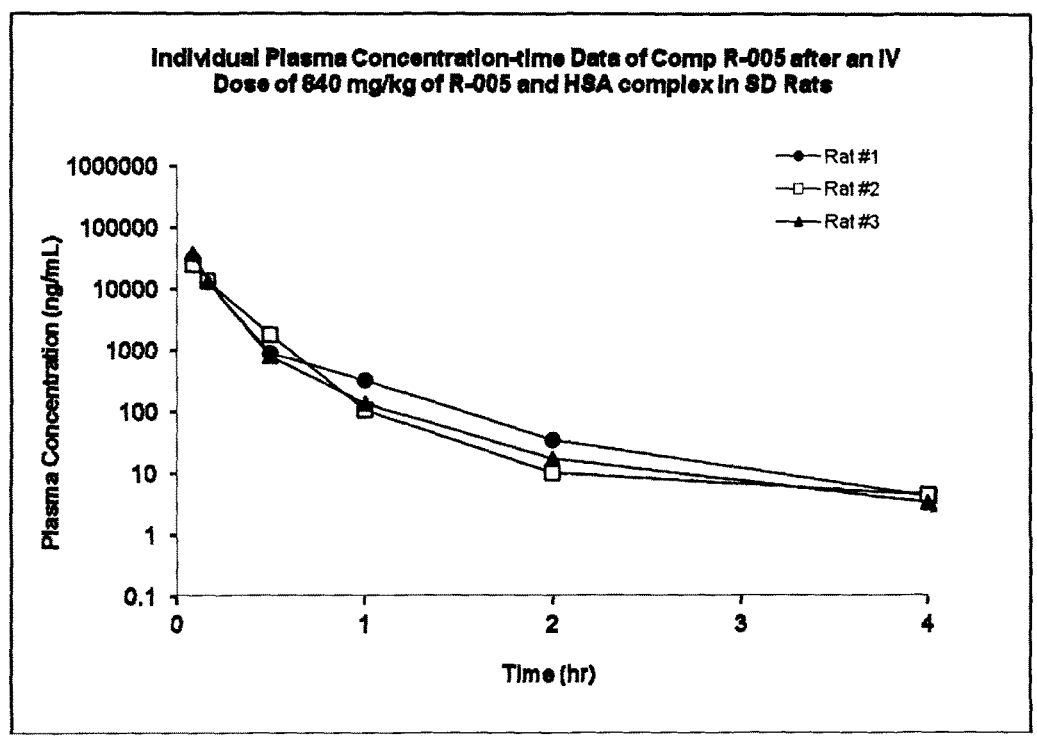
FIG. 1 contains a line plot showing individual plasma concentration-time data of compound R-005 after an IV dose of 840 mg/kg of R-005 and HSA complex in SD rats.

For the terms "for example" and "such as" and grammatical equivalences thereof, the phrase "and without limitation" is understood to follow unless explicitly stated otherwise. As used herein, the term "about" is meant to account for variations due to experimental error. All measurements reported herein are understood to be modified by the term "about", whether or not the term is explicitly used, unless explicitly stated otherwise. As used herein, the singular forms "a," "an," and "the" include plural referents unless the context clearly dictates otherwise.

As used herein, chemical structures which contain one or more stereocenters depicted with dashed and bold bonds (i.e., ⫶ and ▎) are meant to indicate absolute stereochemistry of the stereocenter(s) present in the chemical structure. As used herein, bonds symbolized by a simple line do not indicate a stereo-preference. Unless otherwise indicated to the contrary, chemical structures, which include one or more stereocenters, illustrated herein without indicating absolute or relative stereochemistry encompass all possible stereoisomeric forms of the compound (e.g., diastereomers, enantiomers) and mixtures thereof. Structures with a single bold or dashed line, and at least one additional simple line, encompass a single enantiomeric series of all possible diastereomers.

Compounds provided herein can also include all isotopes of atoms occurring in the intermediates or final compounds. Isotopes include those atoms having the same atomic number but different mass numbers. For example, isotopes of hydrogen include hydrogen, tritium, and deuterium.

The term, "compound", as used herein is meant to include all stereoisomers, geometric isomers, tautomers, and isotopes of the structures depicted. Compounds herein identified by name or structure as one particular tautomeric form are intended to include other tautomeric forms unless otherwise specified.

All compounds, and pharmaceutically acceptable salts thereof, can be found together with other substances such as water and solvents (e.g., hydrates and solvates).

The term "halo" refers to fluoro, chloro, bromo or iodo.

The term "alkyl" refers to a straight or branched chain alkyl group, having from 1-20 carbon atoms. Illustrative of the alkyl group include the methyl, ethyl, propyl, isopropyl, butyl, isobutyl, sec-butyl, t-butyl, pentyl, 3-methylbutyl, 2,2-dimethylpropyl, 1,1-dimethylpropyl, hexyl, 1-methylpentyl, 4-methylpentyl, heptyl, 1-methylhexyl, 2-methylhexyl, 5-methylhexyl, 3-ethylpentyl, octyl, 2-methylheptyl, 6-methylheptyl, 2-ethylhexyl, 2-ethyl-3-methylpentyl, 3-ethyl-2-methylpentyl, nonyl, 2-methyloctyl, 7-methyloctyl, 4-ethylheptyl, 3-ethyl-2-methylhexyl, 2-ethyl-1-methylhexyl, decyl, 2-methylnonyl, 8-methylnonyl, 5-ethyloctyl, 3-ethyl-2-methylheptyl, 3,3-diethylhexyl, undecyl, 2-methyldecyl, 9-methyldecyl, 4-ethylnonyl, 3,5-dimethylnonyl, 3-propyloctyl, 5-ethyl-4-methyloctyl, 1-pentylhexyl, dodecyl, 1-methylundecyl, 10-methylundecyl, 3-ethyldecyl, 5-propylnonyl, 3,5-diethyloctyl, tridecyl, 11-methyldodecyl, 7-ethylundecyl, 4-propyldecyl, 5-ethyl-3-methyldecyl, 3-pentyloctyl, tetradecyl, 12-methyltridecyl, 8-ethyldodecyl, 6-propylundecyl, 4-butyldecyl, 2-pentylnonyl, pentadecyl, 13-methyltetradecyl, 10-ethyltridecyl, 7-propyldodecyl, 5-ethyl-3-methyldodecyl, 4-pentyldecyl, 1-hexylnonyl, hexadecyl, 14-methylpentadecyl, 6-ethyltetradecyl, 4-propyltridecyl, 2-butyldodecyl, heptadecyl, 15-methylhexadecyl, 7-ethylpentadecyl, 3-propyltetradecyl, 5-pentyldodecyl, octadecyl, 16-methylheptadecyl, 5-propylpentadecyl, nonadecyl, 17-methyloctadecyl, 4-ethylheptadecyl, icosyl, 18-methylnonadecyl, 3-ethyloctadecyl, henicosyl, docosinyl, tricosinyl, tetracosinyl and pentacosinyl groups.

The term "$C_{s-t}$ alkyl" refers to an alkyl group between s and t carbon atoms in size. For example, $C_{1-8}$ alkyl refers to an alkyl of 1 to 8 carbon atoms.

The term "alkaryl" represents an alkyl group substituted with an aryl group. Examples of alkaryl groups include benzyl, phenethyl, and 2-(naphthalen-1-yl)ethyl.

The term "($C_{s-t}$ alkyl)aryl" is an alkaryl group containing an alkyl group between s and t carbon atoms in size. For example, ($C_{1-6}$ alkyl)aryl refers to an alkyl of 1 to 6 carbon atoms attached to an aryl group.

The term "alkenyl" represents a straight or branched chain alkenyl group, having from 2 to 20 carbon atoms. It may have 1 or more double bonds. In some embodiments, the alkenyl group may have 2-6 double bonds. Examples of such groups include the vinyl, alkyl, 1-propenyl, isopropenyl, 2-methyl-1-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 1-octenyl, 8-nonenyl, 1-nonenyl, 1-decenyl, 9-decenyl, 8-tridecenyl, cis-8-pentadecenyl, trans-8-pentadecenyl, 8-heptadecenyl, 8-heptadecenyl, 8,11-heptadecadienyl, 8,11,14-heptadecatrienyl, 4,7,11,14-nonadecatetraenyl and 2,6-dimethyl-8-(2,6,6-trimethyl-1-cyclohexen-1-yl)-1,3,5,7-nonatetraen-1-yl, cis-10-nonadecaenyl, 10,13-nonadecadienyl, cis-7,10,13-nonadecatrienyl, 5,8,11, 14-nonadecatetraenyl, nonadecapentaenyl, henecosatetraenyl, henecosapentaenyl, henecosahexaenyl, myristyl, and eicosyl groups.

The term "$C_{s-t}$ alkenyl" refers to an alkenyl group between s and t carbon atoms in size. For example, $C_{2-8}$ alkenyl refers to an alkenyl of 2 to 8 carbon atoms.

The term "alkynyl" represents an alkynyl group having from 2 to 20 carbon atoms, and may be a straight or branched chain group. In addition to one or more triple bonds, the alkynyl group may have one or more double bonds.

The term "$C_{s-t}$ alkynyl" refers to an alkynyl group between s and t carbon atoms in size. For example, $C_{2-8}$ alkynyl refers to an alkynyl of 2 to 8 carbon atoms.

When specifically stated, alkyl, alkenyl, or alkynyl groups may include ring structures of 3 to 8 carbon atoms.

When an alkyl, alkenyl or alkynyl group is described as a "lower alkyl", "lower alkenyl" or "lower alkynyl" group, it has a maximum of 6 carbon atoms.

When specifically stated, alkyl, alkenyl or alkynyl groups may include heteroatoms of oxygen, sulfur, nitrogen and/or silicon. Where specifically stated, alkyl, alkenyl or alkynyl groups may be substituted with halo, hydroxyl, nitro ($NO_2$), amine, amide, sulfhydryl (SH), O-lower alkyl and carboxy (COOH) groups. Illustrative examples of the alkyl group substituted with oxygen or including a heteroatom of oxygen include methoxymethyl, ethoxymethyl, propoxymethyl, n-butoxymethyl, 2-methoxyethyl, 2-ethoxyethyl, 2-propoxyethyl, 3-methoxypropyl, 3-ethoxypropyl, 3-propoxypropyl, 4-methoxybutyl, 4-propoxybutyl, dimethoxymethyl, 2,2-dimethoxyethyl, diethoxymethyl, 2,2-diethoxyethyl, dipropoxymethyl and 2,2-dipropoxyethyl groups. Illustrative examples of the alkyl group substituted with sulfur are methylthiomethyl, ethylthiomethyl, propylthiomethyl, n-butylthiomethyl, 2-methylthioethyl, 2-ethylthiolethyl, 2-propylthiolethyl, 3-methylthiopropyl, 3-ethylthiopropyl, 3-propylthiopropyl, 4-methylthiobutyl, and 4-propylthiobutyl groups. Illustrative examples of the alkyl group substituted with nitrogen are aminomethyl, dimethylaminomethyl, (N-acetyl)methylaminomethyl, diethylaminomethyl, dipropylaminomethyl, dibutylaminomethyl, dimethylaminoethyl, diethylaminoethyl, dipropylaminoethyl, and dibutylaminoethyl groups. Illustrative examples of the alkyl group substituted with silicon are trimethylsilyl, triethylsilyl, tributylsilyl, t-butyldimethylsilyl, t-butyldiethylsilyl and t-butyldiphenylsilyl.

The terms "amine" and "amino" are art-recognized and refer to both unsubstituted and substituted amines and salts thereof, e.g., a moiety that can be represented by the general formulae:

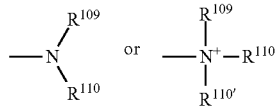

where $R^{109}$, $R^{110}$ and $R^{110'}$ each independently represent a hydrogen, an alkyl, an alkenyl, $-(CH_2)_v-R^{108}$, or $R^{109}$ and $R^{110}$ taken together with the N atom to which they are attached complete a heterocycle having from 4 to 8 atoms in the ring structure; $R^{108}$ represents an aryl, a cycloalkyl, a cycloalkenyl, a heterocyclyl or a polycyclyl; and v is zero or an integer from 1 to 8. In some embodiments, only one of $R^{109}$ or $R^{110}$ is a carbonyl, e.g., $R^{109}$, $R^{110}$, and the nitrogen together do not form an imide. In some embodiments, $R^{109}$ and $R^{110}$ (and optionally $R^{110'}$) each independently represent a hydrogen, an alkyl, an alkenyl, or $-(CH_2)_m-R^{108}$. In certain embodiments, an amino group is basic, meaning its protonated form has a $pK_a$ above 7.00.

The terms "amide" and "amido" are art-recognized as an amino-substituted carbonyl and include a moiety that can be represented by the general formula:

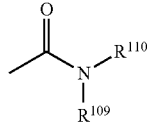

wherein $R^{109}$ and $R^{110}$ are as defined above. In some embodiments, the amide will not include imides, which may be unstable.

The term "aryl" as used herein includes 5-, 6-, and 7-membered substituted or unsubstituted single-ring aromatic groups in which each atom of the ring is carbon. The term "aryl" also includes polycyclic ring systems having two cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenol, aniline, and the like.

The terms "carbocycle" and "carbocyclyl" as used herein refer to a 3- to 6-membered non-aromatic substituted or unsubstituted ring in which each atom of the ring is carbon. The ring may be completely saturated or may have one or more unsaturated bonds such that the ring remains non-aromatic. Examples of carbocyclyls include cyclopropyl, cyclopentyl, cyclopentenyl, cyclohexyl, cyclohexenyl, and 4-methylcyclohexyl.

The term "carbocyclylalkyl" as used herein refers to a carbocyclyl group appended to an alkyl group. Examples of carbocyclyls include cyclopropylethyl, cyclopentylpropyl, cyclopentenylbutyl, and cyclohexylmethyl.

The term "oxo" refers to the functional group having a structure represented as "=O". For example, an oxo attached to a carbon is a carbonyl ("C=O"), while two oxo groups attached to a sulfur is a sulfonyl.

The terms "sulfonamide" and "sulfonamido" are art-recognized as an amino-substituted sulfonyl and include a moiety that can be represented by the general formula:

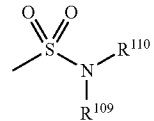

wherein $R^{109}$ and $R^{110}$ are as defined above.

The term "linker" as used herein refers to a group of atoms, e.g., 0-500 atoms, and may be comprised of the atoms or groups such as, but not limited to, carbon, amino, alkylamino, oxygen, sulfur, sulfoxide, sulfonyl, carbonyl, and imine. The linker chain may also comprise part of a saturated, unsaturated or aromatic ring, including polycyclic and heteroaromatic rings wherein the heteroaromatic ring is an aryl group containing from one to four heteroatoms, N, O or S. Specific examples include, but are not limited to, unsaturated alkanes, polyethylene glycols, and dextran polymers. The linker must not interfere with binding of the ligand to the target.

In its simplest form, a linker can be a covalent chemical bond. In some embodiments, the linker can be a chemical group. Since the function of the linking group is merely to provide a physical connection, a wide variety of chemical groups can serve as linkers. A linker is typically a divalent chemical group where one valency represents the point of attachment to a ligand or payload molecule and one valency represents the attachment to the compound. The only requirement is a stable physical linkage that is compatible with maintaining the function of the ligand or payload molecule and is compatible with the chemistry. In some embodiments, the linker comprises a —S—S— bond. Examples of suitable linkers include, e.g.: —O—, —S—, —S(O)—, —S(O)$_2$—, —S—S—, —C(O)—, —NH—, —N(C$_1$-C$_6$)alkyl, —NHC(O)—, —C(O)NH—, —O(CO)—, —C(O)O—, —O(CO)NH—, —NHC(O)O—, —O(CO)O—, —NHC(O)NH—, —O(C$_1$-C$_6$)alkylene-, —S(C$_1$-C$_6$)alkylene-, —S(O)(C$_1$-C$_6$)alkylene-, —S(O)$_2$(C$_1$-C$_6$)alkylene-, —C(O)(C$_1$-C$_6$)alkylene-, —NH((C$_1$-C$_6$)alkylene)C(O)—, —C(O)((C$_1$-C$_6$)alkylene)C(O)—, —C(O)((C$_1$-C$_6$)alkylene)NH—, —O(CO)—, —C(O)O—, —O(CO)NH—, —NHC(O)O—, —O(CO)O—, —NHC(O)NH—, unsubstituted-(C$_1$-C$_{10}$)alkylene-, unsubstituted-(C$_1$-C$_{10}$)heteroalkylene, or —(C$_1$-C$_{10}$)alkylene or —(C$_1$-C$_{10}$)heteroalkylene substituted with one or more (e.g., 1, 2, 3, 4 or 5 substituents) independently selected from the group consisting of (C$_1$-C$_6$)alkyl, (C$_2$-C$_6$)alkenyl, (C$_2$-C$_6$)alkynyl, halogen, (C$_1$-C$_6$)haloalkyl, —CN, —NO$_2$, —C(=O)R, —OC(=O)Ar, —C(=O)OR, —C(=O)NR$_2$, —C(=NR)NR$_2$, —OR, —Ar, —OAr, —((C$_1$-C$_6$)alkylene)Ar, —O((C$_1$-C$_6$)alkylene)Ar, —OC(=O)(C$_1$-C$_6$)alkyl, —OC(=O)O(C$_1$-C$_6$)alkyl, —OC(=O)NR$_2$, —NR$_2$, —NRAr, —NR((C$_1$-C$_6$)alkylene)Ar, —NRC(=O)R, —NRC(=O)Ar, —NRC(=O)O(C$_1$-C$_6$)alkyl, —NRC(=O)NR$_2$, —NRSO$_2$R, —SR, —S(O)R, —SO$_2$R, —OSO$_2$(C$_1$-C$_6$)alkyl, —SO$_2$NR$_2$, (C$_1$-C$_8$)perfluoroalkyl, —(C$_2$-C$_6$)alkylene-OR, —O(C$_2$-C$_6$)alkylene-N((C$_1$-C$_6$)alkyl)$_2$, —P(=O)(OR)$_2$, —OP(=O)(OR)$_2$, oxo and sulfido, wherein each R group is hydrogen or (C$_1$-C$_6$ alkyl), e.g., methyl and wherein each Ar is independently unsubstituted aryl or heteroaryl or aryl or heteroaryl substituted with one or more of (C$_1$-C$_6$) alkyl, (C$_2$-C$_6$)alkenyl, (C$_2$-C$_6$)alkynyl, halogen, (C$_1$-C$_6$)haloalkyl, —CN, —NO$_2$, —C(=O)R, —C(=O)OR, —C(=O)NR$_2$, —C(=NR)NR$_2$, —OR, —OC(=O)(C$_1$-C$_6$) alkyl, —OC(=O)O(C$_1$-C$_6$)alkyl, —OC(=O)NR$_2$, —NR$_2$, —NRC(=O)R, —NRC(=O)O(C$_1$-C$_6$)alkyl, —NRC(=O) NR$_2$, —NRSO$_2$R, —SR, —S(O)R, —SO$_2$R, —OSO$_2$(C$_1$-C$_6$)alkyl, —SO$_2$NR$_2$, (C$_1$-C$_8$)perfluoroalkyl, —(C$_2$-C$_6$) alkylene-OR, —O(C$_2$-C$_6$)alkylene-N((C$_1$-C$_6$)alkyl)$_2$, —P(=O)(OR)$_2$, —OP(=O)(OR)$_2$ wherein each R group is hydrogen or (C$_1$-C$_6$ alkyl). In addition, —(C$_1$-C$_{10}$)alkylene- and —(C$_1$-C$_{10}$)heteroalkylene can be substituted by one or more oxo groups (C=O) and the nitrogen and sulfur atoms of a heteroalkylene group can optionally be oxidized (e.g., to form S(O), —S(O)$_2$—, or N-oxide). Suitable heteroalkylene groups can include one or more 1,2-dioxyethylene units —(O—CH$_2$CH$_2$)$_n$O—, where n is an integer, e.g., 1, 2, 3, 4 or 5). The —(C$_1$-C$_{10}$)alkylene- and —(C$_1$-C$_{10}$)heteroalkylene also include —(C$_1$-C$_6$)alkylene- and —(C$_1$-C$_6$)heteroalkylene; and —(C$_1$-C$_3$)alkylene- and —(C$_1$-C$_3$)heteroalkylene.

The term "group of natural amino acid side chains" represents the set of chemical groups attached to the alpha carbon for each of the twenty naturally-occurring amino acids: Cysteine, Histidine, Isoleucine, Methionine, Serine, Valine, Alanine, Glycine, Leucine, Proline, Threonine, Phenylalanine, Arginine, Tyrosine, Tryptophan, Aspartic Acid, Asparagine, Glutamic Acid, Glutamine and Lysine.

As used herein, "solubility in aqueous solution of at least XX mg/ml" refers to a composition at a concentration of XX mg/ml or lower that forms an optically clear solution at room temperature in water, without need for additional, non-water, solvents.

As used herein, "substantially free of solvent", in reference to an aqueous solution, refers to an aqueous solution that contains less than 0.5%, by weight, of any non-water solvent.

As used herein, "a group that selectively binds to serum albumin" refers to a chemical group suitable for administration to a mammal, for example, a human, which exhibits binding affinity for serum albumin. Examples of such groups that selectively bind to serum albumin include, but are not limited to, long chain fatty acids (C$_{16-20}$; including oleic, palmitic, linoleic, stearic, arachidonic, and palmitoleic); medium chain fatty acids (C$_{6-14}$; including caprylate or octanoate); phospholipids (lysolecithins, oleoyllysophosphatidic acid, phosphatidylcholine, phosphatidylethanolamine); eicosanoid derivatives (leukotrienes, thromboxanes, prostaglandins A, E, F, and I); steroid hormones (cholesterol, testosterone, pregnenolone, cortisol, androsterone, indol, progesterone, estrogen); vitamin D (both monohydroxyvitamin D and dihydroxyvitamin D); bile salts (lithocholate, chenodeoxycholate, deoxycholate, ursodeoxycholate, cholate, glycolitocholate, glycochenodeoxycholate, taurochenodoxycholate, glycodeoxycholate, glycocholate, taurocholate); bilirubins (bilirubin, biliverdin, xanthobilirubin, EZ-cyclobilirubin, δ-bilirubin); porphyrins (hematin, protoporphyrin); warfarin; salicylates, ibuprofen; prednisone; iophenoxate; sulfisoxazole; phenylbutazone; oxphenylbutazone; digitoxin; indomethacin; tolbutamide; furosemide; phenyloin; chlorpropamide; chlorthiazide; the penicillins (including oxacillin, benzylpenicillin); acetotrizoate; isulfobromophthalein; deacetylcolchicine; dansylamide; dansylglutamine; dansylsarcosine; indomethacin; phenylpropazone; azobenzene derivatives; sulfobromophthalein; triiodobenzoate; benzodiazepine (including diazepam); flufenamate; iopanoate; ethacrynate; panproxen; clofibrate; L-tryptophan; N-acetyl-L-tryptophan; δ-methyl-tryptophan; thyroxine; 3,5,3'-L-triiodothyronine; indole propionate; kynurenine; ethacrynate; panproxen; chlorphenoxyisobutyrate; 3' azido-3'-deoxythymidine; non-steroidal anti-inflammatory agents containing ionized carboxyl groups; gossypol; meso-2,3-dimercaptosuccinic acid; captopril; N-2-mercaptoethyl-1,2-diaminopropane; disulfuramacetaminophen, dis-dichlorodiamineplatinum 9II; pyridoxal 5'-phosphate; aquocobalamin form of vitamin B12; folate; ascorbate (and its oxidation product dehydroascorbate); melatonin; α-melanotropin; gastrin; corticotropin; and methotrexate.

The group that selectively binds to serum albumin may bind to serum albumin at specific, defined sites, as detailed by crystallographic and displacement studies, and may also bind serum albumin at non-specific sites that have yet to be clearly defined. Binding between the group that selectively binds to serum albumin and serum albumin occurs by non-covalent mechanisms. These groups selectively bind serum albumin in that when added to mammalian blood, they bind in greatest quantity to serum albumin over other blood proteins. One of skill in the art of pharmacology is well able to envision and use a wide variety of groups that selectively bind serum albumin due to their familiarity with the literature showing many pharmaceutical compounds which preferentially bind serum albumin in mammals. See, for example, F. Kratz, et al, *Journal of Controlled Release* 2008, 132:171-183.

The phrase "pharmaceutically acceptable" is employed herein to refer to those ligands, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

A "pharmaceutically acceptable salt" includes a salt with an inorganic base, organic base, inorganic acid, organic acid, or basic or acidic amino acid. Salts of inorganic bases include, for example, alkali metals such as sodium or potassium; alkaline earth metals such as calcium and magnesium or aluminum; and ammonia. Salts of organic bases include, for example, trimethylamine, triethylamine, pyridine, picoline, ethanolamine, diethanolamine, and triethanolamine. Salts of inorganic acids include for example, hydrochloric acid, hydroboric acid, nitric acid, sulfuric acid, and phosphoric acid. Salts of organic acids include for example, formic acid, acetic acid, trifluoroacetic acid, fumaric acid, oxalic acid, tartaric acid, maleic acid, citric acid, succinic acid, malic acid, methanesulfonic acid, benzenesulfonic acid, and p-toluenesulfonic acid. Basic amino acids include, for example, arginine, lysine and ornithine. Acidic amino acids include, for example, aspartic acid and glutamic acid.

The phrase "pharmaceutically acceptable carrier" as used herein means a pharmaceutically acceptable material, composition, or vehicle, such as a liquid or solid filler, diluent, excipient, solvent or encapsulating material. As used herein the language "pharmaceutically acceptable carrier" includes buffer, sterile water for injection, solvents, dispersion media, coatings, antibacterial and antifungal agents, isotonic and absorption delaying agents, and the like, compatible with pharmaceutical administration. Each carrier must be "acceptable" in the sense of being compatible with the other ingredients of the formulation and not injurious to the subject.

As used herein, the term "cancer" refers to all known forms of cancer including, solid forms of cancer (e.g., tumors), lymphomas, and leukemias.

As used herein, a "subject" is a mammal. Exemplary mammals include mice; rats; guinea pigs; farm animals, such as goats, sheep, pigs, horses, and cows; non-human primates, such as cynomolgus monkeys, rhesus monkeys, and chimpanzees; and humans. In some embodiments, the subject is a human.

As used herein, an "effective amount" or a "pharmaceutically-effective amount" in reference to the compounds or compositions of the present disclosure refers to the amount sufficient to induce a desired biological, pharmacological, or therapeutic outcome in a subject. That result can be reduction, prevention, mitigation, delay, shortening the time to resolution of, alleviation of the signs or symptoms of, or exert a medically-beneficial effect upon the underlying pathophysiology or pathogenesis of an expected or observed side-effect, toxicity, disorder or condition, or any other desired alteration of a biological system. In cancer treatment, the result will generally include the reduction, prevention, mitigation, limitation, and/or, delay of the deleterious physiological manifestations, growth or metastases of neoplasms.

Compounds

Provided herein is a compound having a structure of Formula (I):

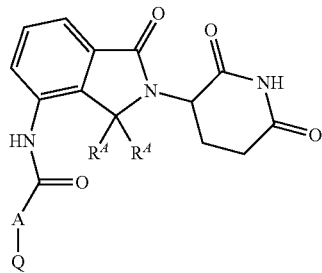

(I)

wherein
A is a covalent bond, O or NR$^1$;
each R$^A$ is H, or both R$^A$ taken together is oxo;
R$^1$ is, independently in each instance, H or lower alkyl optionally substituted with 1-3 substituents independently selected from the group consisting of: halo, nitro, amine, amide, hydroxyl, O-lower alkyl and carboxy; and
Q is a group that selectively binds to human serum albumin.

In some embodiments, R$^1$ is H or lower alkyl. For example, R$^1$ can be H.

In some embodiments, A is O.

In some embodiments, Q comprises —COOH. In some embodiments, Q comprises a —S—S— bond.

Further provided herein is a compound having the structure of Formula (II):

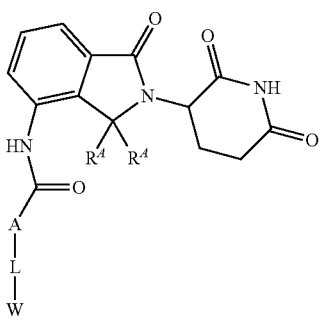

(II)

wherein
A is a covalent bond, O or NR$^1$;
each R$^A$ is H, or both R$^A$ taken together is oxo;
L is alkyl, alkyl-O-alkyl, alkenyl, alkynyl, carbocyclyl, carbocyclylalkyl, aryl, alkaryl,

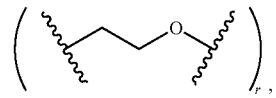

or a linker comprising a —S—S— bond, each of which is optionally substituted with 1-3 substituents independently selected from the group consisting of halo, —NO$_2$, amine, amide, hydroxyl, O-lower alkyl and —COOH, provided that there be no covalent bonds between oxygen atoms;
W is

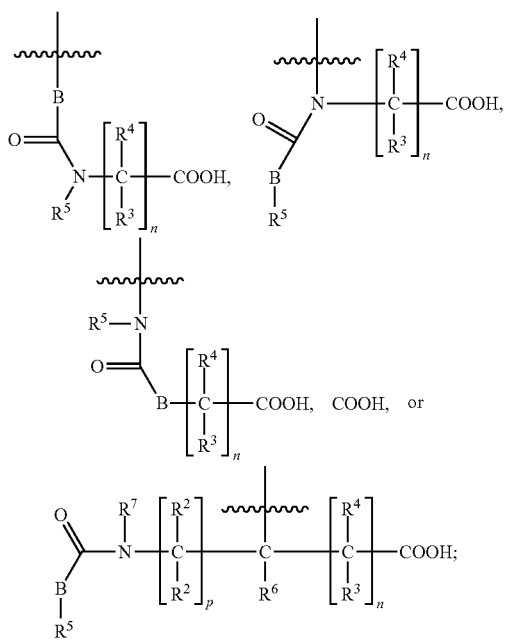

R$^1$ is H, lower alkyl, or alkaryl, wherein the alkyl or alkaryl is optionally substituted with 1-3 substituents independently selected from the group consisting of: halo, NO$_2$, amine, amide, hydroxyl, O-lower alkyl and —COOH;
R$^2$ is independently in each instance H, OH, NO$_2$, NH$_2$, SH or a branched or unbranched C$_{1-8}$ alkyl, C$_{2-8}$ alkenyl or C$_{2-8}$ alkynyl, wherein the C$_{1-8}$ alkyl, C$_{2-8}$ alkenyl or C$_{2-8}$ alkynyl is optionally substituted with 1-2 substituents independently selected from the group consisting of halo, OH, NO$_2$, NH$_2$, SH and =O, and wherein the C$_{1-8}$ alkyl, C$_{2-8}$ alkenyl or C$_{2-8}$ alkynyl optionally has 1-2 heteroatoms independently selected from O, S and NH wherein each heteroatom replaces a CH$_2$, with the proviso that no O, S or N atom in the C$_{1-8}$ alkyl, C$_{2-8}$ alkenyl or C$_{2-8}$ alkynyl is covalently bonded to another O, S or N atom;
R$^3$ is independently in each instance H, alkyl, alkenyl, alkynyl, alkyl-O-alkyl, alkyl-O-aryl, phenyl, or alkaryl, wherein the alkyl, alkenyl, alkynyl, alkyl-O-alkyl, alkyl-O-aryl, phenyl, or alkaryl is optionally substituted with 1-3 substituents independently selected from the group consisting of: halo, —NO$_2$, —CF$_3$, amido, sulfonamide, aryl, —OH, alkyl, —O-lower alkyl, —O-alkaryl, and —O-aryl;

$R^4$ is independently in each instance H, OH, $NO_2$, $NH_2$, SH or a branched or unbranched $C_{1-10}$ alkyl, $C_{2-10}$ alkenyl or $C_{2-10}$ alkynyl, wherein the $C_{1-10}$ alkyl, $C_{2-10}$ alkenyl or $C_{2-10}$ alkynyl is optionally substituted with 1-2 substituents independently selected from the group consisting of halo, OH, $NO_2$, $NH_2$, SH and =O, and wherein the $C_{1-10}$ alkyl, $C_{2-10}$ alkenyl or $C_{2-10}$ alkynyl optionally has 1-2 heteroatoms independently selected from O, S and NH wherein each heteroatom replaces a $CH_2$, with the proviso that no O, S or N atom in the $C_{1-10}$ alkyl, $C_{2-10}$ alkenyl or $C_{2-10}$ alkynyl is covalently bonded to another O, S or N atom;

$R^5$ is H, alkyl, alkenyl, alkynyl, alkyl-O-alkyl, alkyl-O-aryl, phenyl, or alkaryl, wherein the alkyl, alkenyl, alkynyl, alkyl-O-alkyl, alkyl-O-aryl, phenyl, or alkaryl is optionally substituted with 1-3 substituents independently selected from the group consisting of: halo, $-NO_2$, $-CF_3$, amido, sulfonamide, aryl, $-OH$, alkyl, $-O$-lower alkyl, $-O$-alkaryl, and $-O$-aryl;

$R^6$ and $R^7$ is each independently H or lower alkyl, optionally substituted with 1-3 substituents independently selected from the group consisting of halo, $-NO_2$, amine, amide, hydroxyl, O-lower alkyl and carboxy;

B is a covalent bond, O or $NR_1$;

p is 1, 2, 3, 4, 5, or 6;

n is 1, 2, 3, 4, 5, or 6; and r is 1, 2, 3, 4, 5, 6, 7, 8, 9, or 10.

In some embodiments, A is a covalent bond. In some embodiments, A is O or $NR^1$. In some embodiments, A is O.

In some embodiments, each $R^4$ is H. In some embodiments, both $R^4$ taken together is oxo.

In some embodiments, L is an alkyl, alkyl-O-alkyl, or alkenyl, wherein the alkyl, alkyl-O-alkyl, or alkenyl is optionally substituted with 1-3 substituents independently selected from the group consisting of halo, $-NO_2$, amine, amide, hydroxyl, O-lower alkyl and $-COOH$. In some embodiments, L is an alkyl, optionally substituted with 1-3 substituents independently selected from the group consisting of halo, $-NO_2$, amine, amide, hydroxyl, O-lower alkyl and $-COOH$. In some embodiments, L is an alkyl, optionally substituted with 1-3 substituents independently selected from the group consisting of halo, hydroxyl, O-lower alkyl and $-COOH$.

In some embodiments, L is

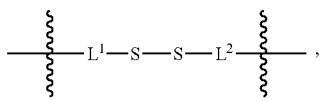

wherein $L^1$ is alkyl, alkyl-O-alkyl, alkyl-O-aryl, alkenyl, alkynyl, carbocyclyl, carbocyclylalkyl, aryl, alkaryl, or

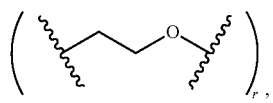

each of which is optionally substituted with 1-3 substituents independently selected from the group consisting of halo, $-NO_2$, amine, amide, hydroxyl, O-lower alkyl and $-COOH$, provided that there be no covalent bonds between oxygen atoms; $L^2$ is alkyl, alkyl-O-alkyl, alkyl-O-aryl, alkenyl, alkynyl, carbocyclyl, carbocyclylalkyl, aryl, alkaryl, or

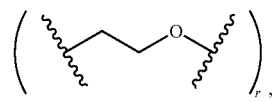

each of which is optionally substituted with 1-3 substituents independently selected from the group consisting of halo, $-NO_2$, amine, amide, hydroxyl, O-lower alkyl and $-COOH$; and each r is independently 1, 2, 3, 4, 5, 6, 7, 8, 9, or 10; provided that there be no covalent bonds between oxygen atoms.

In some embodiments, $L^1$ is an alkyl, alkyl-O-alkyl, alkyl-O-aryl, alkaryl, or aryl, wherein the alkyl, alkyl-O-alkyl, alkyl-O-aryl, alkaryl, or aryl is optionally substituted with 1-3 substituents independently selected from the group consisting of halo, $-NO_2$, amine, amide, hydroxyl, O-lower alkyl and $-COOH$. In some embodiments, $L^1$ is an alkyl, optionally substituted with 1-3 substituents independently selected from the group consisting of halo, amine, amide, hydroxyl, O-lower alkyl and $-COOH$.

In some embodiments, $L^2$ is an alkyl, alkyl-O-alkyl, alkyl-O-aryl, alkaryl, or aryl, wherein the alkyl, alkyl-O-alkyl, alkyl-O-aryl, alkaryl, or aryl is optionally substituted with 1-3 substituents independently selected from the group consisting of halo, $-NO_2$, amine, amide, hydroxyl, O-lower alkyl and $-COOH$. In some embodiments, $L^2$ is an alkyl, optionally substituted with 1-3 substituents independently selected from the group consisting of halo, amine, amide, hydroxyl, O-lower alkyl and $-COOH$.

In some embodiments, W is

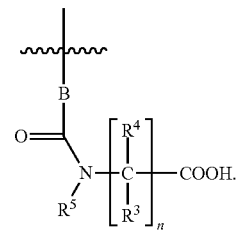

In some embodiments, W is

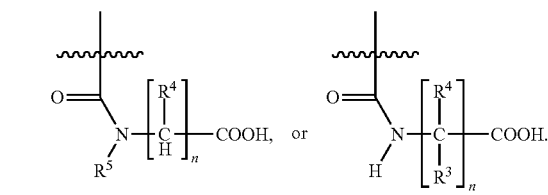

In some embodiments, $R^2$ is independently in each instance H, OH, $NO_2$, $NH_2$, SH or a branched or unbranched $C_{1-8}$ alkyl, $C_{2-8}$ alkenyl or $C_{2-8}$ alkynyl, wherein the $C_{1-8}$ alkyl, $C_{2-8}$ alkenyl or $C_{2-8}$ alkynyl is optionally substituted with 1-2 substituents independently selected from the group consisting of halo, OH, $NO_2$, $NH_2$, SH and =O. For example, $R^2$ can be H.

In some embodiments, $R^3$ is independently in each instance H, alkyl, alkyl-O-alkyl, phenyl, ($C_{1-6}$ alkyl)aryl or ($C_{1-6}$ alkyl)-O-aryl wherein the alkyl, alkyl-O-alkyl, phenyl, ($C_{1-6}$ alkyl)aryl or ($C_{1-6}$ alkyl)-O-aryl is optionally substituted with 1-3 substituents independently selected from the group consisting of: halo, —NO$_2$, amido, sulfonamide, aryl, —OH, and —O-lower alkyl. In some embodiments, R$^3$ is independently in each instance H, C$_{1-12}$ alkyl, or (C$_{1-6}$ alkyl)aryl, wherein the C$_{1-12}$ alkyl or (C$_{1-6}$ alkyl)aryl is optionally substituted with 1-3 substituents independently selected from the group consisting of: halo, —NO$_2$, amido, sulfonamide, aryl, —OH, and —O-lower alkyl. In some embodiments, R$^3$ is independently in each instance H, C$_{1-6}$ alkyl, or (C$_{1-6}$ alkyl)aryl. In some embodiments, R$^3$ can be H. In some embodiments, R$^3$ is (C$_{1-6}$ alkyl)aryl. In some embodiments, R$^3$ is benzyl. In some embodiments, R$^3$ is C$_{1-6}$ alkyl. For example, R$^3$ can be isobutyl.

In some embodiments, R$^4$ is independently in each instance H, OH, NO$_2$, NH$_2$, SH or a branched or unbranched C$_{1-8}$ alkyl, C$_{2-8}$ alkenyl or C$_{2-8}$ alkynyl, wherein the C$_{1-8}$ alkyl, C$_{2-8}$ alkenyl or C$_{2-8}$ alkynyl is optionally substituted with 1-2 substituents independently selected from the group consisting of halo, OH, NO$_2$, NH$_2$, SH and =O. For example, R$^4$ can be H.

In some embodiments, R$^5$ is H, alkyl, alkyl-O-alkyl, phenyl, (C$_{1-6}$ alkyl)aryl or (C$_{1-6}$ alkyl)-O-aryl, wherein the alkyl, alkyl-O-alkyl, phenyl, (C$_{1-6}$ alkyl)aryl or (C$_{1-6}$ alkyl)-O-aryl is optionally substituted with 1-3 substituents independently selected from the group consisting of: halo, —NO$_2$, amido, sulfonamide, aryl, —OH, and —O-lower alkyl. In some embodiments, R$^5$ is H, C$_{1-12}$ alkyl, or (C$_{1-6}$ alkyl)aryl, wherein the C$_{1-12}$ alkyl or (C$_{1-6}$ alkyl)aryl is optionally substituted with 1-2 substituents independently selected from the group consisting of: halo, —NO$_2$, amido, sulfonamide, aryl, —OH, and —O-lower alkyl. In some embodiments, R$^5$ is H, C$_{1-6}$ alkyl, or (C$_{1-3}$ alkyl)aryl. In some embodiments, R$^5$ can be H. In some embodiments, R$^5$ is (C$_{1-3}$ alkyl)aryl. For example, R$^5$ can be benzyl. In some embodiments, R$^5$ is phenethyl.

In some embodiments, R$^6$ is H or lower alkyl. For example, R$^6$ can be H.

In some embodiments, R$^7$ is H or lower alkyl. For example, R$^7$ can be H.

In some embodiments, B is a covalent bond. In some embodiments, B is O or NR$^1$. In some embodiments, B is O.

In some embodiments, n is 1, 2, 3, or 4. In some embodiments, n is 1. In some embodiments, n is 2. In some embodiments, n is 3. In some embodiments, n is 4.

In some embodiments, the compound of Formula (II) has the structure:

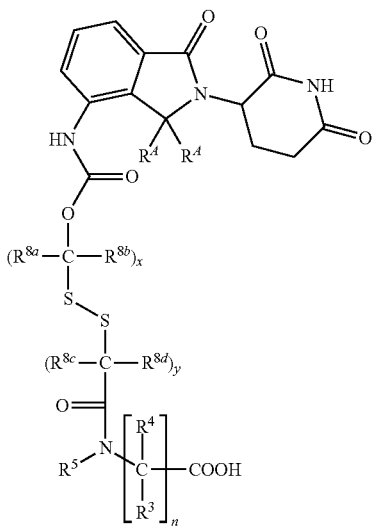

wherein
each of R$^{8a}$, R$^{8b}$, R$^{8c}$, and R$^{8d}$ is independently in each instance H or lower alkyl;
x is 1, 2, 3, 4, 5, 6, 7, or 8; and
y is 1, 2, 3, 4, 5, 6, 7, or 8.

In some embodiments, the compound of Formula (II) has the structure:

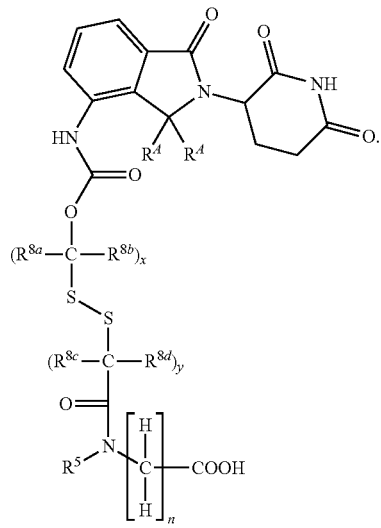

In some embodiments, the compound of Formula (II) has the structure:

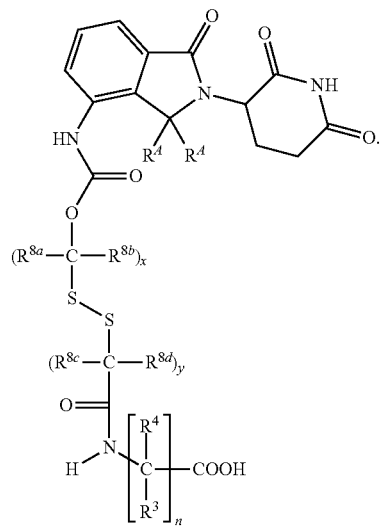

In some embodiments, n is 1, 2, 3, 4, 5, or 6. In some embodiments, n is 1, 2, 3, or 4. In some embodiments, n is 1 or 2. For example, n can be 2. In some embodiments, n is 1.

In some embodiments, x is 1, 2, 3, 4, 5, or 6. In some embodiments, x is 1, 2, or 3. For example, x can be 2.

In some embodiments, y is 1, 2, 3, 4, 5, or 6. In some embodiments, y is 1, 2, or 3. For example, y can be 2.

In some embodiments, the compound of Formula (II) is selected from:

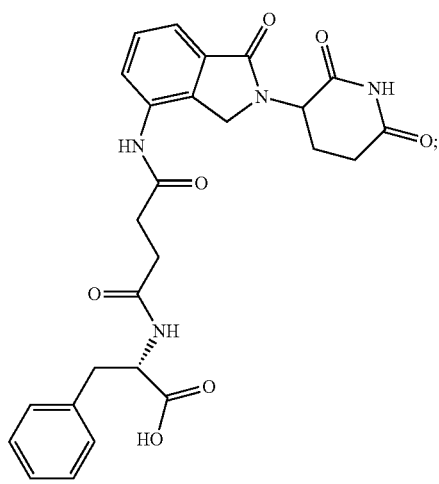
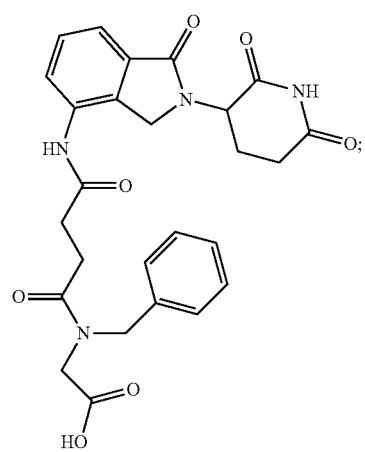
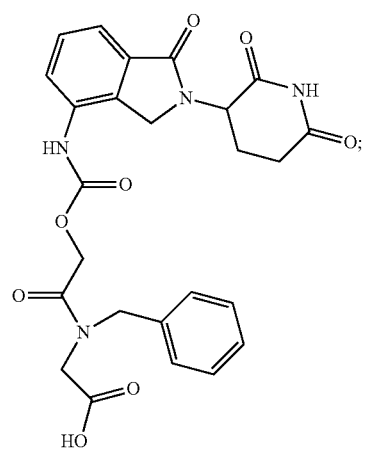
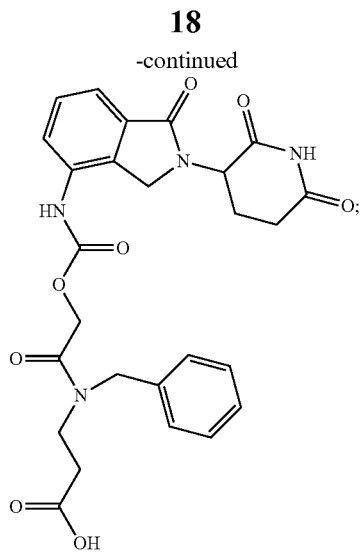
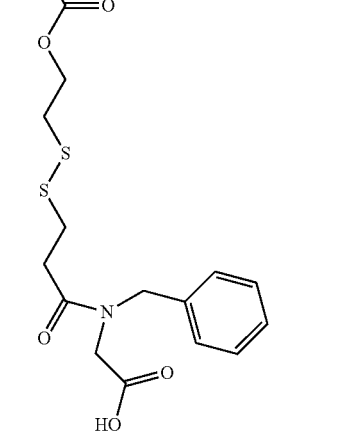
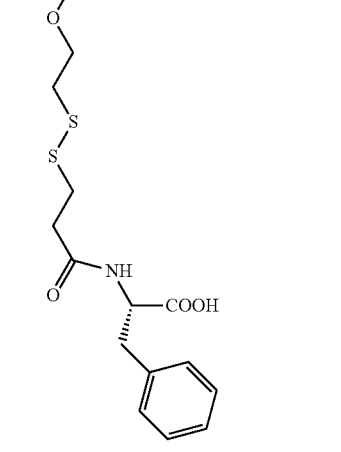

-continued
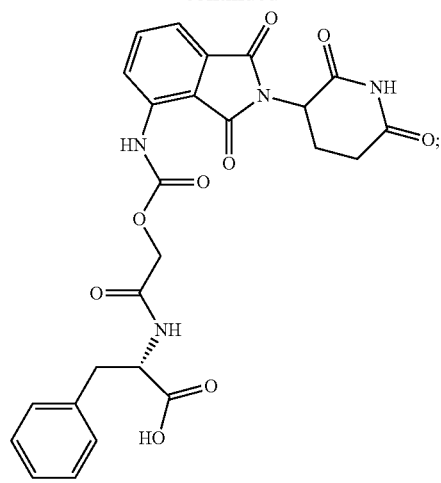
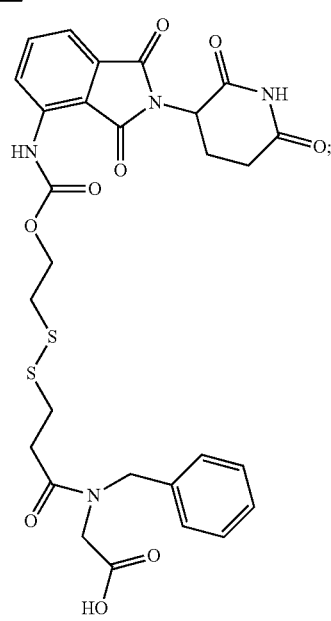
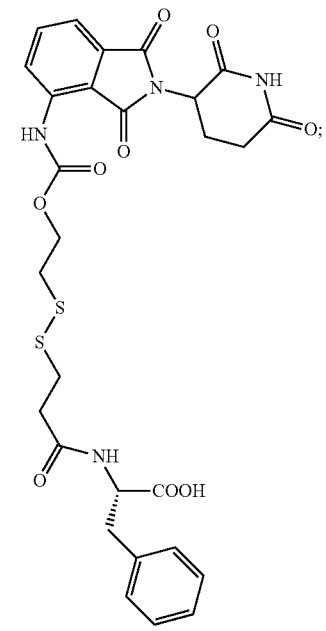
-continued
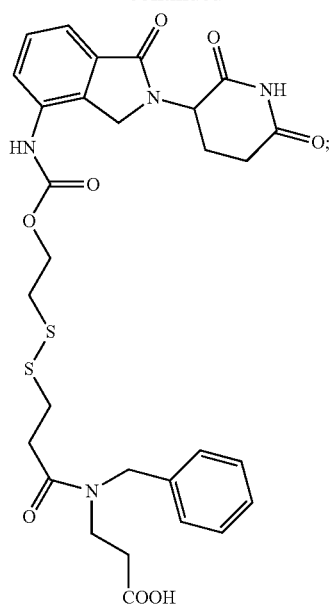
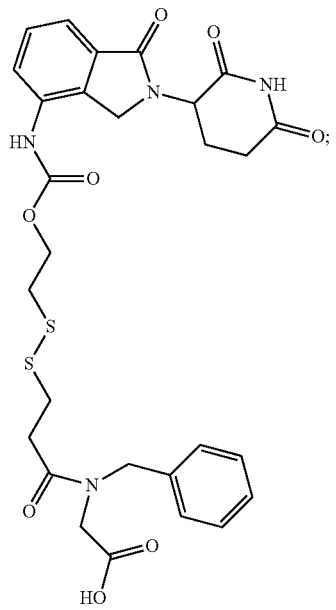

21
-continued
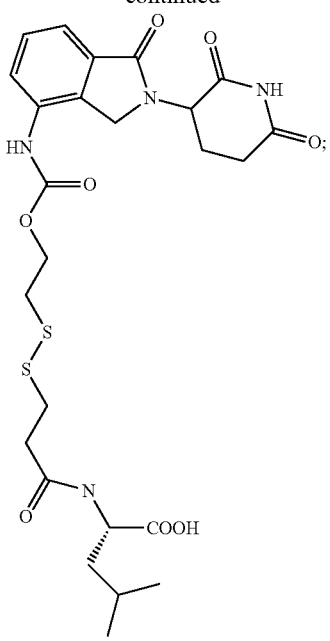
22
-continued
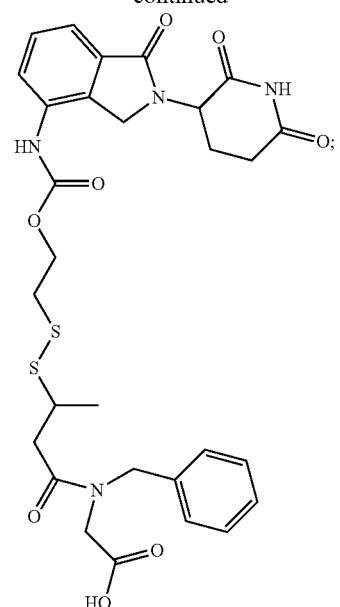
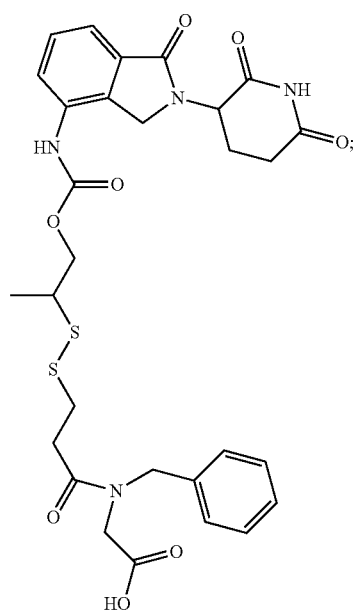
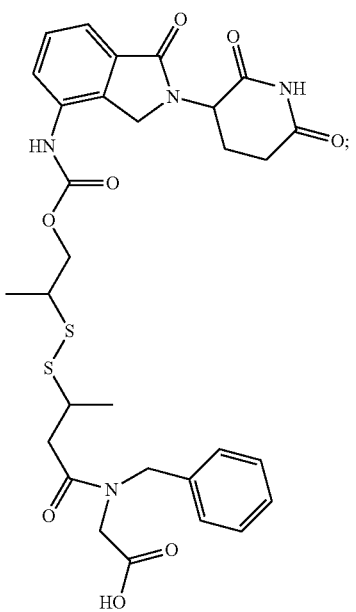

23
-continued
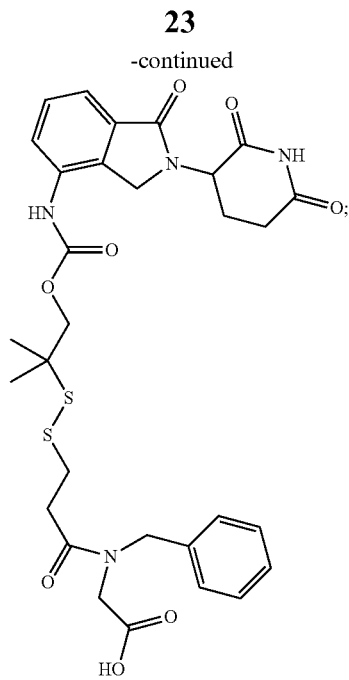
24
-continued
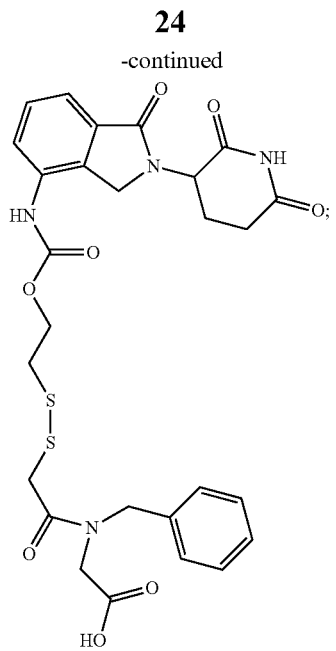
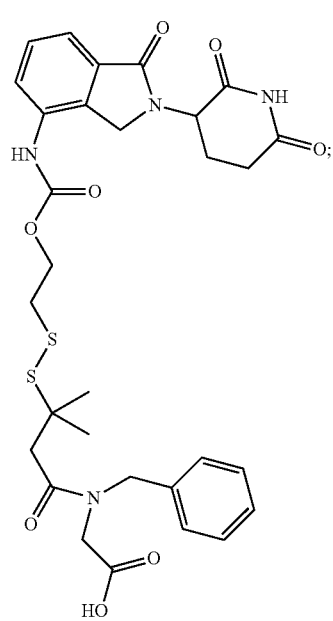

25
-continued
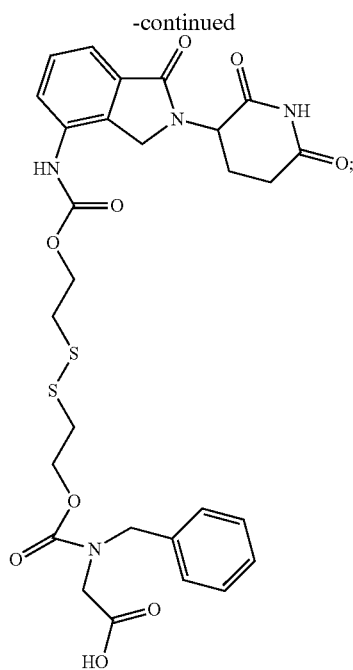
26
-continued
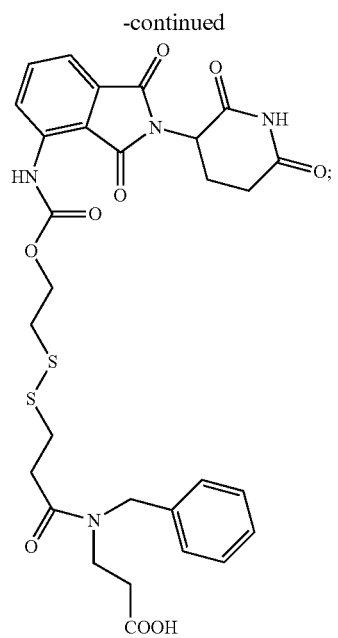
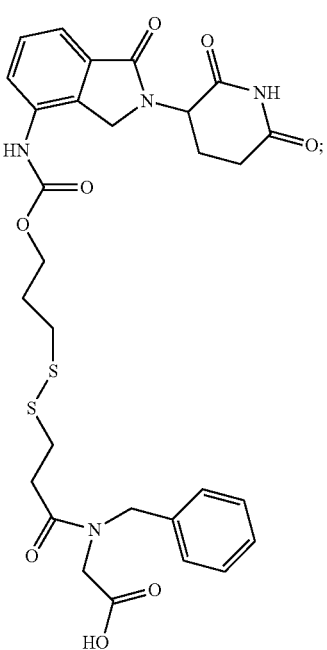
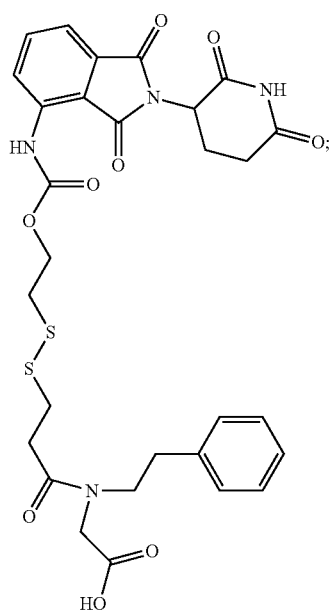

-continued
27
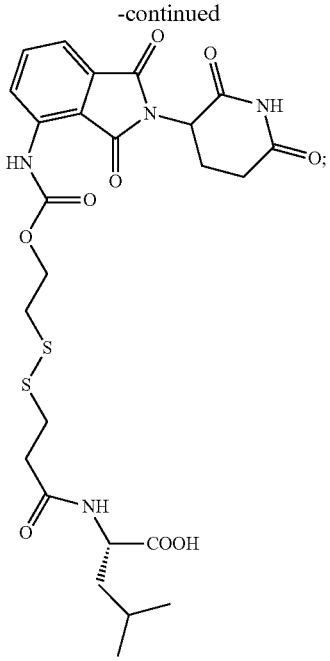
28
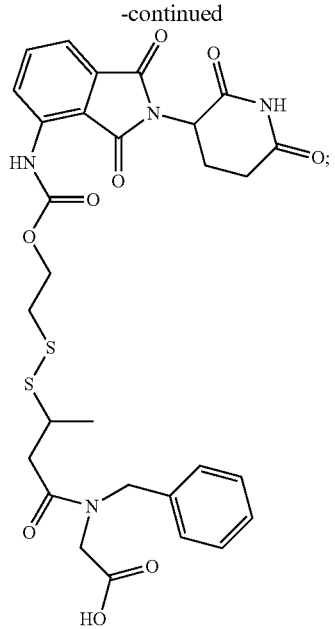
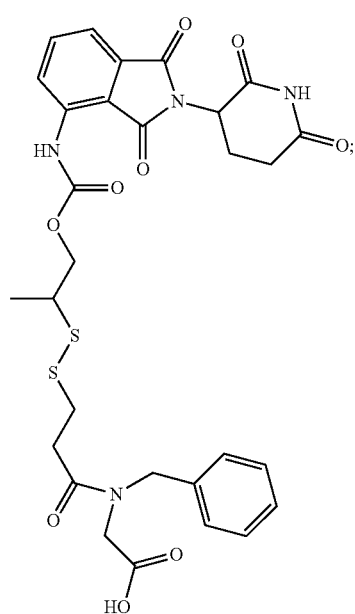
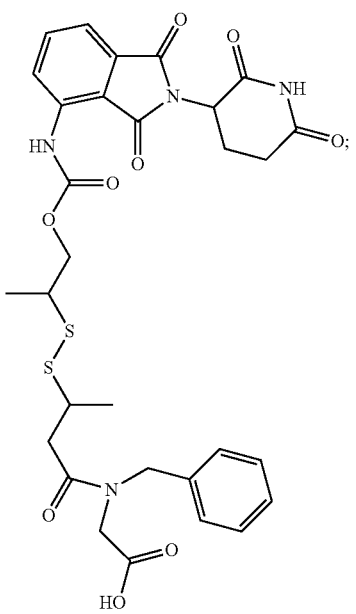

29
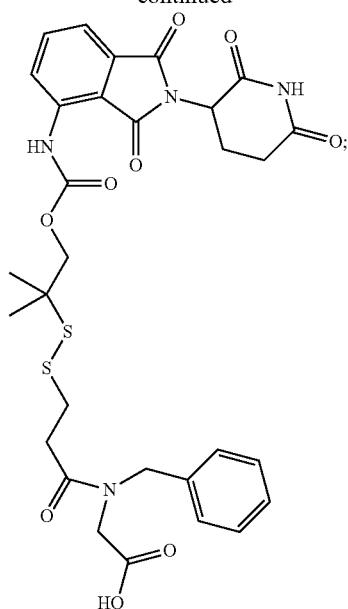
30
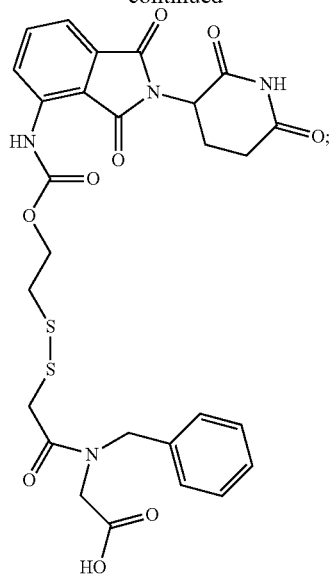
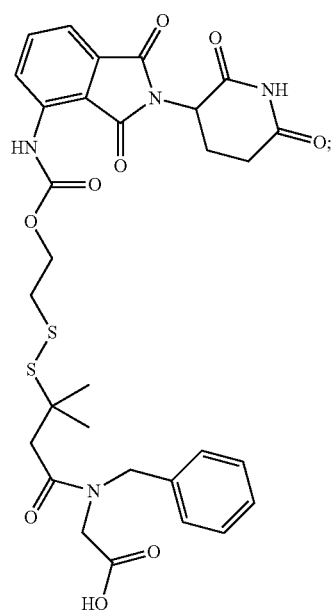
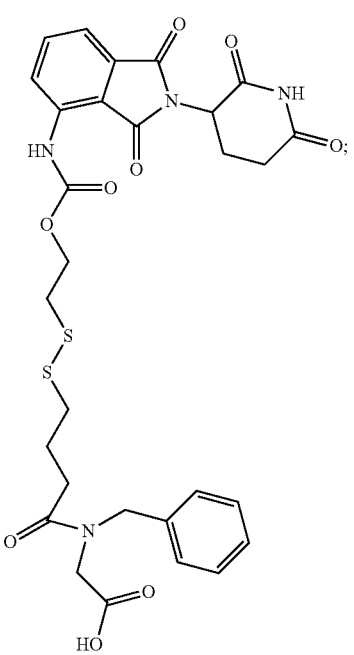

31
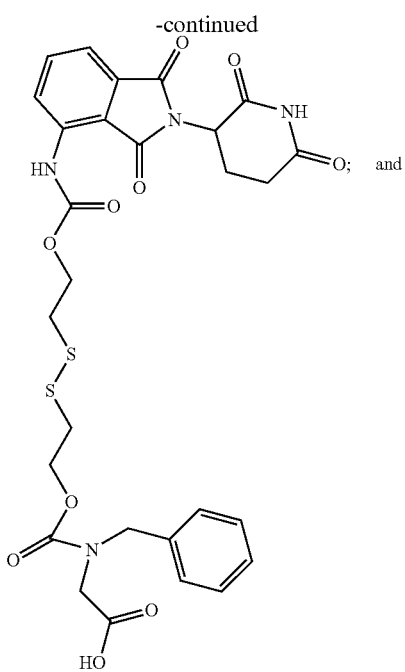
32
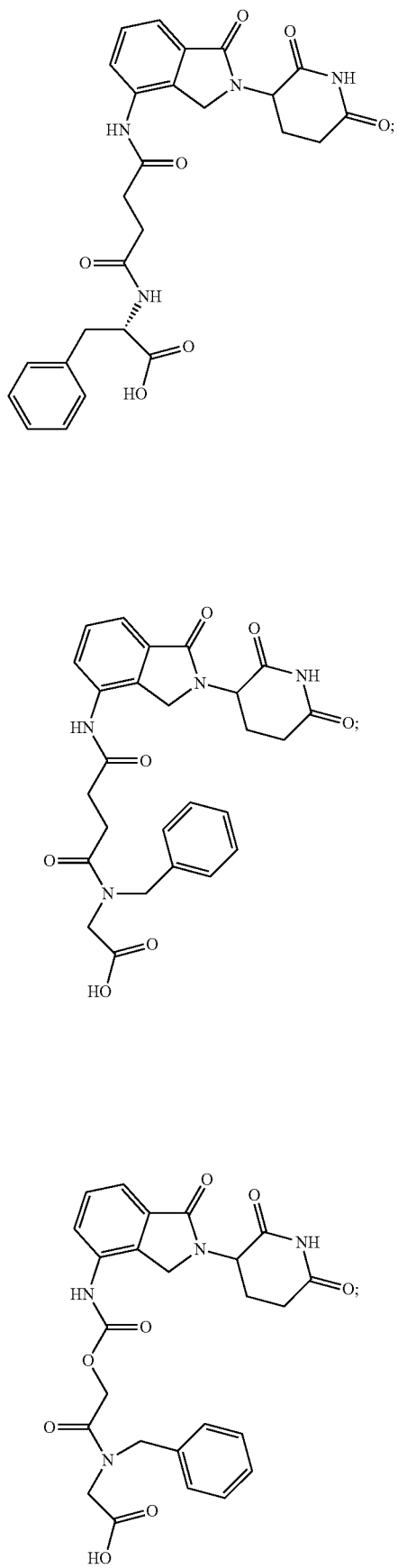
In some embodiments, the compound of Formula (II) is selected from:

33
-continued
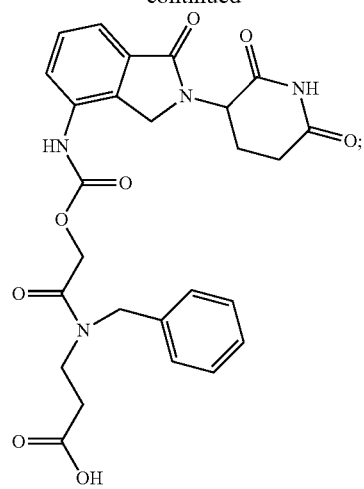
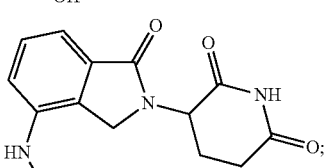
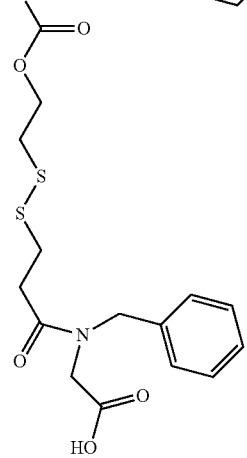
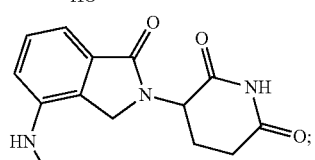
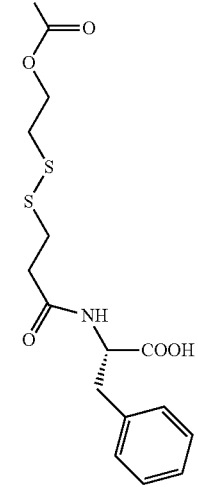
34
-continued
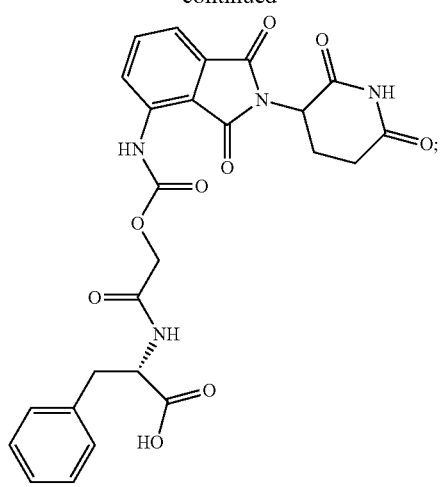
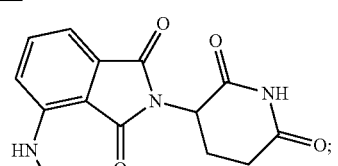
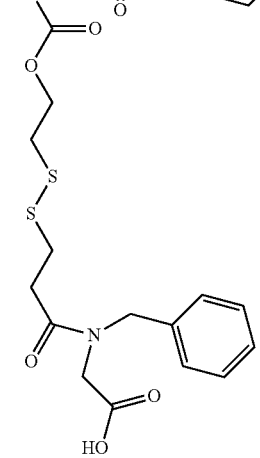
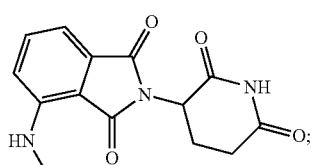
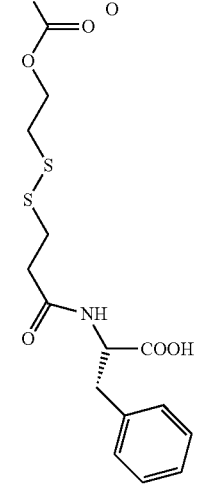

35
-continued
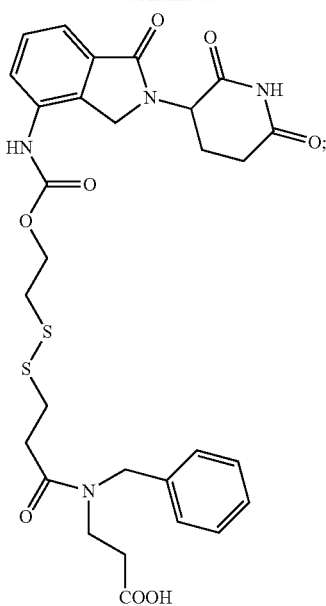
36
-continued
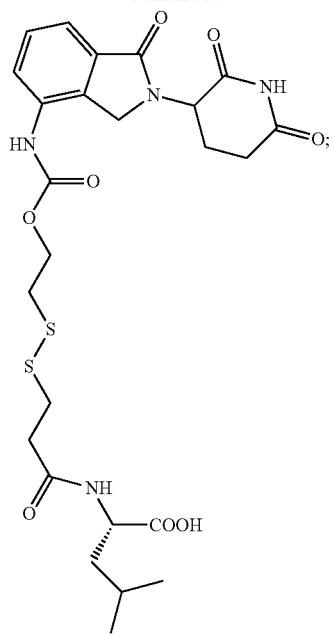
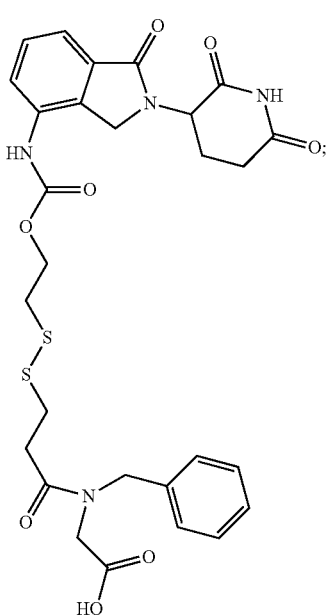
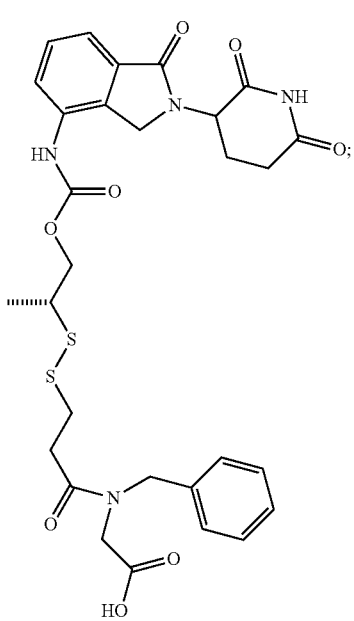

37
-continued
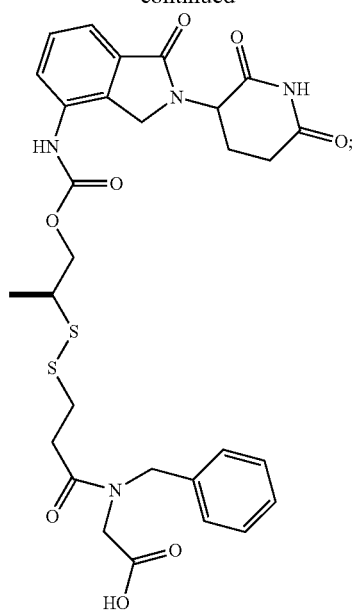
38
-continued
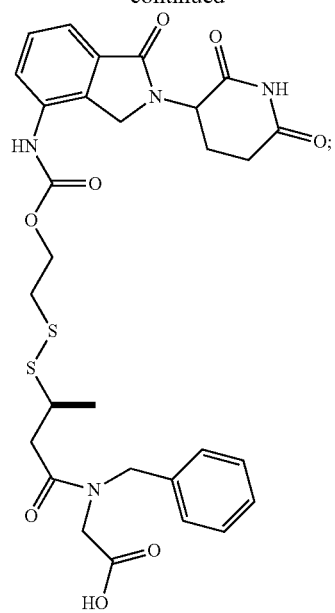

39
-continued
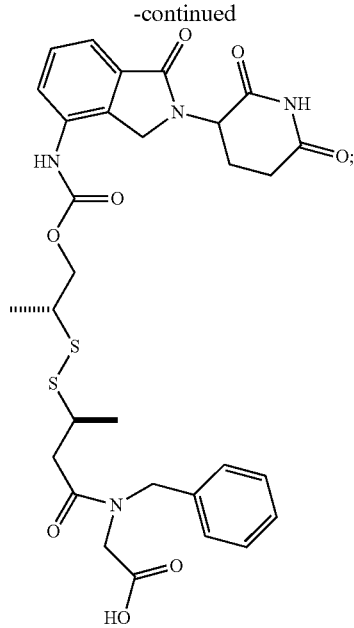
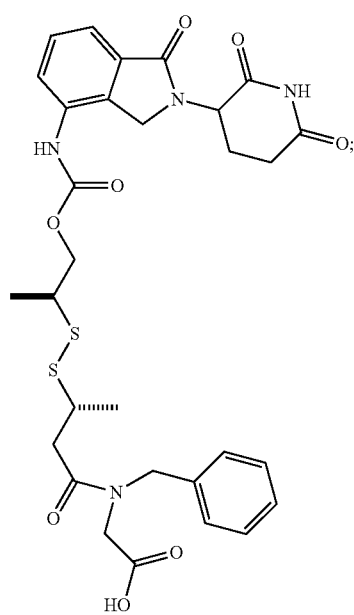
40
-continued
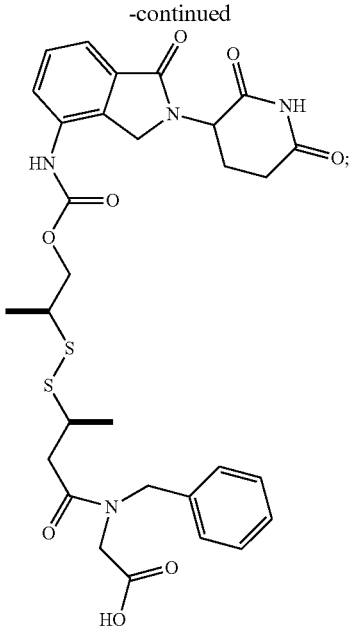

41
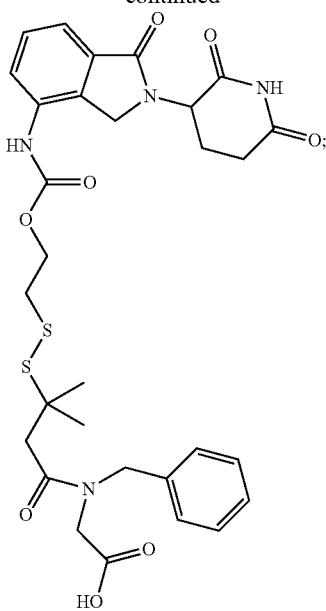
42
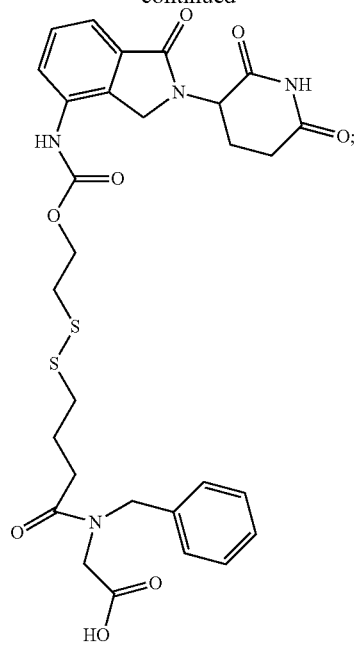
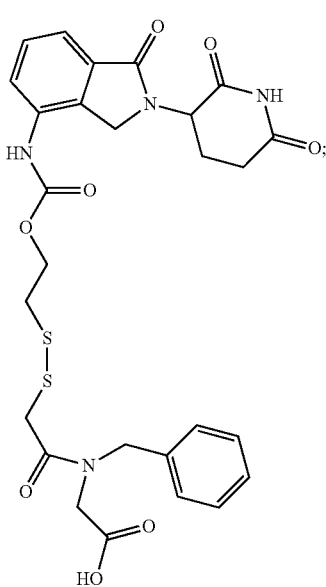
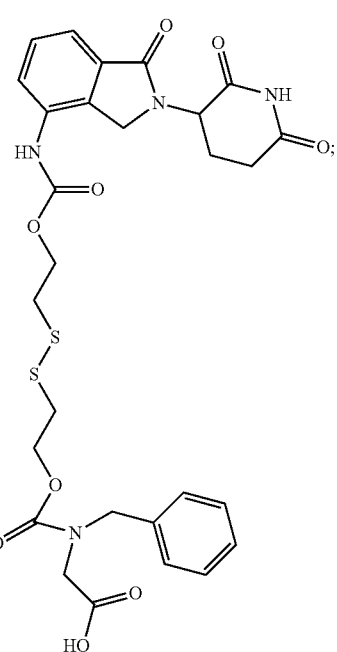

43
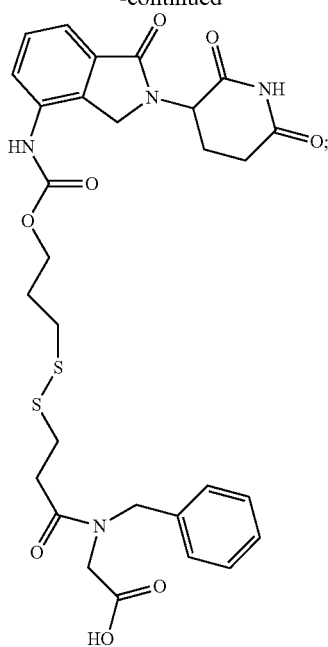
44
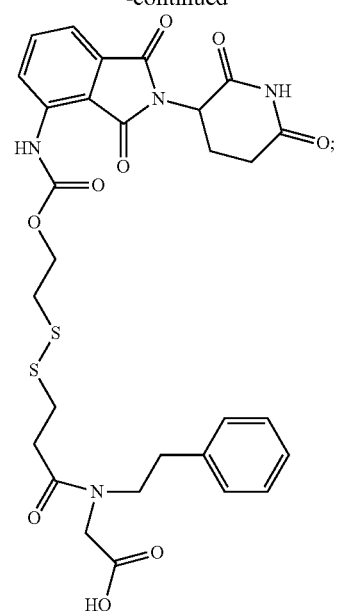
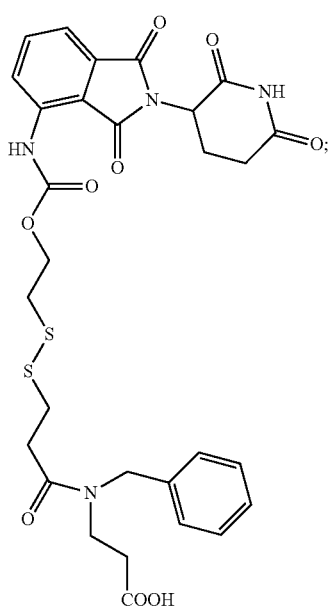
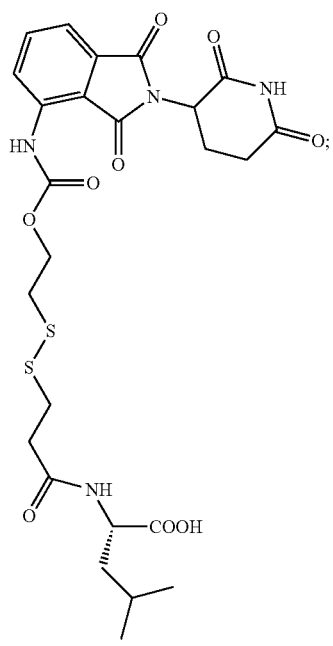

45
-continued
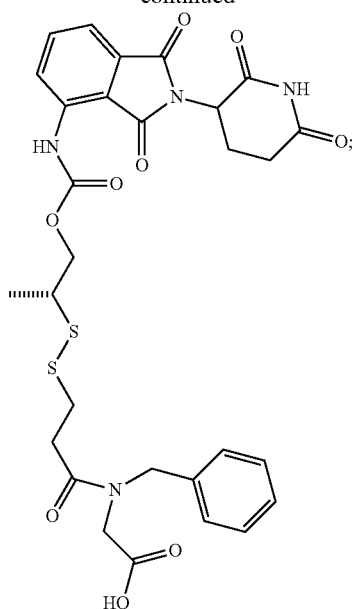
46
-continued
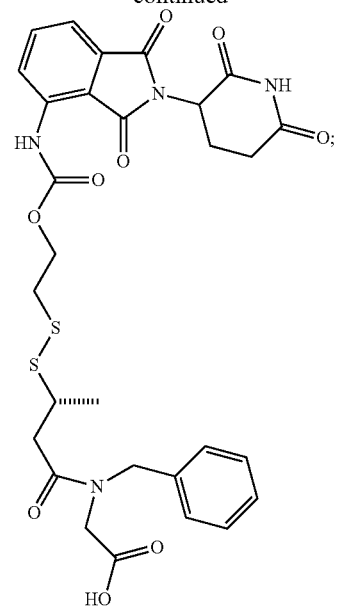
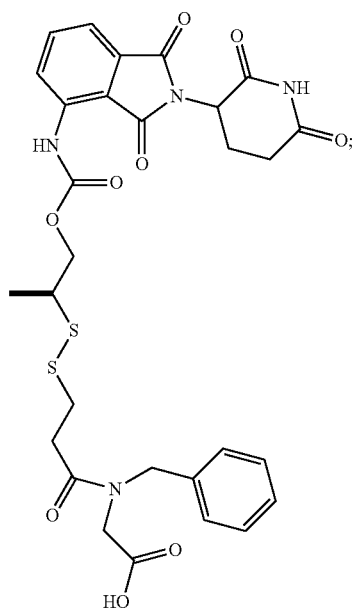
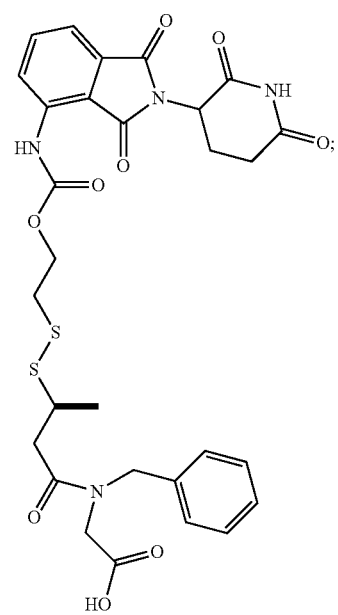

47 -continued
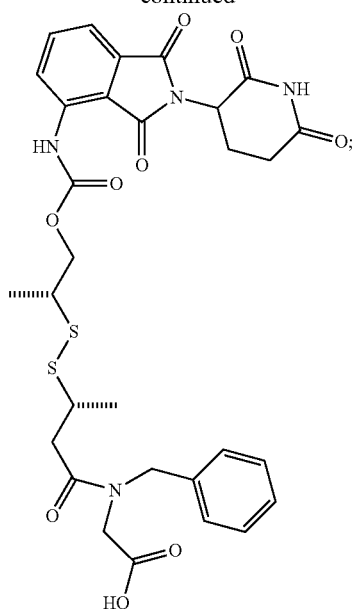
48 -continued
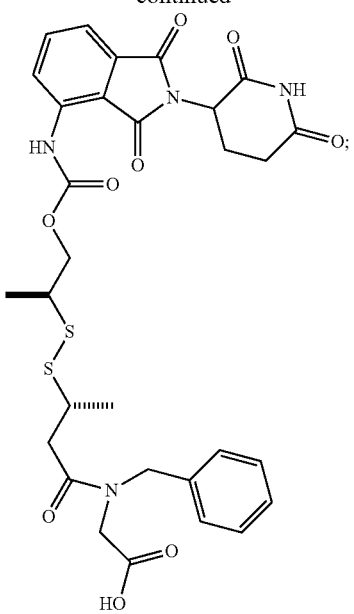

49
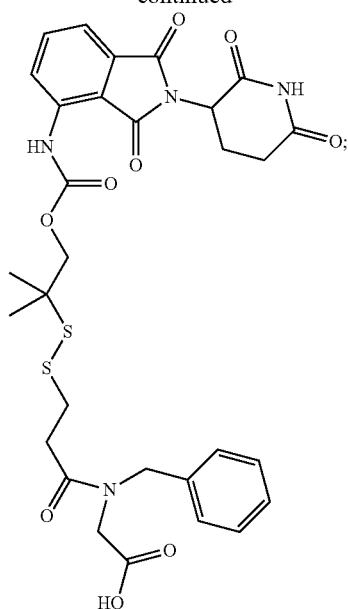
50
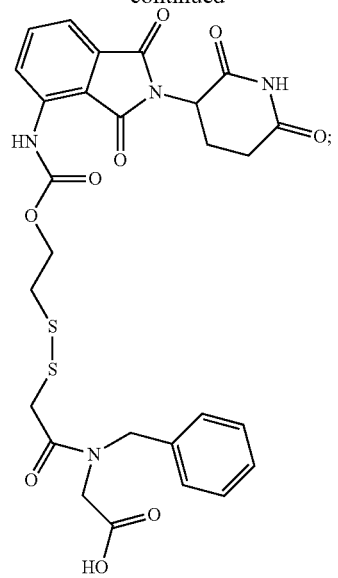
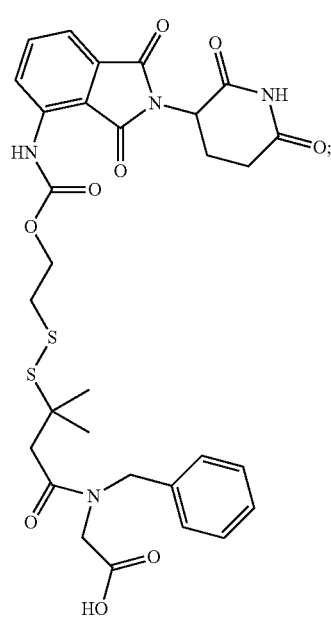
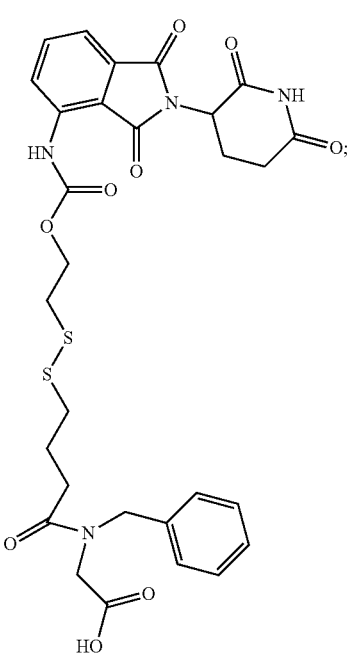

-continued

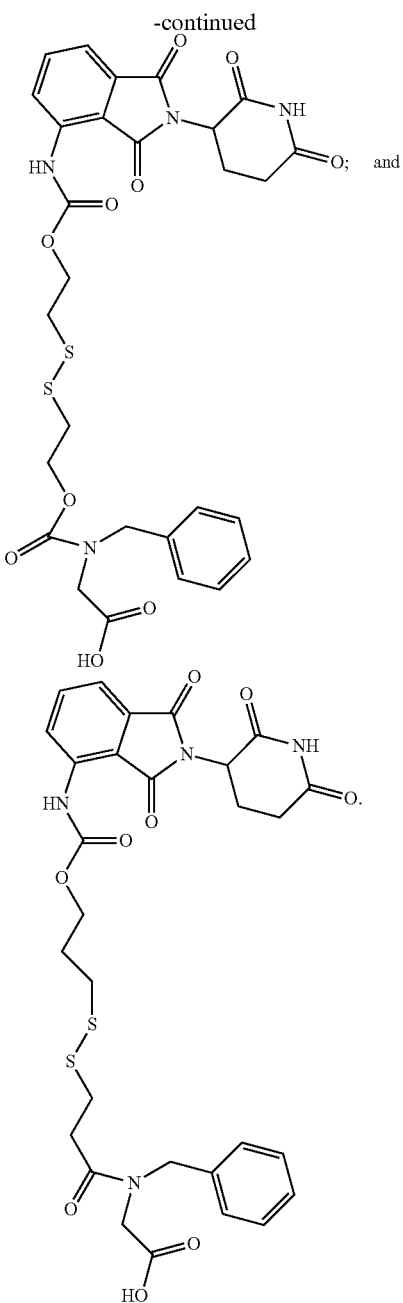

Non-Covalently Bound Complexes

An aspect of the present disclosure is directed toward non-covalently bound complexes of a lenalidomide or pomalidomide derivative as described herein, or a pharmaceutically acceptable salt thereof, and serum albumin. Upon administration, a non-covalently bound complex can dissociate to reveal the lenalidomide or pomalidomide derivative, which in turn can be cleaved by in vivo enzymes to produce the pharmaceutically active lenalidomide or pomalidomide. In some embodiments, the lenalidomide or pomalidomide derivative comprises a compound having a structure according to Formula (I) and/or Formula (II) as described herein. In some embodiments, the lenalidomide or pomalidomide derivative consists essentially of a compound having a structure according to Formula (I) and/or Formula (II). In some embodiments, the lenalidomide or pomalidomide derivative consists of a compound having a structure according to Formula (I) and/or Formula (II).

In some embodiments, the compound has a structure according to Formula (I). In some embodiments, the compound has a structure according to Formula (II) as described herein.

In some embodiments, the serum albumin is human serum albumin (HSA).

In some embodiments, the non-covalently bound complex of a compound as described herein and serum albumin has a molar ratio of compound to serum albumin in the range of from about 1:1 to about 10:1. In some embodiments, the molar ratio has a range of from about 1:1 to about 4:1, from about 2:1 to about 4:1, from about 3:1 to about 4:1, about 1:1 to about 5:1, from about 2:1 to about 5:1, from about 3:1 to about 5:1, from about 4:1 to about 5:1, from about 1:1 to about 6:1, from about 2:1 to about 6:1, from about 3:1 to about 6:1, from about 4:1 to about 6:1, from about 5:1 to about 6:1, from about 1:1 to about 7:1, from about 2:1 to about 7:1, from about 3:1 to about 7:1, from about 4:1 to about 7:1, from about 5:1 to about 7:1, from about 6:1 to about 7:1, from about 1:1 to about 8:1, from about 2:1 to about 8:1, from about 3:1 to about 8:1, from about 4:1 to about 8:1, from about 5:1 to about 8:1, from about 6:1 to about 8:1, from about 7:1 to about 8:1, from about 1:1 to about 9:1, from about 2:1 to about 9:1, from about 3:1 to about 9:1, from about 4:1 to about 9:1, from about 5:1 to about 9:1, from about 6:1 to about 9:1, from about 7:1 to about 9:1, from about 8:1 to about 9:1, from about 2:1 to about 10:1, from about 3:1 to about 10:1, from about 4:1 to about 10:1, from about 5:1 to about 10:1, from about 6:1 to about 10:1, from about 7:1 to about 10:1, from about 8:1 to about 10:1, or from about 9:1 to about 10:1. In some embodiments, the molar ratio is greater than about 2:1, 3:1, 4:1, 5:1, 6:1, 7:1, 8:1, or 9:1. In some embodiments, the molar ratio is about 2:1, about 3:1, about 4:1, about 5:1, about 6:1, about 7:1, about 8:1, or about 9:1.

In some embodiments, the non-covalently bound complex of a compound described herein and serum albumin is in a solid formulation. The solid formulation typically has been produced in a uniform manner by lyophilization. A skilled artisan would recognize other methods, such as rotary evaporation, that can also produce solid formulations.

In some embodiments, the non-covalently bound complex of a compound described herein and serum albumin is in an aqueous formulation. In some embodiments, the non-covalently bound complex of the compound and serum albumin is in an aqueous formulation substantially free of solvents other than water. In some embodiments, the non-covalently bound complex of the compound and serum albumin is in an aqueous solution that contains less than about 0.5%, 0.3%, 0.2%, 0.1%, 0.075%, 0.05%, 0.03%, 0.02%, 0.01%, 0.0075%, 0.005%, 0.003%, 0.002%, or 0.001% by weight of any non-water solvent. In some embodiments, the non-covalently bound complex of the compound and serum albumin is in an aqueous formulation free of solvents other than water.

The non-covalently bound complex of a compound described herein and serum albumin has greatly enhanced solubility compared with lenalidomide and/or pomalidomide. The non-covalently bound complex can have solubility in aqueous solution of about 5, 8, 10, 12, 14, 16, 18, 20, 22, 24, 26, 28, 30, 32, 34, 36, 38, 40, 42, 44, 46, 48, or greater than about 50 mg/mL. In some embodiments, the non-covalently bound complex has solubility in aqueous solution of 5 mg/mL or more. In some embodiments, the non-covalently bound complex has solubility in aqueous solution of 10 mg/mL or more. In some embodiments, the non-covalently bound complex has solubility in aqueous solution of 20 mg/mL or more. In some embodiments, the non-covalently bound complex has solubility in aqueous solution of 50 mg/mL or more.

In some embodiments, the non-covalently bound complex is a non-covalently bound complex of an lenalidomide and/or pomalidomide derivative and human serum albumin in a molar ratio in the range of from about 1:1 to about 10:1, wherein the non-covalently bound complex has a solubility in aqueous solution of 5 mg/mL or more, and the lenalidomide and/or pomalidomide derivative comprises a compound of Formula (I) and/or Formula (II). In some embodiments, the non-covalently bound complex is a non-covalently bound complex of an lenalidomide and/or pomalidomide derivative and human serum albumin in a molar ratio in the range of from about 1:1 to about 10:1, wherein the non-covalently bound complex has a solubility in aqueous solution of 5 mg/mL or more, and the lenalidomide and/or pomalidomide derivative consists essentially of a compound of Formula (I) and/or Formula (II). In some embodiments, the non-covalently bound complex is a non-covalently bound complex of an lenalidomide and/or pomalidomide derivative and human serum albumin in a molar ratio in the range of from about 1:1 to about 10:1, wherein the non-covalently bound complex has a solubility in aqueous solution of 5 mg/mL or more, and the lenalidomide and/or pomalidomide derivative consists of a compound of Formula (I) and/or Formula (II), or a pharmaceutically acceptable salt thereof.

Methods of Making

There are several different methods to prepare a non-covalently bound complex of the lenalidomide and/or pomalidomide derivative with serum albumin as described herein. A non-limiting example is as follows.

Formation of the Organic Solution

The lenalidomide and/or pomalidomide derivative is dissolved in a polar organic solvent (e.g., an alcohol (e.g., methanol, ethanol, isopropanol, and/or n-butanol), THF, CH$_3$CN, DMF, or mixtures thereof) to form an organic solution.

The polar organic solvent is miscible in water. In some embodiments, the polar organic solvent is an alcohol. In some embodiments, the polar organic solvent is ethanol or methanol, or mixtures thereof. For example, the polar organic solvent can be methanol. In some embodiments, the polar organic solvent is ethanol.

In some embodiments, the amount of polar organic solvent is from about 0.005 mL to about 10 mL per mg lenalidomide and/or pomalidomide derivative. In some embodiments, the amount of polar organic solvent is from about 0.05 mL to about 5 mL per mg lenalidomide and/or pomalidomide derivative. In some embodiments, the amount of polar organic solvent is from about 0.1 mL to about 2.0 mL per mg lenalidomide and/or pomalidomide derivative. In some embodiments, the amount of polar organic solvent is about 0.5 mL per mg lenalidomide and/or pomalidomide derivative.

Formation of the First Aqueous Solution

A defined amount of serum albumin is dissolved in an amount of water to form a first aqueous solution.

In some embodiments, the serum albumin is human serum albumin. The resulting non-covalently bound complex can have any molar ratio of the lenalidomide and/or pomalidomide derivative to serum albumin as described herein.

In some embodiments, the volume ratio of the amount of water to the amount of the polar organic solvent is in a range from about 1:1 to about 100:1. In some embodiments, the volume ratio of the amount of water to the amount of the polar organic solvent is in a range from about 1.5:1 to about 10:1. In some embodiments, the volume ratio of the amount of water to the amount of the polar organic solvent is in a range from about 2:1 to about 5:1. In some embodiments, the volume ratio of the amount of water to the amount of the polar organic solvent is in a range from about 2.5:1 to about 4:1. In some embodiments, the volume ratio of the amount of water to the amount of the polar organic solvent is about 2:1, about 3:1, or about 4:1.

In some embodiments, the preparation of the organic solution and the preparation of the first aqueous solution is performed concurrently.

In some embodiments, the preparation of the organic solution and the preparation of the first aqueous solution is performed sequentially. In some embodiments, the preparation of the organic solution is performed before the preparation of the first aqueous solution. In some embodiments, the preparation of the first aqueous solution is performed before the preparation of the organic solution.

Formation of the Second Aqueous Solution

The organic solution of the lenalidomide and/or pomalidomide derivative is mixed with the first aqueous solution of serum albumin to form a second aqueous solution.

In some embodiments, the organic solution is added to the first aqueous solution to form a second aqueous solution. In some embodiments, the organic solution is added dropwise to the first aqueous solution to form a second aqueous solution.

In some embodiments, the mixing is performed with agitation. In some embodiments, the mixing is performed with stirring. In some embodiments, the mixing is performed with shaking.

In some embodiments, the time of addition is in a range from about 0.1 min to about 24 hours. In some embodiments, the time of addition is in a range from about 1 min to about 2 hour. In some embodiments, the time of addition is in a range from about 5 min to about 30 min.

Removal of Organic Solvent

Upon completion of mixing of the first aqueous solution with the organic solution to form the second aqueous solution, the polar organic solvent is removed from the second aqueous solution.

In some embodiments, the polar organic solvent is removed under reduced pressure. In some embodiments, the polar organic solvent is removed using rotary evaporation. In some embodiments, the polar organic solvent is removed under a vacuum.

In some embodiments, the removal of the polar organic solvent yields a clear solution.

Removal of Water from the Second Aqueous Solution

Upon removal of the organic solvent from the second aqueous solution, the water is removed from the second aqueous solution to provide a solid.

In some embodiments, the water is removed under a vacuum. In some embodiments, the water is removed using rotary evaporation. In some embodiments, the water is removed by lyophilization.

Reconstitution of the Solid

Optionally, the solid comprising the non-covalent complex is mixed with water.

In some embodiments, the mixing is the addition of water to the solid. In some embodiments, the mixing is the addition of the solid to water. In some embodiments, the mixing reconstitutes the solid. In some embodiments, the mixing yields a clear solution.

Pharmaceutical Compositions and Administration

The methods provided herein include the manufacture and use of pharmaceutical compositions, which include one or more of the compounds provided herein. Also included are the pharmaceutical compositions themselves.

Pharmaceutical compositions typically include a pharmaceutically acceptable carrier. Some examples of materials which can serve as pharmaceutically acceptable carriers include: (1) sugars, such as lactose, glucose, and sucrose; (2) starches, such as corn starch, potato starch, and substituted or unsubstituted 3-cyclodextrin; (3) cellulose, and its derivatives, such as sodium carboxymethyl cellulose, ethyl cellulose, and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil, and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations. In certain embodiments, pharmaceutical compositions provided herein are non-pyrogenic, i.e., do not induce significant temperature elevations when administered to a subject.

Examples of pharmaceutically acceptable antioxidants include: (1) water soluble antioxidants, such as ascorbic acid, cysteine hydrochloride, sodium bisulfate, sodium metabisulfite, sodium sulfite, and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

A pharmaceutical composition may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include tonicity-adjusting agents, such as sugars and the like into the compositions. In addition, prolonged absorption of the injectable pharmaceutical form may be brought about by the inclusion of agents which delay absorption such as aluminum monostearate and gelatin.

In some cases, in order to prolong the effect of one or more compounds provided herein, it is desirable to slow the absorption of the compound from subcutaneous or intramuscular injection. For example, delayed absorption of a parenterally administered compound can be accomplished by dissolving or suspending the compound in an oil vehicle.

Combination drug therapy is the use of two or more pharmacologic agents administered either separately or in a single dose formulation. A compound, a pharmaceutically acceptable salt, or a non-covalent complex of the present disclosure may be used as a single therapy or in combination with one or more additional therapies in a method as described herein. Additional therapies include radiation or chemotherapy.

Non-limiting examples of the one or more additional therapies include administration of a corticosteroid (e.g., dexamethasone and/or prednisolone), a monoclonal antibody (e.g., alemtuzumab, rituximab, ublituximab, obinutuzumab, ipilimumab, and/or bevacizumab), a proteasome inhibitor (e.g., bortezomib, saliniosporamide A, and/or epoxomicin), an alkylating agent (e.g., carmustine, oxaliplatin, melphalan and/or cyclophosphamide), an anthracycline (e.g., epirubicin, doxorubicin, and/or daunoribicin), a nucleoside (e.g., gemcitabine, clofarabine, 5-fluorouracil and/or azacitidine), a kinase inhibitor (e.g., perifosine, marizomib, sorafenib, ibrutinib, and/or temsirolimus), a chemoprotectant (e.g., leucovorin and/or amifostine), a macrolide antibiotic (e.g., minocycline, clarithromycin, gentamycin, and/or ciprofloxacin), and a histone deacetylase inhibitor (e.g., vironostat, romidepsin, and/or panobinostat). Combinations can include, for example, a compound of Formula (I) and/or Formula (II) and rituximab; a compound of Formula (I) and/or Formula (II) and dexamethasone; a compound of Formula (I) and/or Formula (II), dexamethasone, and rituximab; a compound of Formula (I) and/or Formula (II) and azacitidine; a compound of Formula (I) and/or Formula (II) and melphalan; a compound of Formula (I) and/or Formula (II) and carmustine; a compound of Formula (I) and/or Formula (II) and epirubicin; a compound of Formula (I) and/or Formula (II) and gemcitabine; a compound of Formula (I) and/or Formula (II) and bortezomib; a compound of Formula (I) and/or Formula (II), bortezomib, and dexamethasone; a compound of Formula (I) and/or Formula (II), dexamethasone, and cyclophosphamide; and a compound of Formula (I) and/or Formula (II) and cyclophosphamide, and pharmaceutically acceptable salts and non-covalent complexes thereof.

In some embodiments, a compound of the disclosure (e.g., a compound of Formula (I) and/or Formula (II)), a pharmaceutically acceptable salt, or a non-covalent complex thereof, and the one or more additional therapies are administered concurrently. In some embodiments, the the compound, pharmaceutically acceptable salt, or non-covalent complex of the disclosure and the one or more additional therapies are admixed prior to administration.

In some embodiments, a compound of the present disclosure (e.g., a compound of Formula (I) and/or Formula (II)), a pharmaceutically acceptable salt, or a non-covalent complex thereof, and the one or more additional therapies are administered sequentially. In some embodiments, the one or more additional therapies can be administered one or more times prior to administration of the compound, pharmaceutically acceptable salt, or non-covalent complex of the disclosure (e.g., two times, three times, four times, five times, six times, ten times, 20 times). In some embodiments, the compound, pharmaceutically acceptable salt, or non-covalent complex of the disclosure can be administered one or more times prior to administration of the one or more additional therapies (e.g., two times, three times, four times, five times, six times, ten times, 20 times).

Methods of Use

The expression of pro-inflammatory cytokines, such as tumor necrosis factor-alpha (TNF-α), may be aberrant in certain inflammatory, immunological, and cancer disease states (Hideshima, T. et al. *Therapeutics and Clinical Risk Management* 2008, 4, 129-136; Kotla, V. et al. *Journal of Hematology & Oncology* 2009, 2, 36). Immunomodulatory drugs, such as lenalidomide and/or pomalidomide, can alter cytokine production, thereby affecting the health of immune cells such as T cells and NK cells. Such drugs may inhibit production of pro-inflammatory cytokines such as a tumor necrosis factor (e.g., TNF-α), and/or an interleukin (e.g., interleukin-1, interleukin-6, and/or interleukin-12), or may stimulate the proliferation of immune cells by promoting production of anti-inflammatory cytokines such as interleukin-2 (IL-2) and/or interferon-gamma (IFN-γ). In addition, complementary effects such as the inhibition of nuclear factor (NF)-κB subunit activity and/or activation of caspase-8 can contribute to their beneficial immunomodulatory actions.

An aspect of the current application is directed to a compound provided herein, a non-covalent complex of serum albumin with the compound, or a pharmaceutical composition comprising the same, that can be administered to treat a disease or condition in a subject that would benefit from inhibiting one or more cytokines selected from the group consisting of: a tumor necrosis factor (TNF), interleukin-1 (IL-1), interleukin-6 (IL-6), and interleukin-12 (IL-12). In some embodiments, the one or more cytokines is a tumor necrosis factor.

Also provided in the present disclosure is a compound as described herein, a non-covalent complex of serum albumin with the compound, or a pharmaceutical composition comprising the same, that can be administered to treat a cancer in a subject. The cancer can be newly diagnosed and have not been previously treated, or have already been treated with one or more (e.g., one, two, three, four, five, six, seven, eight, nine, 10, or 20) cancer therapies (e.g., a radiation therapy or a cancer chemotherapy).

The term "refractory" as used herein is meant to refer to a cancer that does not respond to treatment. For example, the treatment involved may be chemotherapy or radiation treatment. The cancer may be refractory at the start of treatment, or it may become refractory during treatment. In some embodiments, the methods of the disclosure are directed to treatment of a cancer that is refractory.

The term "resistant" as used herein is meant to refer to a cancer that does not respond to drug treatment. The cancer may be resistant at the start of treatment, or it may become resistant during treatment. In some embodiments, the methods of the disclosure are directed to treatment of a cancer that is resistant.

Cancer refers to disease of blood, bone, organs, skin tissue, and the vascular system, including, but not limited to, cancers of the bladder, blood, bone, brain, breast, cervix, chest, colon, endometrium, esophagus, eye, head, kidney, liver, lung, lymph nodes, mouth, neck, ovaries, pancreas, prostate, rectum, renal, skin, stomach, testis, throat, and uterus. In some embodiments, the cancer is selected from a breast cancer, a colon cancer, a leukemia, a bone cancer, a lung cancer, a bladder cancer, a brain cancer (e.g., a neuroblastoma), a bronchial cancer, a cervical cancer, a colorectal cancer, an endometrial cancer, an ependymoma, a retinoblastoma, a gallbladder cancer, a gastric cancer, a gastrointestinal cancer, a glioma, a head and neck cancer, a heart cancer, a liver cancer, a pancreatic cancer, a melanoma, a kidney cancer, a laryngeal cancer, a lip or oral cancer, a lymphoma, a mesothelioma, a mouth cancer, a myeloma, a nasopharyngeal cancer, an oropharyngeal cancer, an ovarian cancer, a thyroid cancer, a penile cancer, a pituitary cancer, a prostate cancer, a rectal cancer, a renal cancer, a salivary gland cancer, a sarcoma (e.g., Kaposi's sarcoma and soft tissue sarcoma), a skin cancer, a stomach cancer, a testicular cancer, a throat cancer, a uterine cancer, a vaginal cancer, and a vulvar cancer. In some embodiments, the cancer is selected from the group consisting of: myelodysplastic syndrome, multiple myeloma, myelofibrosis, a lymphoma (e.g., mantle cell lymphoma, follicular lymphoma, mucosa-associated lymphoid tissue lymphoma, Hodgkin's lymphoma, non-Hodgkin's lymphoma, primary central nervous system lymphoma, intraocular lymphoma, a T-cell lymphoma (e.g., angioimmunoblastic T-cell lymphoma), small lymphocytic lymphoma, and a B-cell lymphoma, for example, a non-aggressive B-cell lymphoma), a leukemia (e.g., chronic myelomonocytic leukemia, chronic lymphocytic leukemia, primary plasma cell leukemia, a T-cell leukemia, and acute myeloid leukemia), an astrocytoma, a glioma, a neuroblastoma, a hepatocellular carcinoma, a prostate cancer, a renal cell carcinoma, a melanoma, and Waldenström's macroglobulinemia.

In some embodiments, the cancer is a hematological cancer. An exemplary hematological cancer is myelodysplastic syndrome. For example, the myelodysplastic syndrome can be a low- or intermediate-1-risk myelodysplastic syndrome associated with a deletion 5q cytogenetic abnormality with or without additional cytogenetic abnormalities. In some embodiments, the myelodysplastic syndrome is relapsed. For example, the myelodysplastic syndrome can be one in which a subject has received a prior therapy (e.g., one, two, three, four, five, six, seven, eight, or nine prior therapies, with e.g., a radiation treatment or a chemotherapy). In some embodiments, the myelodysplastic syndrome is refractory. In some embodiments, the myelodysplastic syndrome is resistant.

In some embodiments, the cancer is multiple myeloma. In some embodiments, the multiple myeloma is relapsed. For example, the multiple myeloma can be one in which a subject has received a prior therapy (e.g., one, two, three, four, five, six, seven, eight, or nine prior therapies, with e.g., a radiation treatment or a chemotherapy). In some embodiments, the multiple myeloma is refractory. In some embodiments, the multiple myeloma is resistant. In some embodiments, the subject with multiple myeloma has an adverse karyotypic abnormality, e.g., a genetic deletion 17p or translocation (4;14).

In some embodiments, the cancer is mantle cell lymphoma. In some embodiments, the mantle cell lymphoma is relapsed. For example, the mantle cell lymphoma can be one in which a subject has received a prior therapy (e.g., one, two, three, four, five, six, seven, eight, or nine prior therapies, with e.g., a radiation treatment or a chemotherapy (e.g., bortezomib chemotherapy)). In some embodiments, the mantle cell lymphoma is refractory. In some embodiments, the mantle cell lymphoma is resistant.

Also provided in the present disclosure is a compound as described herein, a non-covalent complex of serum albumin with the compound, or a pharmaceutical composition comprising the same, that can be administered to treat an inflammatory disease or disorder in a subject. In some embodiments, the inflammatory disease or disorder is selected from the group consisting of: primary systemic amyloidosis, light chain deposition disease, amyloid light-chain amyloidosis, systemic scleroderma, systemic sclerosis, and graft-vs.-host disease.

EXAMPLES

Syntheses of lenalidomide and/or pomalidomide and related compounds have been reported by others. For example, U.S. Pat. No. 5,635,517 describes methods for the synthesis of lenalidomide and pomalidomide and is hereby incorporated by reference in its entirety.

Example 1: Synthesis of R-001

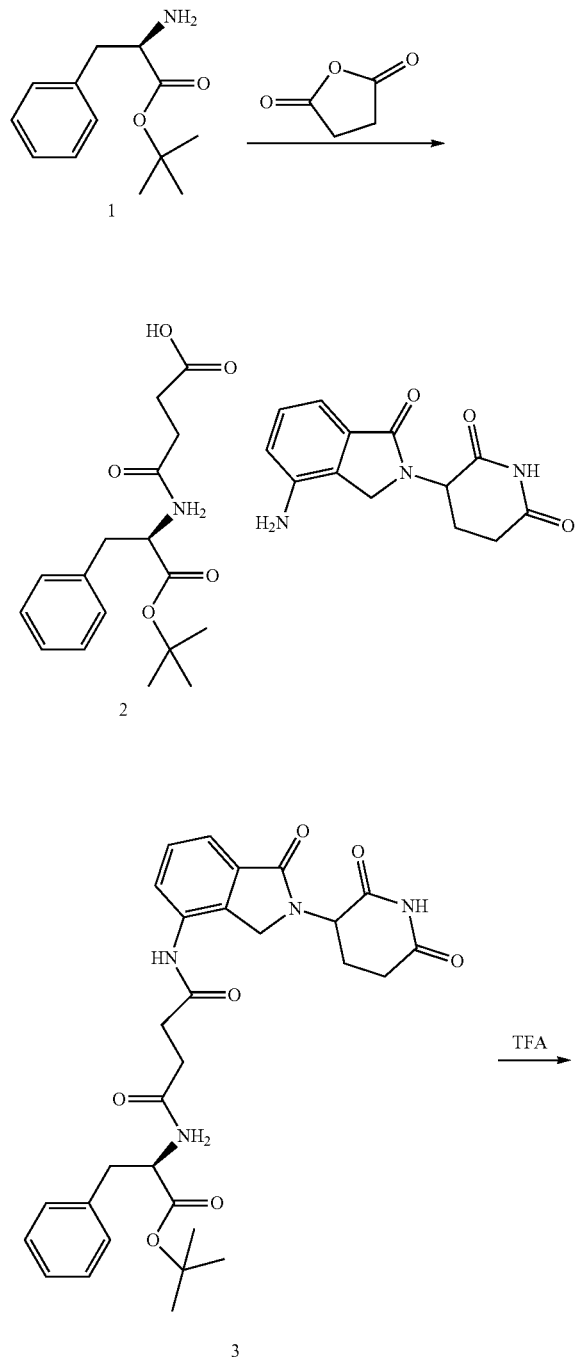

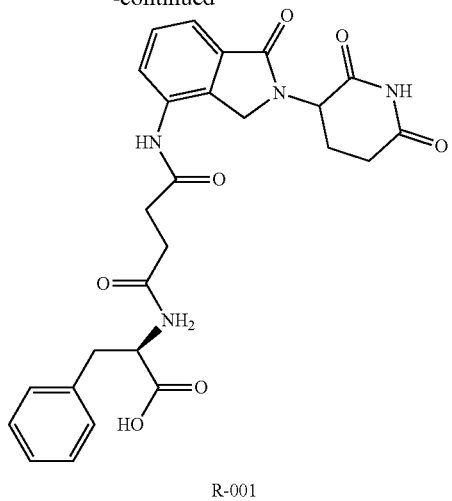

R-001

To a solution of compound 1 (2 g, 9 mmol) in pyridine (20 ml) was added dihydrofuran-2, 5-dione (1 g, 9.9 mmol). The mixture was stirred at room temperature (RT) overnight. The mixture was extracted with ethyl acetate (EA). The organic layer was washed with water and brine, dried over anhydrous $Na_2SO_4$, filtered, and concentrated to give a crude product, which was purified by a column chromatography to give compound 2 (2.5 g, 86.1%).

To a solution of compound 2 (500 mg, 1.56 mmol) in dimethylformamide (DMF) (5 ml) was added 3-(4-amino-1-oxoisoindolin-2-yl)piperidine-2,6-dione (200 mg, 0.78 mmol) and 4-dimethylaminopyridine (DMAP, 50 mg, 0.39 mmol). Then 1-ethyl-3-(3-dimethylaminopropyl)carbodiimide (EDCI, 300 mg, 1.56 mmol) was added at 0° C. The mixture was stirred at RT overnight. The mixture was extracted with EA. The organic layer was washed with water and brine, dried over anhydrous $Na_2SO_4$, filtered, and concentrated to give a crude product, which was purified by column chromatography to give compound 3 (300 mg, 34.3%); LC-MS: m/z=585.2 $(M+23)^+$ To a solution of compound 3 (0.3 g) in dichloromethane (DCM) (10 ml) was added trifluoroacetic acid (TFA) (3 ml). The mixture was stirred at RT overnight, then was concentrated. The resulting crude product was purified by a column chromatography to give R-001 (55 mg): $^1$H NMR (DMSO-$d_6$, 300 MHz) δ 10.8-10.9 (m, 1H), 9.8-9.9 (m, 1H), 7.8-7.9 (m, 1H), 7.8-7.6 (m, 4H), 7.4-7.5 (m, 1H), 7.1-7.3 (s, 5H), 5.3-5.5 (m, 3H), 5.1-5.2 (m, 1H), 4.7-4.8 (m, 1H), 4.3-4.5 (m, 1H), 3.0-3.1 (m, 2H), 2.8-2.9 (m, 2H), 2.1-2.2 (m, 2H), 1.7-1.8 (m, 1H); LC-MS: m/z=507.4 $(M+1)^+$

Example 2: Synthesis of R-002

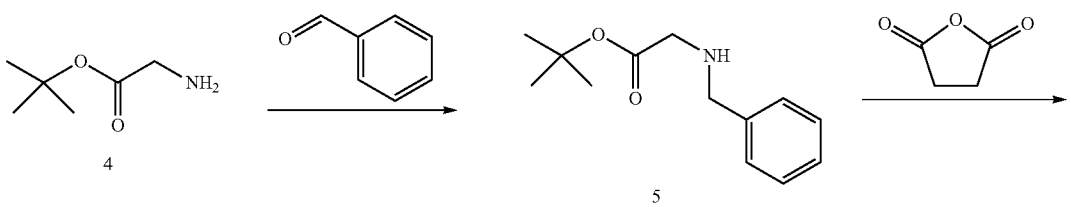

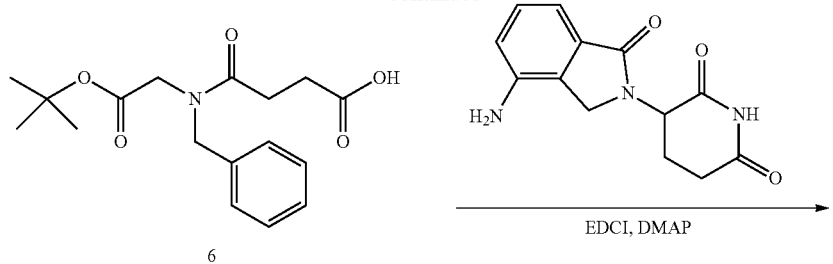

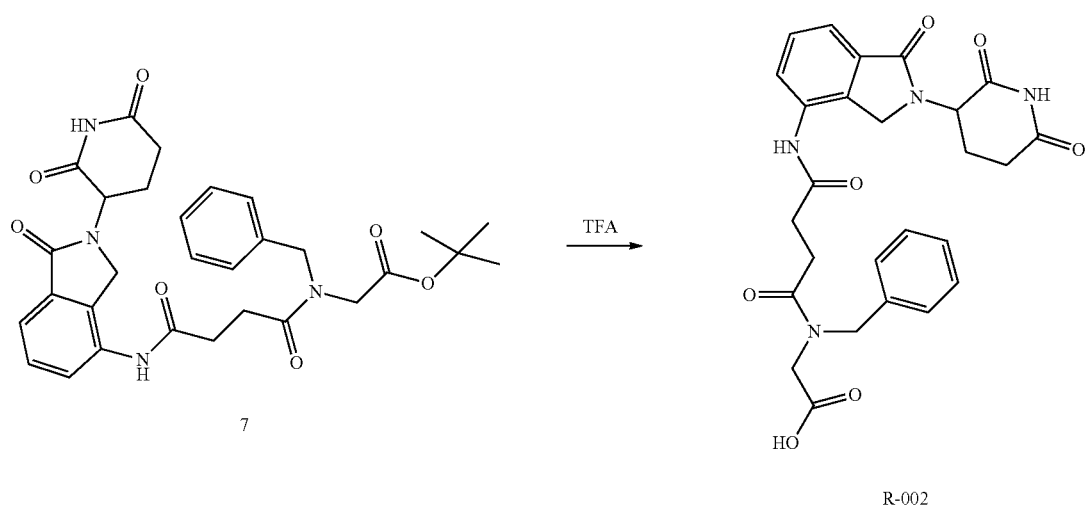

To a solution of compound 4 (500 mg, 3.8 mmol) in MeOH (20 mL) was added benzaldehyde (384 mg, 3.6 mmol). The mixture was stirred at RT for 1 hour. NaBH$_4$ (290 mg, 7.6 mmol) was added and the mixture was stirred at RT overnight. The reaction mixture was washed by water, and the organic layer was concentrated and purified by silica gel column to give compound 5 (550 mg, 65%).

To a solution of compound 5 (550 mg, 2.5 mmol) in pyridine (20 mL) was added dihydrofuran-2, 5-dione (249 mg, 2.5 mmol) under ice-bath cooling. The mixture was allowed to warm slowly to RT overnight. The reaction mixture was concentrated, and the residue purified by silica gel column to give compound 6 (650 mg, 81%).

To a solution of compound 6 (200 mg, 0.623 mmol) in DCM (20 mL) was added 3-(4-amino-1-oxoisoindolin-2-yl) piperidine-2,6-dione (161 mg, 0.623 mmol). Then EDCI (240 mg, 1.246 mmol) and DMAP (31 mg, 0.311 mmol) were added, and the mixture was stirred at RT overnight. The reaction mixture was washed by water, and the organic layer concentrated and purified by silica gel column to give 250 mg of compound 7.

To a solution of compound 7 (250 mg) in DCM (20 mL) was added TFA (5 mL) under ice-bath cooling. The mixture was stirred at RT overnight. The mixture was concentrated and the residue purified by silica gel column to give 46 mg of R-002: $^1$H NMR (300 MHz, DMSO) δ 2.0-2.4 (m, 4H), 2.5-2.9 (m, 4H), 3.9-4.1 (m, 3H), 4.4 (s, 2H), 4.7 (s, 2H), 5.1 (m, 1H), 7.1-7.4 (m, 5H), 7.6 (m, 1H), 7.9 (m, 1H); LC-MS: m/z=507.2 (M+1)$^+$ Example 3: Synthesis of R-003

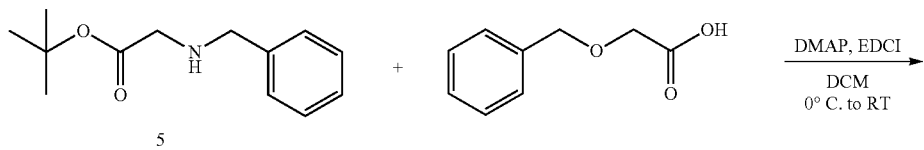

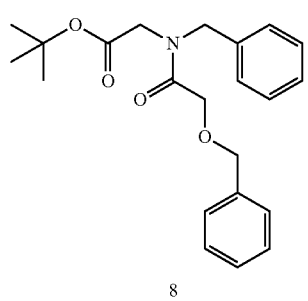

8

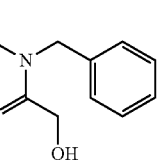

-continued

9

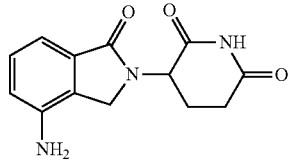

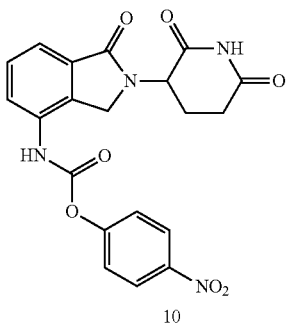

10

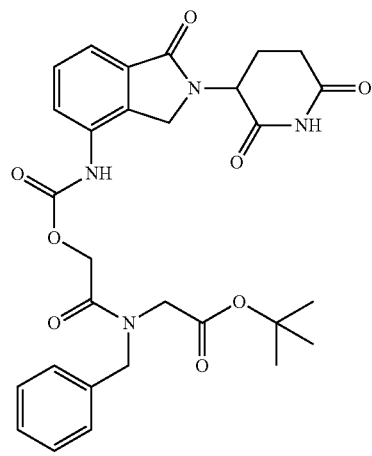

11

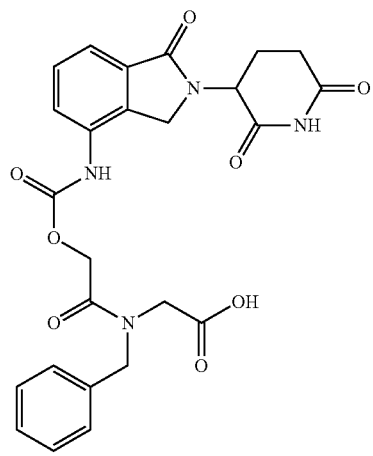

R-003

To a solution of compound 5 (500 mg, 2.26 mmol) in DCM (20 ml) was added 2-(benzyloxy)acetic acid (563 mg, 3.39 mmol) and DMAP (138 mg, 1.13 mmol). Then EDCI (650 mg, 3.39 mmol) was added at 0° C. The mixture was stirred at RT overnight. The mixture was washed with water and brine, dried over anhydrous $Na_2SO_4$, filtered, and concentrated to give a crude product, which was purified to give compound 8 (760 mg).

To a solution of compound 8 (200 mg, 0.541 mmol) in MeOH (10 ml) was added 10% Pd/C (200 mg). The mixture was stirred at RT under $H_2$ (2 MPa) overnight. The mixture was concentrated to give 143 mg of a crude oil, which was purified by column chromatography to give compound 9 (127 mg).

To a solution of 3-(4-amino-1-oxoisoindolin-2-yl)piperidine-2,6-dione (200 mg, 0.77 mmol) in dry tetrahydrofuran (THF) (20 ml) was added 4-nitrophenyl carbonochloridate (233 mg, 1.16 mmol). The mixture was stirred at reflux for 4 hours. The mixture was concentrated to 5 mL and filtered to afford compound 10 as a solid (190 mg).

To a solution of compound 9 (127 mg, 0.455 mmol) in DMF (2 ml) was added triethylamine (46 mg, 0.455 mmol) and compound 10 (161 mg, 0.379 mmol). The mixture was stirred at RT overnight. The mixture was extracted with EA, the organic layer was washed with water and brine, dried over anhydrous $Na_2SO_4$, filtered, and concentrated to give 426 mg of a crude solid. The crude residue was purified by column chromatography to give compound 11 (90 mg).

Compound 11 (90 mg) was dissolved in 10 ml of TFA/DCM (3:7). The mixture was stirred at RT overnight. The mixture was concentrated to give a crude product, which was purified by column chromatography to give R-003 (50 mg): $^1$H NMR (DMSO-$d_6$, 300 MHz) δ 10.2-10.4 (m, 1H), 9.0-9.1 (m, 1H), 7.7-7.8 (m, 1H), 7.5-7.6 (m, 1H), 7.3-7.4 (s, 5H), 7.1-7.2 (m, 2H), 5.0-5.1 (m, 1H), 4.7-4.8 (m, 1H), 4.5-4.6 (m, 1H), 4.3-4.5 (m, 1H), 3.9-4.01 (m, 1H), 3.8-3.9 (m, 1H), 2.2-2.3 (m, 2H), 2.0-2.2 (m, 2H), 1.2-1.4 (m, 2H); LC-MS: m/z=509.4 (M+1)$^+$ Example 4: Synthesis of R-004
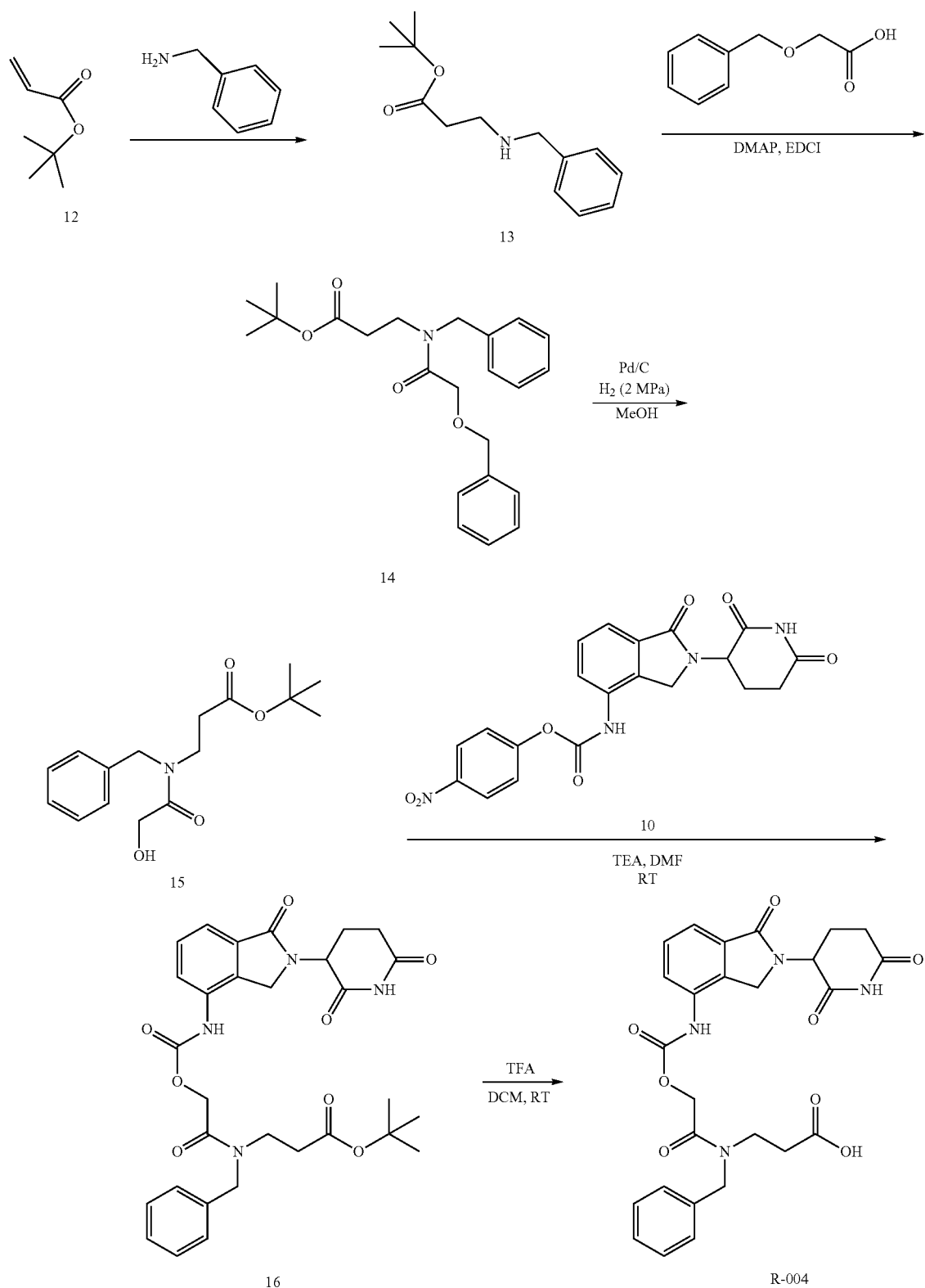
To a solution of compound 14 (2.5 g, 6.52 mmol) in MeOH (20 ml) was added 10% Pd/C (250 mg). The mixture was stirred at RT under H₂ (2 MPa) for 4 hours. Then the mixture was concentrated to give 143 mg of a crude oil, which was purified by column chromatography to give compound 15 (1.5 g).

To a solution of compound 15 (417 mg, 1.42 mmol) in DMF (5 ml) was added triethylamine (144 mg, 1.42 mmol) and 4-nitrophenyl (2-(2,6-dioxopiperidin-3-yl)-1-oxoisoindolin-4-yl)carbamate (500 mg, 1.18 mmol). The mixture was stirred at RT overnight. The mixture was extracted with EA. The organic layer was washed water and brine, dried over anhydrous Na$_2$SO$_4$, filtered, and concentrated to give 1.02 g of a crude product, which was purified by column chromatography to give compound 16 (510 mg).

Compound 16 (300 mg, 0.52 mmol) was dissolved in 10 ml of TFA/DCM (3:7). The mixture was stirred at RT overnight, and then concentrated. The crude product was purified by column chromatography to give R-004 (120 mg): $^1$H NMR (DMSO-d$_6$, 300 MHz) δ 10.6-10.74 (m, 1H), 9.3-9.4 (m, 1H), 7.8-7.9 (m, 1H), 7.5-7.6 (m, 1H), 7.4-7.5 (m, 1H), 7.2-7.4 (m, 5H), 5.1-5.2 (m, 1H), 5.0-5.1 (m, 1H), 4.8-4.9 (m, 1H), 4.6-4.7 (m, 2H), 4.4-4.6 (m, 2H), 3.5-3.7 (m, 2H), 2.8-2.9 (m, 2H), 2.6-2.7 (m, 2H), 2.3-2.4 (m, 1H), 2.1-2.2 (m, 1H); LC-MS: m/z=523.3 (M+1)$^+$ Example 5: Synthesis of R-005

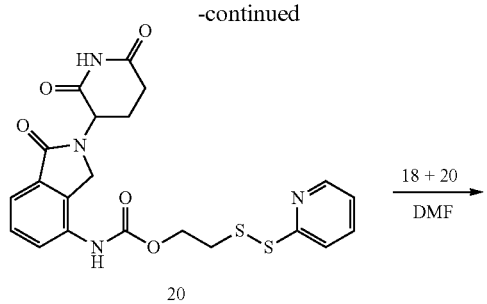

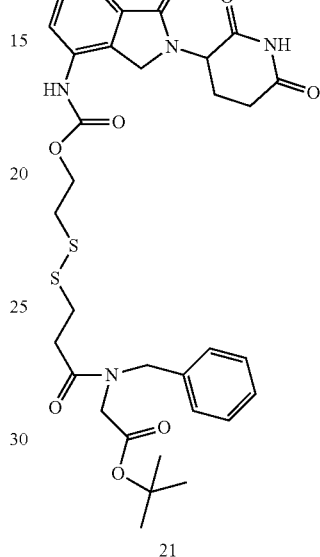

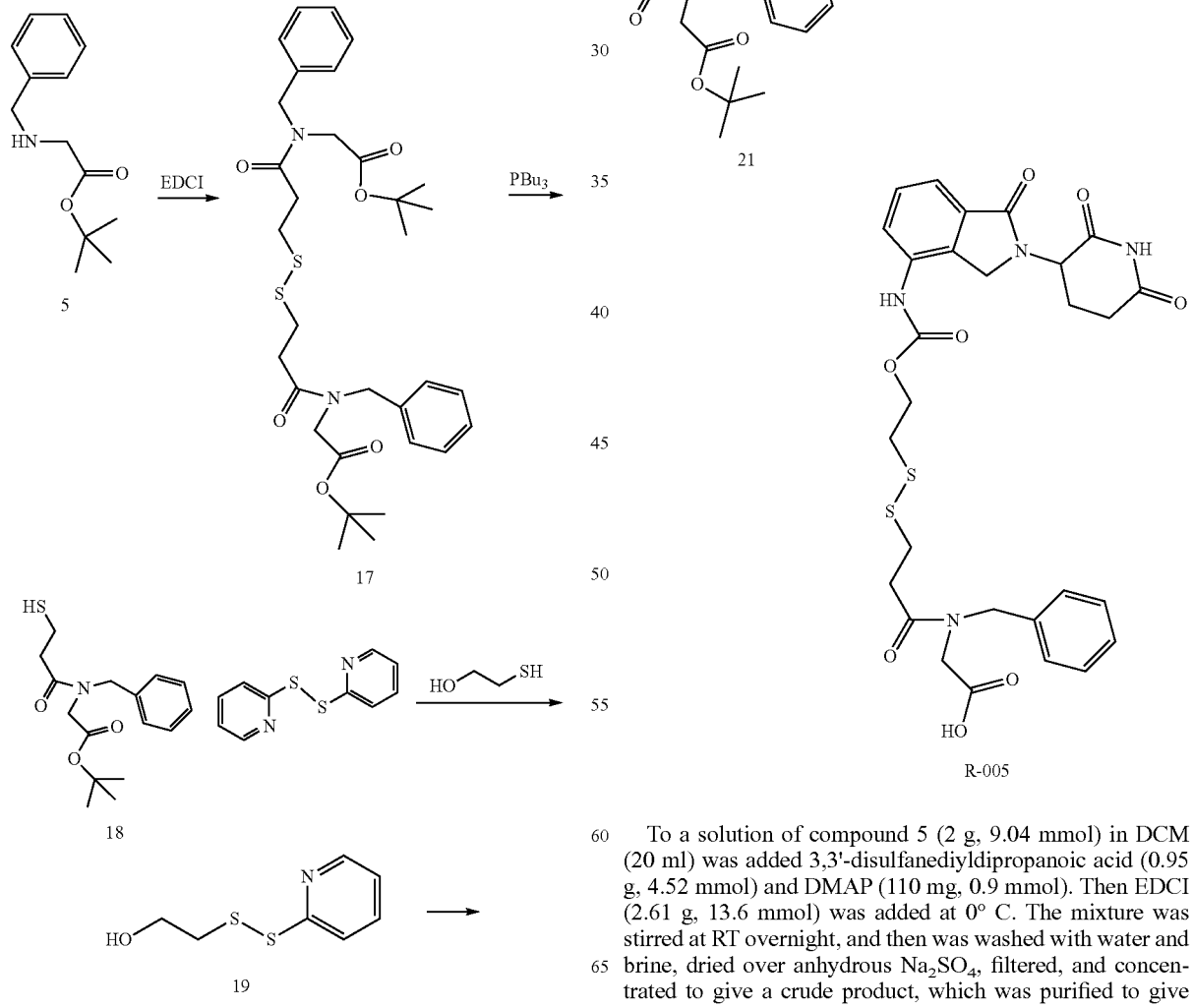

To a solution of compound 5 (2 g, 9.04 mmol) in DCM (20 ml) was added 3,3'-disulfanediyldipropanoic acid (0.95 g, 4.52 mmol) and DMAP (110 mg, 0.9 mmol). Then EDCI (2.61 g, 13.6 mmol) was added at 0° C. The mixture was stirred at RT overnight, and then was washed with water and brine, dried over anhydrous Na$_2$SO$_4$, filtered, and concentrated to give a crude product, which was purified to give compound 17 (2.1 g, 75%).

To a solution of compound 17 (500 mg, 0.81 mmol) in MeOH (3 ml) and H₂O (1.5 ml) was added PBu₃ (226 mg, 0.86 mmol), AcONa (31 mg, 0.31 mmol), and Ac₂O (25 ul). The mixture was stirred at 65° C. overnight. The mixture was extracted with EA. The organic layer was washed with water and brine, dried over anhydrous Na₂SO₄, filtered, and concentrated to give a crude product, which was purified by column chromatography to give compound 18 (190 mg, 76%).

To a solution of compound 19 (200 mg, 0.457 mmol) in DMF (5 ml) was added 4-nitrophenyl (2-(2,6-dioxopiperidin-3-yl)-1,3-dioxoiso-indolin-4-yl) carbamate (128 mg, 1 mmol). The mixture was stirred at RT overnight. The mixture was extracted with EA. The organic layer was washed with water and brine, dried over anhydrous Na₂SO₄, filtered, and concentrated to give a crude product, which was purified by column chromatography to give compound 20 (90 mg, 28%).

To a solution of compound 18 (150 mg, 0.485 mmol) in DMF (2 ml) was added compound 20 (171 mg, 0.364 mmol). The mixture was stirred at RT overnight. The mixture was extracted with EA. The organic layer was washed with water and brine, dried over anhydrous Na₂SO₄, filtered, and concentrated to give 326 mg of a crude solid, which was purified by column chromatography to give compound 21 (86 mg, 35%).

Compound 21 (86 mg) was dissolved in 10 ml of TFA/DCM (3:7). The mixture was stirred at RT overnight, and concentrated. The crude mixture was purified by a column chromatography to give R-005 (21 mg, 27%): LC-MS: m/z=615.3 (M+1)⁺

Example 6: Synthesis of R-006

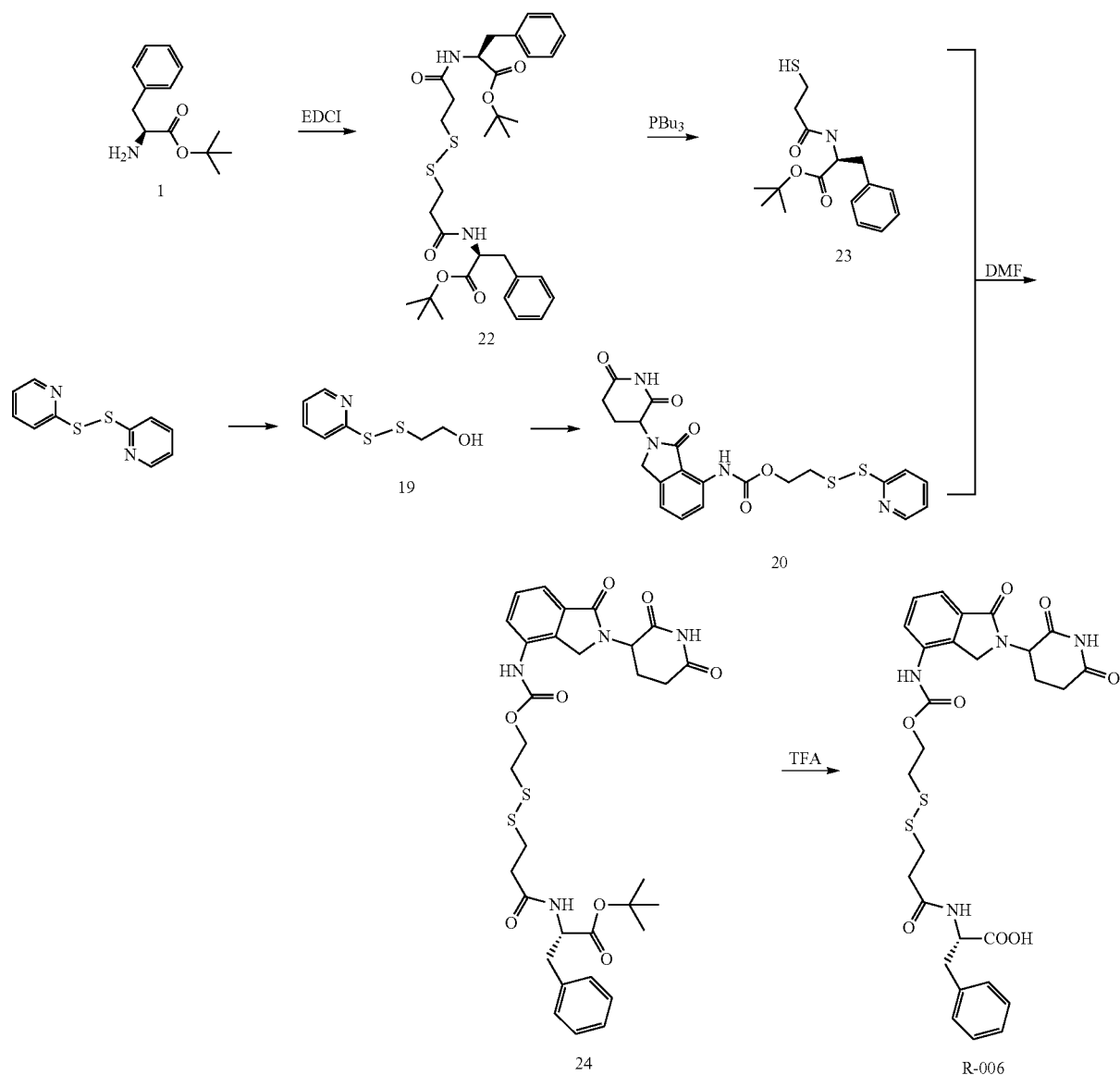

To a solution of compound 1 (2 g, 9.04 mmol) in DCM (20 ml) was added 3,3'-disulfanediyldipropanoic acid (0.95 g, 4.52 mmol) and DMAP (110 mg, 0.9 mmol). Then EDCI (2.61 g, 13.6 mmol) was added at 0° C. The mixture was stirred at RT overnight. The mixture was washed with water and brine, dried over anhydrous Na$_2$SO$_4$, filtered, and concentrated to give a crude product, which was purified to give compound 22 (2.1 g, 75%).

To a solution of compound 22 (500 mg, 0.81 mmol) in MeOH (3 ml) and H$_2$O (1.5 ml) was added PBu$_3$ (226 mg, 0.86 mmol), AcONa (31 mg, 0.31 mmol), and Ac$_2$O (25 ul). The mixture was stirred at 65° C. overnight. The mixture was extracted with EA. The organic layer was washed with water and brine, dried over anhydrous Na$_2$SO$_4$, filtered, and concentrated to give a crude product, which was purified by column chromatography to afford compound 23 (190 mg, 76%).

To a solution of compound 19 (200 mg, 0.470 mmol) in DMF (5 ml) was added 4-nitrophenyl (2-(2,6-dioxopiperidin-3-yl)-1,3-dioxoiso-indolin-4-yl)carbamate (128 mg, 1 mmol). The mixture was stirred at RT overnight. The mixture was extracted with EA. The organic layer was washed with water and brine, dried over anhydrous Na$_2$SO$_4$, filtered, and concentrated to give a crude product, which was purified by column chromatography to provide compound 20 (90 mg, 29%).

To a solution of compound 20 (90 mg, 0.186 mmol) in DMF (5 ml) was added compound 23 (85.8 mg, 0.278 mmol). The mixture was stirred at RT overnight. The mixture was extracted with EA. The organic layer was washed with water and brine, dried over anhydrous Na$_2$SO$_4$, filtered, and concentrated to give a crude product, which was purified by column chromatography to afford compound 24 (65 mg, 51%).

Compound 24 (65 mg) was dissolved in 10 ml of TFA/DCM (3:7). The mixture was stirred at RT overnight, and then was concentrated. The crude mixture was purified by column chromatography to give R-006 (28 mg, 46%): LC-MS: m/z=615.1 (M+1)

Example 7: Synthesis of P-001

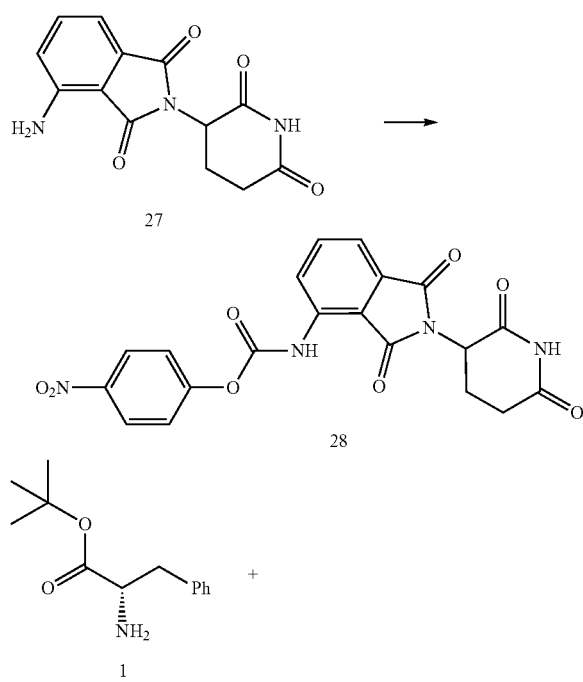

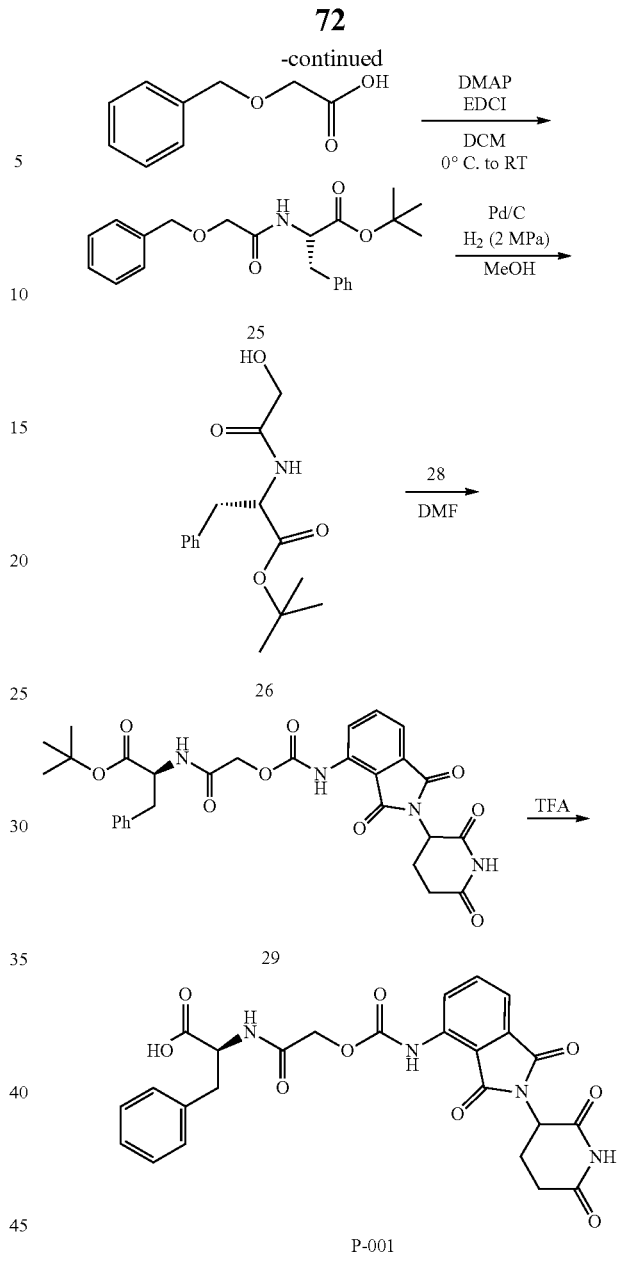

To a solution of compound 1 (500 mg, 2.26 mmol) in DCM (20 ml), was added 2-(benzyloxy)acetic acid (563 mg, 3.39 mmol) and DMAP (138 mg, 1.13 mmol). Then EDCI (650 mg, 3.39 mmol) was added at 0° C. The mixture was stirred at RT overnight. The mixture was washed with water and brine, dried over anhydrous Na$_2$SO$_4$, filtered and concentrated to give a crude product, which was purified to give compound 25 (760 mg).

To a solution of compound 25 (200 mg, 0.541 mmol) in MeOH (10 ml) was added 10% Pd/C (200 mg). The mixture was stirred at RT under H$_2$ (2 MPa) overnight, and was concentrated to give 143 mg of a crude oil, which was purified by column chromatography to give compound 26 (127 mg, 84%).

To a solution of compound 27 (200 mg, 0.70 mmol) in dry THF (20 ml) was added 4-nitrophenyl carbonochloridate (233 mg, 1.10 mmol). The mixture was stirred at reflux for 4 hours. The mixture was concentrated to 5 mL, and filtered to give compound 28 as a solid (180 mg).

To a solution of compound 25 (100 mg, 0.358 mmol) in DMF (5 ml) was added compound 28 (141 mg, 0.322 mmol). The mixture was stirred at RT overnight, and was concentrated to give a crude product, which was purified by column chromatography to give compound 29 (96 mg, 52%).

Compound 29 (96 mg, 0.455 mmol) was dissolved in DCM (10 ml), and then TFA (3 ml) was added. The mixture was stirred at RT overnight, and concentrated to give 130 mg of a crude product. The crude product was purified by column chromatography to give P-001 (50 mg, 58%): LC-MS: m/z=545.3 (M+23)$^+$ Example 8: Synthesis of P-002 stirred at RT overnight. The mixture was washed with water and brine, dried over anhydrous $Na_2SO_4$, filtered, and concentrated to give a crude product, which was purified to give compound 17 (2.1 g, 75%).

To a solution of compound 17 (500 mg, 0.81 mmol) in MeOH (3 ml) and $H_2O$ (1.5 ml) was added $PBu_3$ (226 mg, 0.86 mmol), AcONa (31 mg, 0.31 mmol) and $Ac_2O$ (25 ul). The mixture was stirred at 65° C. overnight. The mixture was extracted with EA. The organic layer was washed with water and brine, dried over anhydrous $Na_2SO_4$, filtered, and concentrated to give a crude product, which was purified by a column chromatography to give compound 18 (190 mg, 76%).

To a solution of compound 19 (200 mg, 0.457 mmol) in DMF (5 ml) was added 4-nitrophenyl (2-(2, 6-dioxopiperi-

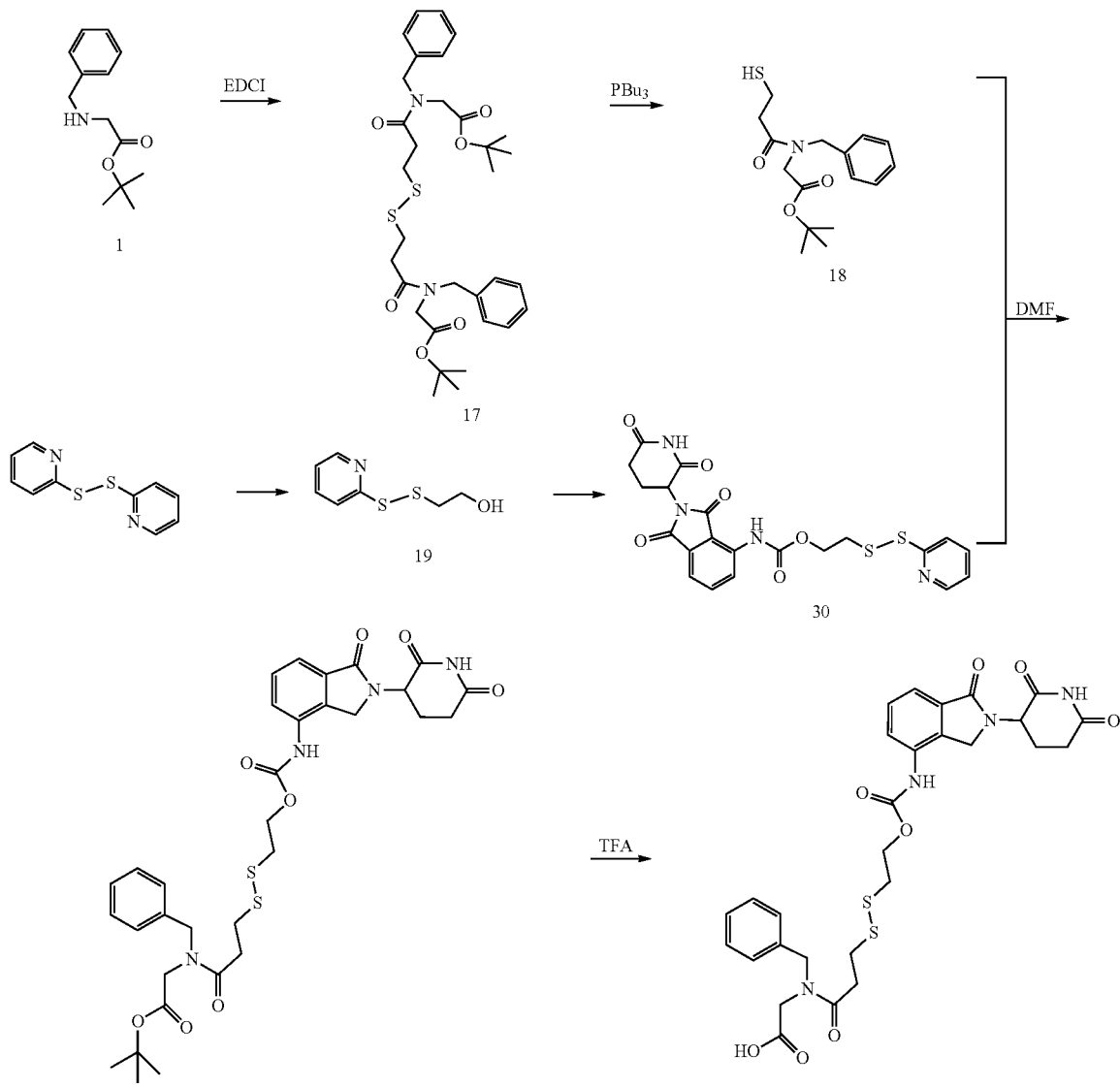

To a solution of compound 5 (2 g, 9.04 mmol) in DCM (20 ml), was added 3,3'-disulfanediyldipropanoic acid (0.95 g, 4.52 mmol) and DMAP (110 mg, 0.9 mmol). Then EDCI (2.61 g, 13.6 mmol) was added at 0° C. The mixture was din-3-yl)-1,3-dioxoiso-indolin-4-yl)carbamate (128 mg, 1 mmol). The mixture was stirred at RT overnight. The mixture was extracted with EA. The organic layer was washed with water and brine, dried over anhydrous $Na_2SO_4$, filtered, and concentrated to give a crude product, which was purified by a column chromatography to give compound 30 (90 mg, 28%).

To a solution of compound 30 (90 mg, 0.185 mmol) in DMF (5 ml) was added compound 18 (85.8 mg, 0.278 mmol). The mixture was stirred at RT overnight. The mixture was extracted with EA. The organic layer was washed with water and brine, dried over anhydrous $Na_2SO_4$, filtered, and concentrated to give a crude product, which was purified by a column chromatography to give compound 31 (64 mg, 50.4%).

Compound 31 (64 mg) was dissolved in 10 ml of TFA/DCM (3:7). The mixture was stirred at RT overnight, and concentrated. The crude mixture was purified by a column chromatography to give P-002 (26 mg, 44.2%): $^1$H NMR (CDCl$_3$, 300 MHz) δ 8.9 (m, 1H), 8.5-8.6 (m, 1H), 8.4-8.5 (m, 1H), 7.7-7.8 (m, 2H), 7.5-7.6 (m, 2H), 7.2-7.4 (m, 5H), 4.9-5.0 (m, 1H), 4.7-4.8 (s, 2H), 4.4-4.6 (m, 2H), 3.4-3.6 (m, 4H), 3.0-3.2 (m, 2H), 2.8-2.9 (m, 4H), 2.5-2.6 (m, 4H); LC-MS: m/z=651.4 (M+23)$^+$ Example 9: Synthesis of P-003

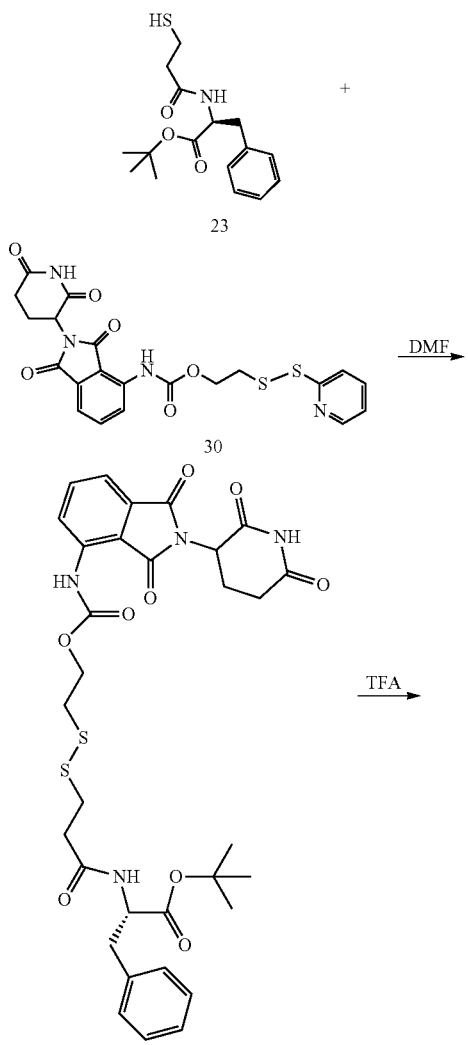

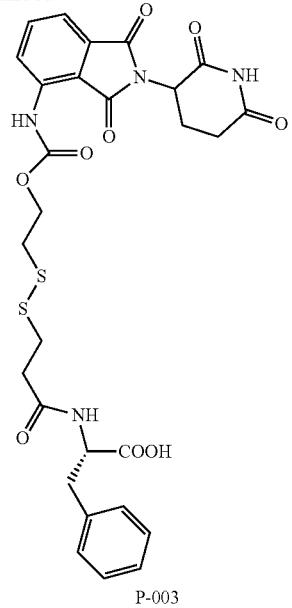

P-003

To a solution of compound 30 (250 mg, 0.514 mmol) in DMF (5 ml) was added compound 23 (238 mg, 0.771 mmol). The mixture was stirred at RT overnight. The mixture was extracted with EA. The organic layer was washed with water and brine, dried over anhydrous $Na_2SO_4$, filtered, and concentrated to give a crude product, which was purified by a column chromatography to give compound 32 (220 mg, 62.5%).

Compound 32 (220 mg) was dissolved in 10 ml of TFA/DCM (3:7). The mixture was stirred at RT overnight, and was concentrated, the crude mixture was purified by a column chromatography to give P-003 (140 mg, 69%): LC-MS: m/z=629.4 (M+1)$^+$ Example A: Non-Covalently Bound Complex of R-001 and Human Serum Albumin (HSA)

In each of two vials, 1 mg of R-001 was dissolved in 0.5 mL methanol. Water (1.5 ml) was then added into each of the vials. After shaking gently, a clear solution was obtained in both vials. 21.9 mg and 32.9 mg of HSA were added, respectively, into the vials. After shaking gently, a clear solution was obtained for both vials. Methanol was removed under vacuum until the volume of the solution was about 1.5 ml. A clear aqueous solution was obtained. Separately, the aqueous solutions were lyophilized overnight to give white solids, which were reconstituted by adding 0.5 mL water into the vials. A clear solution was obtained for each vial.

|  | HSA (mg) | |
| --- | --- | --- |
|  | 21.9 | 32.9 |
| Molar ratio of drug:HSA | 6 | 4 |

Example B: Non-Covalently Bound Complex of R-002 and HSA

In each of two vials, 1 mg of R-002 was dissolved in 0.5 mL methanol. Water (1.5 ml) was then added into each of the vials. After shaking gently, a clear solution was obtained in both vials. 21.9 mg and 32.9 mg of HSA were added, respectively, into the vials. After shaking gently, a clear solution was obtained. Methanol was removed under vacuum until the volume of the solution was about 1.5 ml. A clear aqueous solution was obtained for each. Separately, the aqueous solutions were lyophilized overnight to give the white solids, which were each reconstituted by adding 0.5 mL water. A clear solution was obtained for each vial.

|  | HSA (mg) | |
| --- | --- | --- |
|  | 32.9 | 21.9 |
| Molar ratio of drug:HSA | 4 | 6 |

Example C: Non-Covalently Bound Complex of R-003 and HSA

In each of three vials, 1 mg of R-003 was dissolved in 0.5 mL methanol. Water (1.5 ml) was then added into each of the vials. After shaking gently, a clear solution was obtained for all 3 vials. 21.8 mg, 26.2 mg and 32.7 mg of HSA were added, respectively, into the vials. After shaking gently, an almost clear solution was obtained for all 3 vials. Methanol was removed under vacuum until the volume of the solution was about 1.5 ml. A clear aqueous solution was obtained for each. Separately, the aqueous solutions were lyophilized overnight to give the white solids, which were each reconstituted by adding 0.5 mL water. A clear solution was obtained for all three samples.

|  | HSA (mg) | | |
| --- | --- | --- | --- |
|  | 32.7 | 26.2 | 21.8 |
| Molar ratio of drug:HSA | 4 | 5 | 6 |

Example D: Non-Covalently Bound Complex of R-004 and HSA

In each of three vials, 1 mg of R-004 was dissolved in 0.5 mL methanol. Water (1.5 ml) was then added into each of the vials. After shaking gently, a clear solution was obtained for all vials. 21.2 mg, 25.5 mg and 31.8 mg of HSA were added, respectively, into the vials. After shaking gently, a clear solution was obtained in each sample. Methanol was removed under vacuum until the volume of the solution was about 1.5 ml. A clear aqueous solution was obtained for each. Separately, the aqueous solutions were lyophilized overnight to give the white solids, which were each reconstituted by adding 0.5 mL water. A clear solution was obtained for all three samples.

|  | HSA (mg) | | |
| --- | --- | --- | --- |
|  | 31.8 | 25.5 | 21.2 |
| Molar ratio of drug:HSA | 4 | 5 | 6 |

Example E: Non-Covalently Bound Complex of R-005 and HSA

In each of two vials, 1 mg of R-005 was dissolved in 0.5 mL methanol. Water (1.5 ml) was then added into each of the vials. After shaking gently, a clear solution was obtained for both vials. 21.6 mg and 27.0 mg of HSA were added, respectively, into the vials. After shaking gently, a clear solution was obtained for both vials. Methanol was removed under vacuum until the volume of the solution was about 1.5 ml. A clear aqueous solution was obtained for each. Separately, the aqueous solutions were lyophilized overnight to give the white solids, which were each reconstituted by adding 0.5 mL water. A clear solution was obtained for both samples.

|  | HSA (mg) | |
| --- | --- | --- |
|  | 21.6 | 27.0 |
| Molar ratio of drug:HSA | 5 | 4 |

Example F: Non-Covalently Bound Complex of R-005 and HSA

R-005 (40 mg) was dissolved in methanol (20 ml) in a flask to give a clear solution. HSA (1080 mg) was dissolved in 60 ml of water. The methanol solution of R-005 was added dropwise into the flask of the HSA solution with stirring. Upon completion of the addition, a clear solution was obtained. The methanol was removed under vacuum until the volume of the solution was about 60 ml to give a clear solution. The resulting aqueous solution was lyophilized overnight to give a white solid. A sample of 20 mg was reconstituted by adding 0.5 mL water to give a clear solution.

Example AA: Persistence in Plasma

Test compounds and control (procaine) were incubated at a concentration of 10 μM with human plasma. The duplicate incubations, conducted in 96-well plates in a shaking water bath maintained at 37° C., were performed for 0 and 60 minutes and quenched by addition of acetonitrile. Ingredients for different incubations were added as shown in Table 1.

TABLE 1

Plasma Data Protocol

| | Add (μL) | | |
| --- | --- | --- | --- |
| Components | 0 min | 24 hr | 24 hr in PBS |
| Plasma | 100 | 100 | 0 |
| PBS Buffer (pH 7.4) | 90 | 90 | 90 |
| 20 μM Test Compound or Control in DMSO:PBS buffer (1:1) | 0 | 10 | 10 |
| Vortex | No | Yes | Yes |
| Incubated at 37° C. for 24 hr | Yes | Yes | Yes |
| Vortex | Yes | No | No |
| Acetonitrile (μL) | 500 | 500 | 500 |
| 20 μM Test Compound or Control in DMSO:PBS buffer (1:1) | 10 | 0 | 0 |
| Plasma | 0 | 0 | 100 |
| Incubation Sample Solution (25 μg/mL) (μL) | 20 | 20 | 20 |

TABLE 1-continued

Plasma Data Protocol

| | Add (µL) | | |
|---|---|---|---|
| Components | 0 min | 24 hr | 24 hr in PBS |
| Vortex | Yes | Yes | Yes |
| Centrifuge at 3500 rpm for 10 min | Yes | Yes | Yes |

After quenching by acetonitrile, the plates were capped, vortexed, and centrifuged at 3000 rpm for 10 minutes. The supernatant was injected into LC-MS/MS.

Peak area ratios of procaine and test compounds in incubation samples are listed in Table 2. Percent remaining values are calculated from peak area ratios from the equation shown below and are listed in Table 3.

$$\% \text{ Remaining} = 100 * \frac{PeakArea\ 1hr}{(PeakArea\ 0h - \text{Replicate 1} + PeakArea\ 0h - \text{Replicate 2})/2}$$

TABLE 2

Procaine and Test Compound Peak Area Ratio in Incubation Samples

| | Peak Area Ratio (Analyte/incubation sample) | | | | | |
|---|---|---|---|---|---|---|
| | Human Plasma | | | | PBS Buffer | |
| | 0 hr | | 24 hr | | 24 hr | |
| Compound | Replicate 1 | Replicate 2 | Replicate 1 | Replicate 2 | Replicate 1 | Replicate 2 |
| Procaine | 0.311 | 0.451 | 0.0 | 0.0 | 0.413 | 0.419 |
| R-005 and HSA Complex | 0.118 | 0.092 | 0.010 | 0.010 | 0.079 | 0.082 |

TABLE 3

Percent Remaining of Procaine and Test Compounds after 24-hr Incubation

| | % Remaining after 24-hr Incubation at 37° C. | | | | | |
|---|---|---|---|---|---|---|
| | Human Plasma | | | PBS buffer | | |
| Compound | Replicate 1 | Replicate 2 | Average | Replicate 1 | Replicate 2 | Average |
| Procaine | 0.0 | 0.0 | 0.0 | 108.40 | 109.97 | 109 |
| R-005 and HSA Complex | 9.0 | 9.0 | 9.0 | 75.5 | 77.8 | 76.7 |

Figure 2:
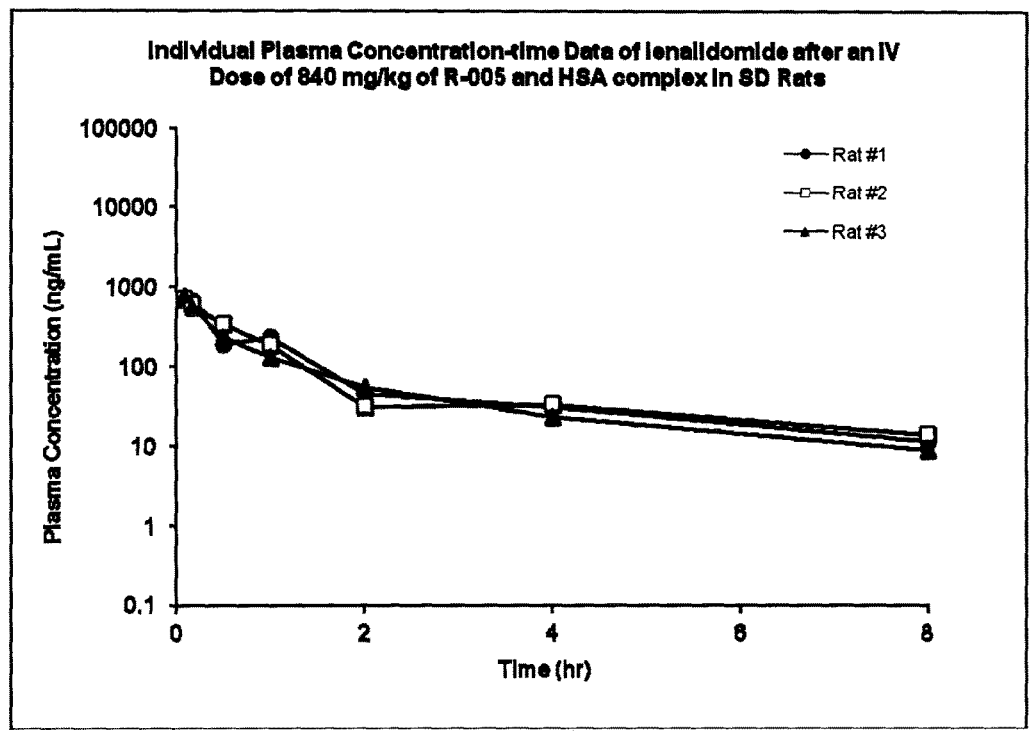
FIG. 2 contains a line plot showing individual plasma concentration-time data of lenalidomide after an IV dose of 840 mg/kg of R-005 and HSA complex in SD rats.

Example AB: Pharmacokinetics Study of Non-Covalently Bound Complex of R-005-HSA A group of 3 Sprague Dawley® ("SD") male rats were used in pharmacokinetics study. The dosing route of the study was IV. The dose for the PK study of non-covalently bound complex of R-005 and HSA was 840 mg/kg (an equivalent of a dose of about 30 mg/kg of R-005). The 10 time points for the study were 0.083, 0.167, 0.5, 1, 2, 4, 8, 24, 36 and 72 hr post dose. All blood samples were collected from cannula on the jugular vein. Blood samples were transferred into EDTA-K2 anti-coagulant tube and immediately placed on ice. After mixing on a rotator for 1 minute, the blood samples were centrifuged for 5 min at 3000× gravity ("g") and plasma was transferred to a microcentrifuge tube and kept in −80° C. freezer until processed for bio-analysis. An LC-MS/MS method was developed for compound R-005 and lenalidomide in male SD rat plasma. lenalidomide can be formed in vivo after compound R-005 dissociates from HSA and is metabolized in vivo. FIG. 1 shows individual plasma concentration-time data for Compound R-005 after an IV dose of 840 mg/kg of the Compound R-005-HSA complex in SD rats. FIG. 2 shows individual plasma concentration-time data for lenalidomide after an IV dose of 840 mg/kg of the Compound R-005-HSA complex in SD rats. Table 4 shows the PK parameters for Compound R-005 and lenalidomide after an IV dose of 840 mg/kg of the Compound R-005-HSA complex in SD rats.

TABLE 4

| Compound | CL (mL/min/kg) | Vss (L/kg) | Terminal $T_{1/2}$ (hr) | $AUC_{last}$ (hr * ng/mL) |
|---|---|---|---|---|
| R-005 | 58.1 | 0.459 | 0.464 | 8797 |
| lenalidomide | 361 | 50.2 | 3.39 | 640 |

A number of embodiments have been described. Nevertheless, it will be understood that various modifications may be made without departing from the spirit and scope of the disclosure. Accordingly, other embodiments are within the scope of the following claims.

What is claimed is:

1. A non-covalently bound complex of a compound of formula:

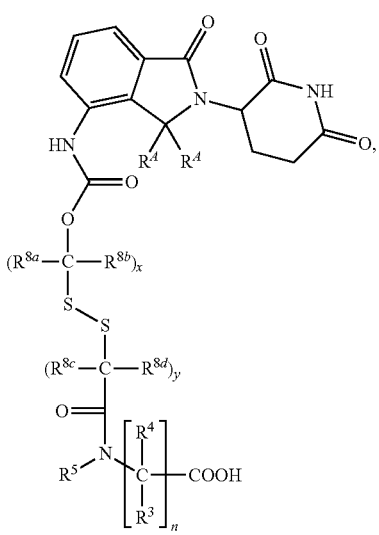

or pharmaceutically acceptable salt thereof,
wherein
each $R^4$ is H, or both $R^4$ taken together is oxo;
$R^3$ is independently in each instance H, alkyl, alkenyl, alkynyl, alkyl-O-alkyl, alkyl-O-aryl, phenyl, or alkaryl, wherein the alkyl, alkenyl, alkynyl, alkyl-O-alkyl, alkyl-O-aryl, phenyl, or alkaryl is optionally substituted with 1-3 substituents independently selected from the group consisting of: halo, —$NO_2$, —$CF_3$, amido, sulfonamide, aryl, —OH, alkyl, —O-lower alkyl, —O-alkaryl, and —O-aryl;
$R^4$ is independently in each instance H, OH, $NO_2$, $NH_2$, SH or a branched or unbranched $C_{1-10}$ alkyl, $C_{2-10}$ alkenyl or $C_{2-10}$ alkynyl, wherein the $C_{1-10}$ alkyl, $C_{2-10}$ alkenyl or $C_{2-10}$ alkynyl is optionally substituted with 1-2 substituents independently selected from the group consisting of halo, OH, $NO_2$, $NH_2$, SH and =O, and wherein the $C_{1-10}$ alkyl, $C_{2-10}$ alkenyl or $C_{2-10}$ alkynyl optionally has 1-2 heteroatoms independently selected from O, S and NH wherein each heteroatom replaces a $CH_2$, with the proviso that no O, S or N atom in the $C_{1-10}$ alkyl, $C_{2-10}$ alkenyl or $C_{2-10}$ alkynyl is covalently bonded to another O, S or N atom;
$R^5$ is H, alkyl, alkenyl, alkynyl, alkyl-O-alkyl, alkyl-O-aryl, phenyl, or alkaryl, wherein the alkyl, alkenyl, alkynyl, alkyl-O-alkyl, alkyl-O-aryl, phenyl, or alkaryl is optionally substituted with 1-3 substituents independently selected from the group consisting of: halo, —$NO_2$, —$CF_3$, amido, sulfonamide, aryl, —OH, alkyl, —O-lower alkyl, —O— alkaryl, and —O-aryl;
each of $R^{8a}$, $R^{8b}$, $R^{8c}$, and $R^{8d}$ is independently in each instance H or lower alkyl;

x is 1, 2, 3, 4, 5, 6, 7, or 8;

y is 1, 2, 3, 4, 5, 6, 7, or 8; and n is 1, 2, 3, 4, 5, or 6, and human serum albumin, wherein the compound and human serum albumin is in a molar ratio in the range of from about 1:1 to about 10:1, wherein the non-covalently bound complex has solubility in aqueous solution of 5 mg/mL or more.

2. The non-covalently bound complex of claim 1, wherein the compound has structure:

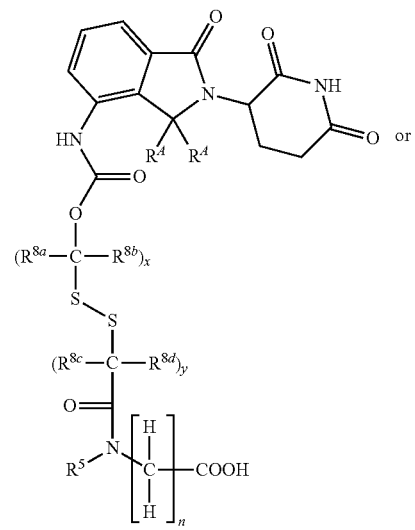

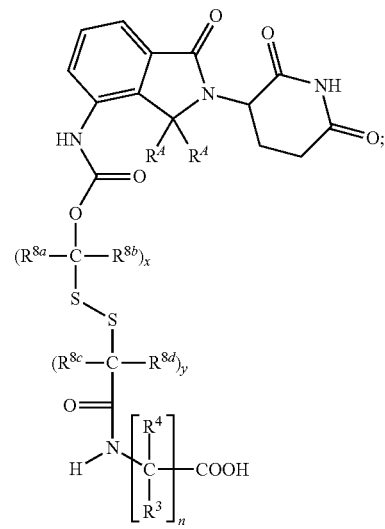

wherein:
x is 1, 2, or 3;
y is 1, 2, or 3; and
n is 1 or 2.

3. The non-covalently bound complex of claim 1, wherein the compound is selected from the group consisting of:

83
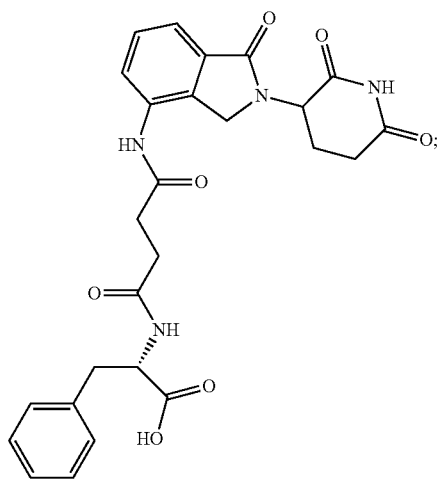
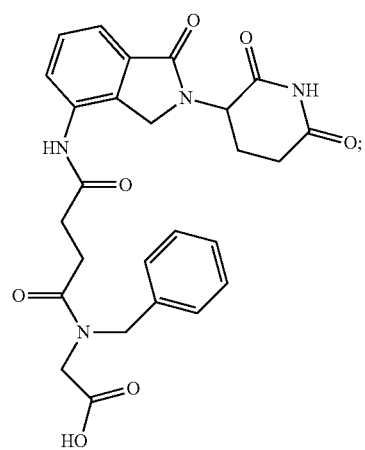
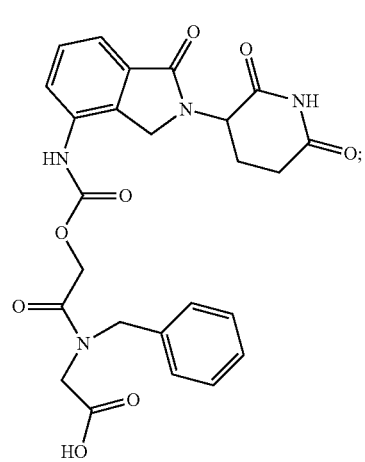
84
-continued
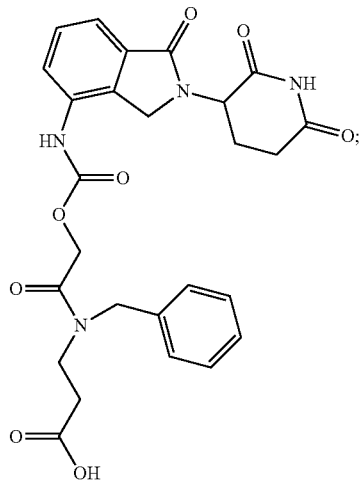
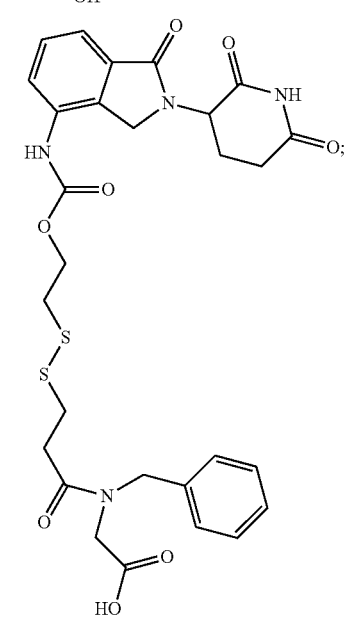
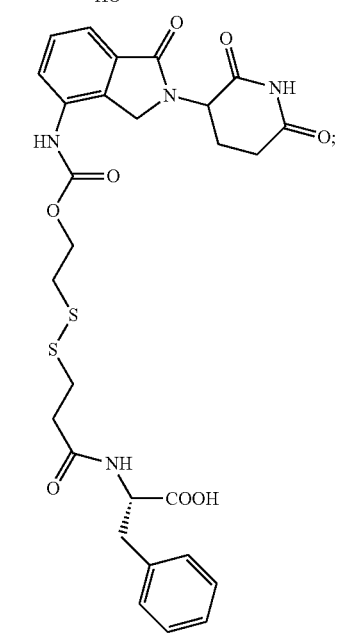

85
-continued
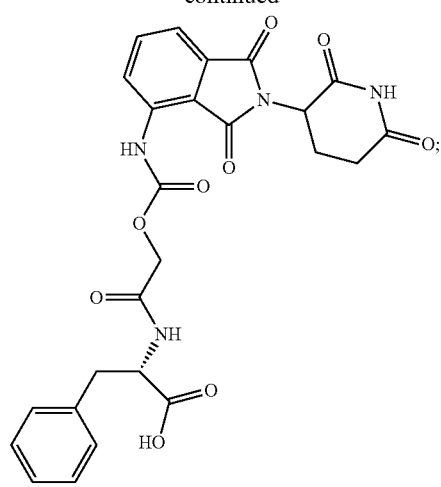
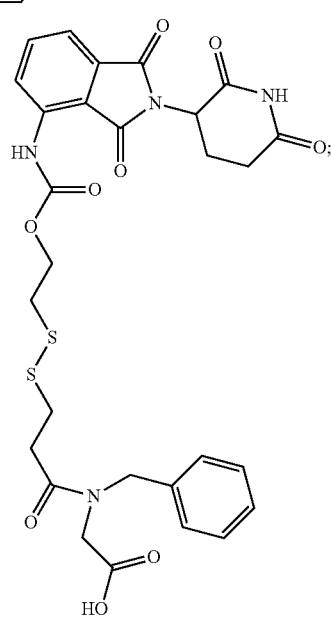
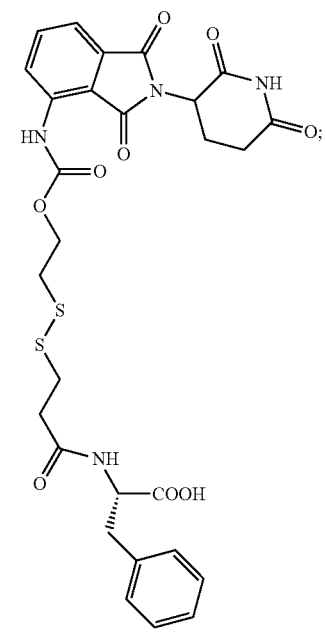
86
-continued
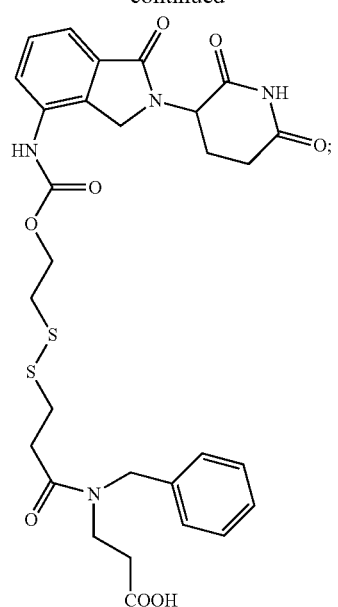
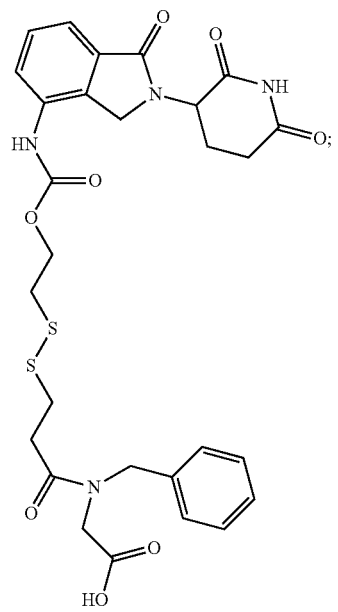

87
-continued
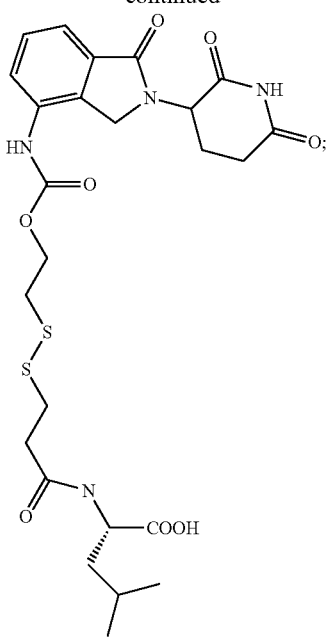
88
-continued
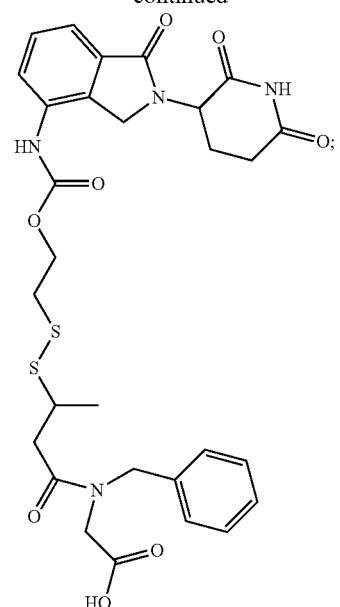
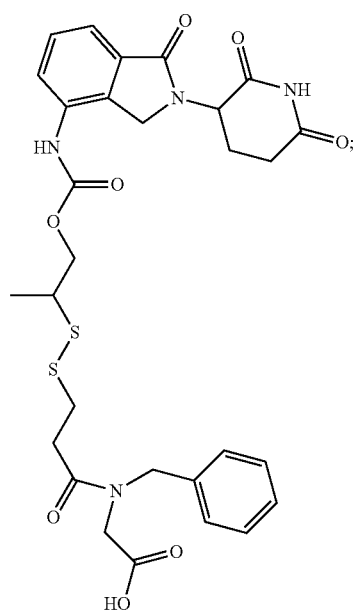
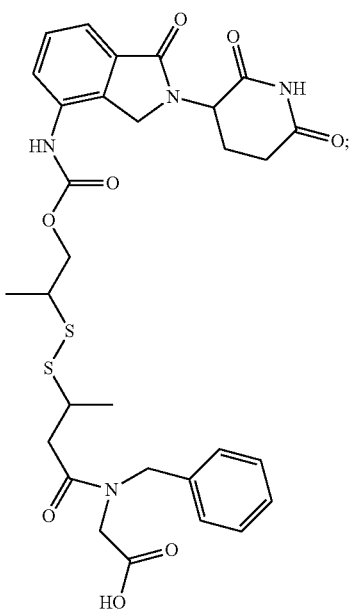

89
-continued
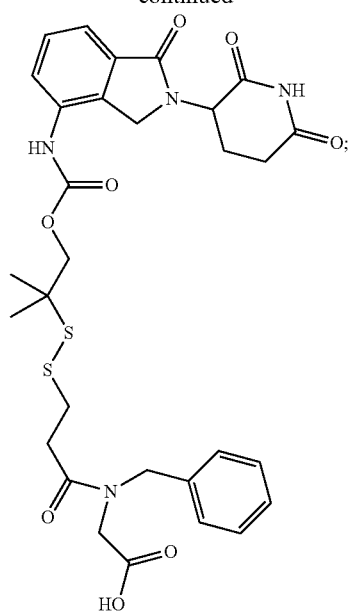
90
-continued
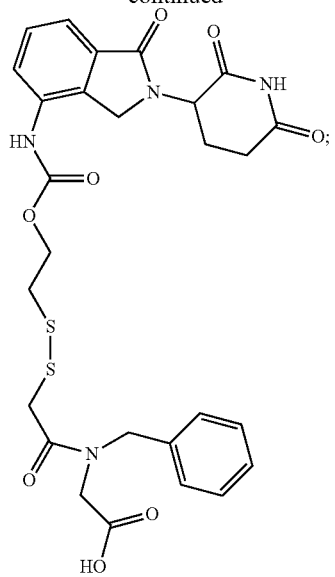
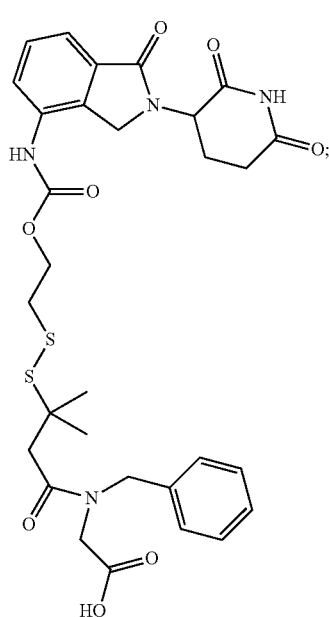
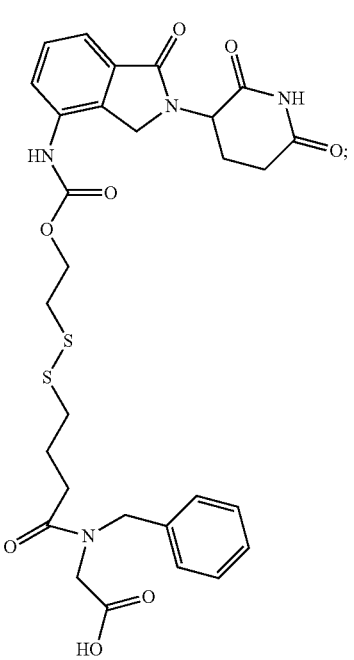

91
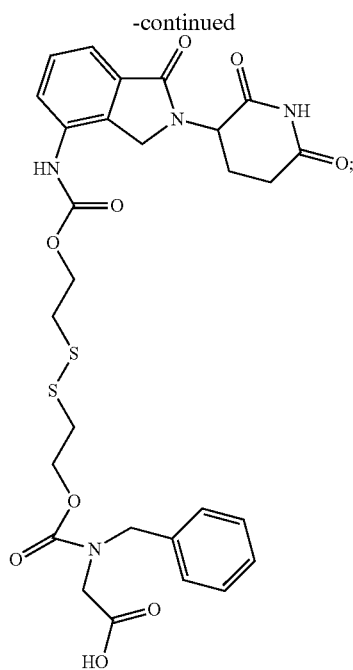
92
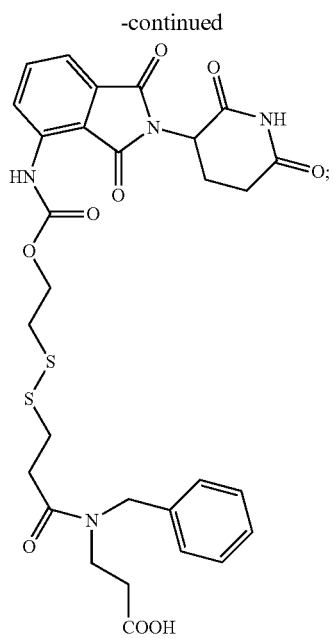
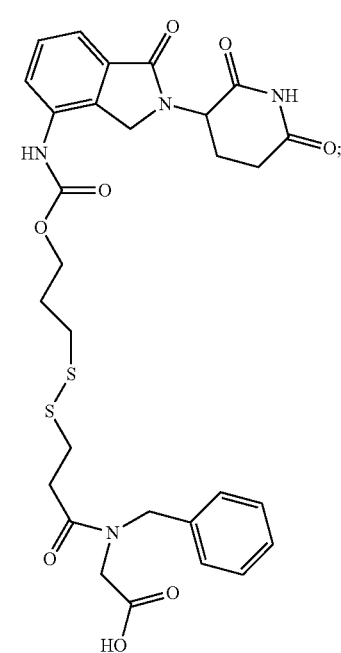
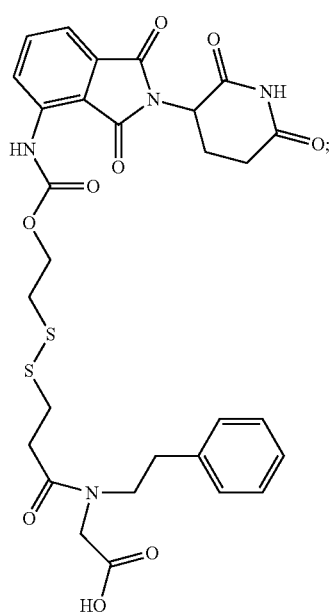

93 -continued
94 -continued
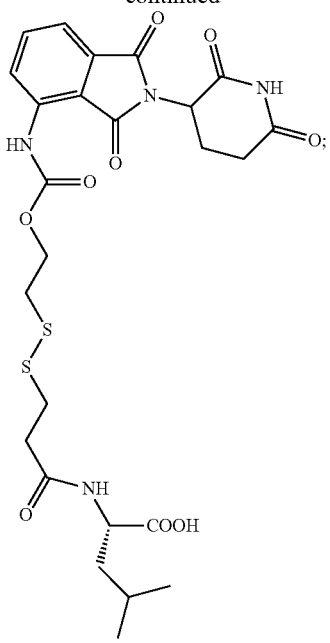
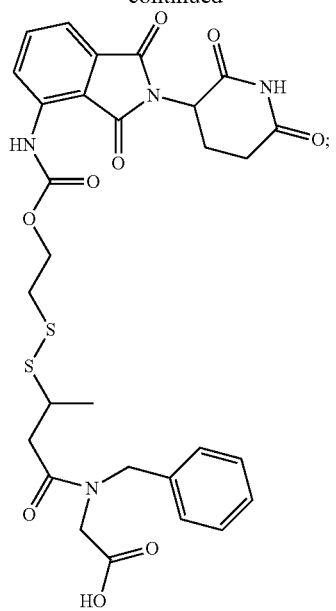

95
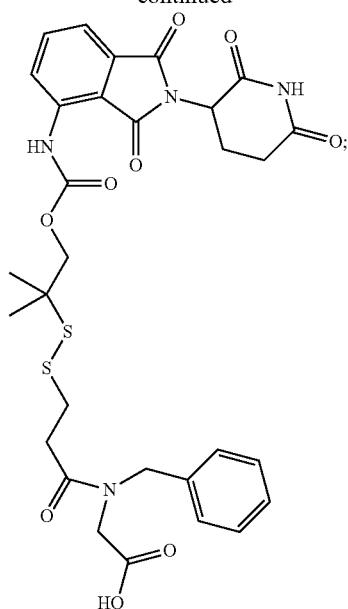
96
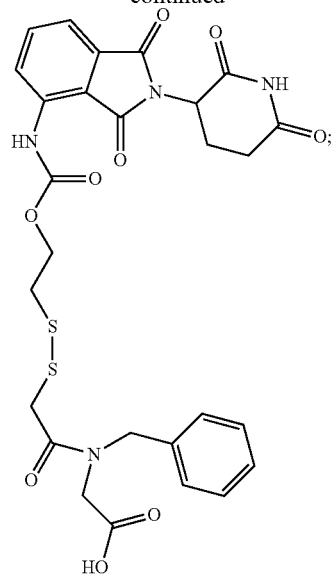

-continued

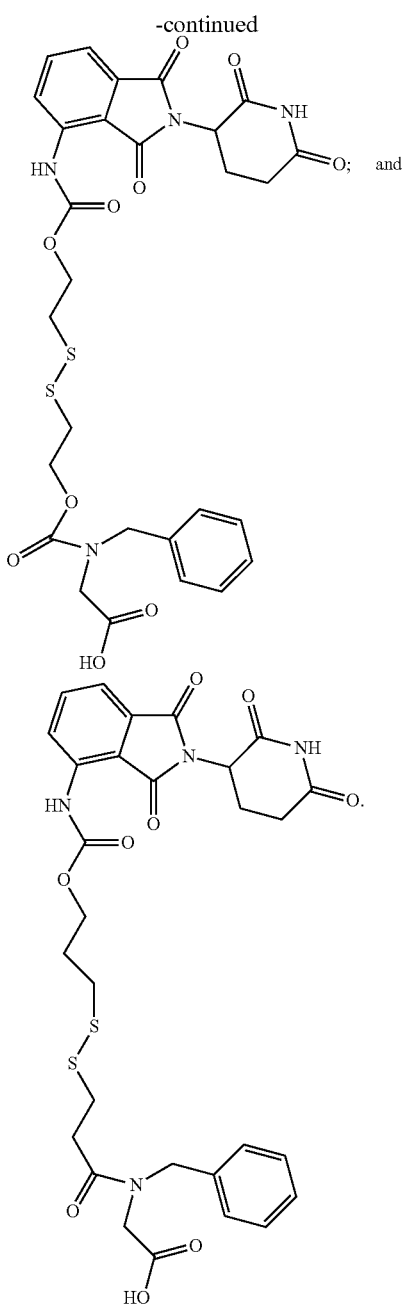

and

4. The non-covalently bound complex of claim 1, wherein the compound and human serum albumin is in a molar ratio in the range of from about 1:1 to about 7:1.

5. The non-covalently bound complex of claim 1, wherein the compound and human serum albumin is in a molar ratio in the range of from about 2:1 to about 6:1.

6. The non-covalently bound complex of claim 1, wherein the compound and human serum albumin is in a molar ratio in the range of from about 3:1 to about 5:1.

7. The non-covalently bound complex of claim 4, wherein the non-covalently bound complex is in a solid formulation.

8. The non-covalently bound complex of claim 4, wherein the non-covalently bound complex is in an aqueous formulation.

9. The non-covalently bound complex of claim 8, wherein the aqueous formulation is substantially free of solvents other than water.

10. A pharmaceutical composition comprising a non-covalently bound complex of claim 1, and a pharmaceutically acceptable carrier.

11. A method of treating a cancer, the method comprising the step of administering to a subject in need thereof a therapeutically effective amount of a pharmaceutical composition of claim 10.

12. The method of claim 11, wherein the cancer is multiple myeloma.

13. The method of claim 11, wherein the cancer is myelodysplastic syndrome.

14. The method of claim 11, wherein the cancer is mantle cell lymphoma.

* * * * *